US011426448B2

(12) United States Patent
Podlasek et al.

(10) Patent No.: US 11,426,448 B2
(45) Date of Patent: Aug. 30, 2022

(54) METHODS FOR TREATMENT OF ERECTILE DYSFUNCTION WITH SONIC HEDGEHOG COMPOUNDS

(71) Applicants: NORTHWESTERN UNIVERSITY, Evanston, IL (US); THE BOARD OF TRUSTEES OF THE UNIVERSITY OF ILLINOIS, Urbana, IL (US); BOARD OF TRUSTEES OF SOUTHERN ILLINOIS UNIVERSITY, Springfield, IL (US); THE BOARD OF REGENTS OF THE UNIVERSITY OF TEXAS SYSTEM, Austin, TX (US)

(72) Inventors: Carol Podlasek, Chicago, IL (US); Samuel I. Stupp, Evanston, IL (US); Kevin McVary, Carbondale, IL (US); Dan Harrington, Houston, TX (US)

(73) Assignees: NORTHWESTERN UNIVERSITY, Evanston, IL (US); THE BOARD OF TRUSTEES OF THE UNIVERSITY OF ILLINOIS, Urbana, IL (US); BOARD OF TRUSTEES OF SOUTHERN ILLINOIS UNIVERSITY, Springfield, IL (US); THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 16/410,789

(22) Filed: May 13, 2019

(65) Prior Publication Data
US 2019/0367572 A1 Dec. 5, 2019

Related U.S. Application Data

(60) Provisional application No. 62/670,473, filed on May 11, 2018.

(51) Int. Cl.
*A61K 38/18* (2006.01)
*A61P 15/10* (2006.01)
*C07K 14/47* (2006.01)
*A61K 38/00* (2006.01)
*C07K 14/475* (2006.01)

(52) U.S. Cl.
CPC .............. *A61K 38/18* (2013.01); *A61P 15/10* (2018.01); *A61K 38/00* (2013.01); *C07K 14/47* (2013.01); *C07K 14/475* (2013.01); *C07K 14/4705* (2013.01)

(58) Field of Classification Search
CPC .............................. C07K 14/47; A61K 38/17
See application file for complete search history.

(56) References Cited

PUBLICATIONS

NCBI Record for NP_00129739.1; available at https://www.ncbi.nlm.nih.gov/protein/881717124/; 3 pages as printed; dated Apr. 26, 2020.*
Hehemann et al, Apr. 1, 2017, Journal of Urology. vol. 197, Issue 4S.*
Hoyland et al (2014. Rev Urol. 16(4): 181-188.*
Hehemann et al #2 (Abstract MP45-08), Apr. 1, 2017, Journal of Urology. vol. 197, Issue 4S.*
Choe et al, Abstract MP45-06, Apr. 1, 2017, Journal of Urology, 197(4S): e613.*
Podlasek et al, 2007. Biol Reprod. 76(1): 19; 23 pages as printed.*
Recombinant Mouse Sonic Hedgehog datasheet, R&D Systems, Nov. 10, 2005; no author indicated.*
Angeloni et al., "Regeneration of the cavernous nerve by Sonic hedgehog using aligned peptide amphiphile nanofibers." Biomaterials 2011, 32, 1091-1101.
Angeloni et al., "Sonic hedgehog is neuroprotective in the cavernous nerve with crush injury." J Sex Med 2013, 10, 1240-1250.
Bond et al., "Peptide amphiphile nanofiber delivery of sonic hedgehog to reduce smooth muscle apoptosis in the penis after cavernous nerve resection." J Sex Med 2011, 8, 78-89.
Choe et al., "Optimization of Sonic hedgehog delivery to the penis from self-assembling nanofiber hydrogels to preserve penile morphology after cavernous nerve injury." Nanomedicine: Nanotechnology, Biology, and Medicine 2019, 20, 102033, 1-10.
Choe et al., "Peptide amphiphile nanofiber hydrogel delivery of sonic hedgehog to the cavernous nerve to promote regeneration and preserve erectile dysfunction." Nanomedicine: Nanotechnology, Biology and Medicine 2017, 13, 95-101.
Choe et al., "Sonic hedgehog delivery from self-assembled nanofiber hydrogels reduces the fibrotic response in models of erectile dysfunction." Acta Biomaterialia 2016, 32, 89-99.
Dobbs et al., "Peptide amphiphile delivery of sonic hedgehog protein promotes neurite formation in penile projecting neurons." Nanomedicine 2018, 14, 2087-2094.
Dobbs et al., "Sonic hedgehog regulation of cavernous nerve regeneration and neurite formation in aged pelvic plexus." Experimental Neurology 2019, 312, 10-19.
Hehemann et al., "Pelvic and hypogastric nerves are injured in a rat prostatectomy model, contributing to development of stress urinary incontinence." Scientific Reports 2018, 8, 16432.
Hehemann et al., "Sonic hedgehog regulation of human rhabdosphincter muscle: Potential implications for treatment of stress urinary incontinence." Neurourology and Urodynamics 2018, 1-9.

* cited by examiner

Primary Examiner — Zachary C Howard
(74) Attorney, Agent, or Firm — Casimir Jones, S.C.; Rikki A. Hullinger

(57) ABSTRACT

Provided herein is technology relating to compositions comprising sonic hedgehog protein and therapeutic uses thereof. In particular, the technology relates to compositions comprising a hedgehog protein and one or more peptide amphiphiles for use in methods of treating or preventing stress urinary incontinence and/or erectile dysfunction in a subject.

11 Claims, 40 Drawing Sheets
(34 of 40 Drawing Sheet(s) Filed in Color)
Specification includes a Sequence Listing.

Fluorogold was injected into the urethra and bladder wall

SHH protein is abundant at the crush site.

nNOS

GAP43

FIG. 16A
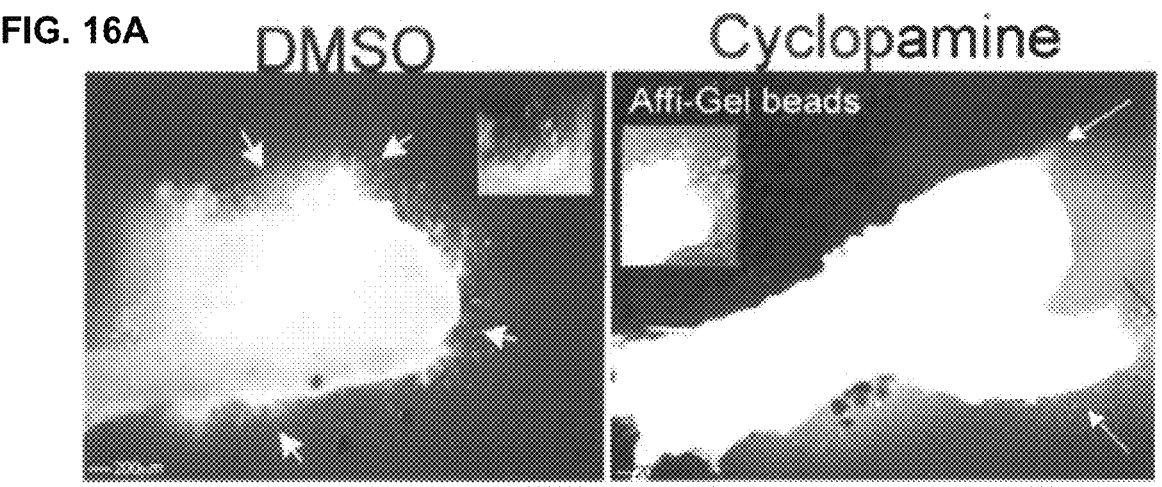
FIG. 16B
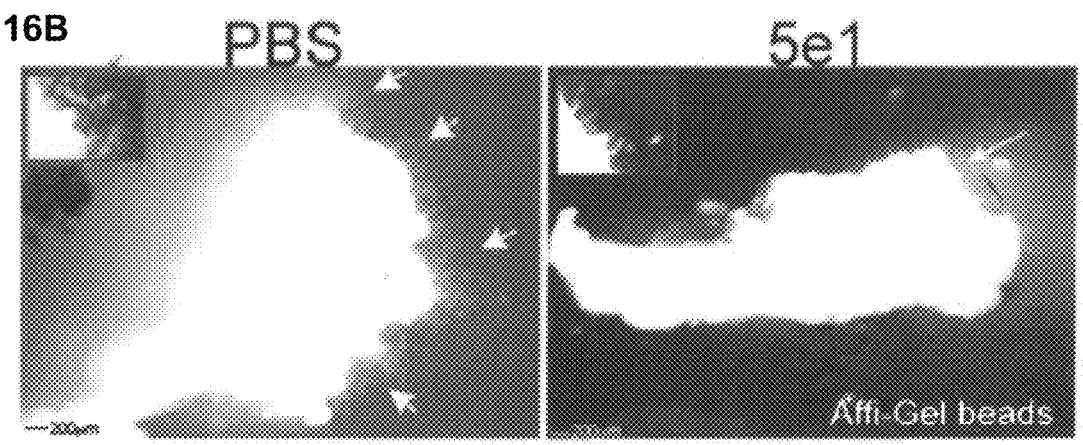
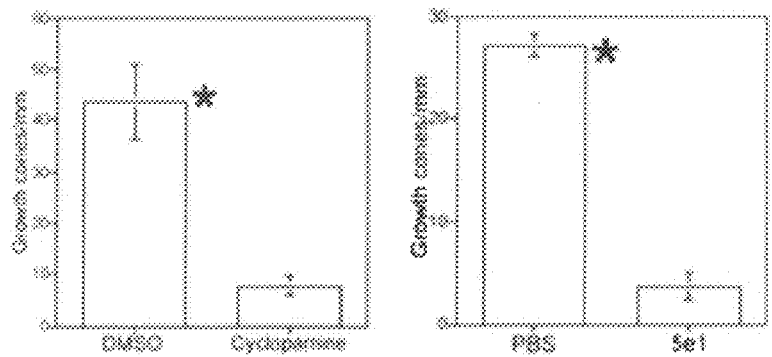
FIG. 16C

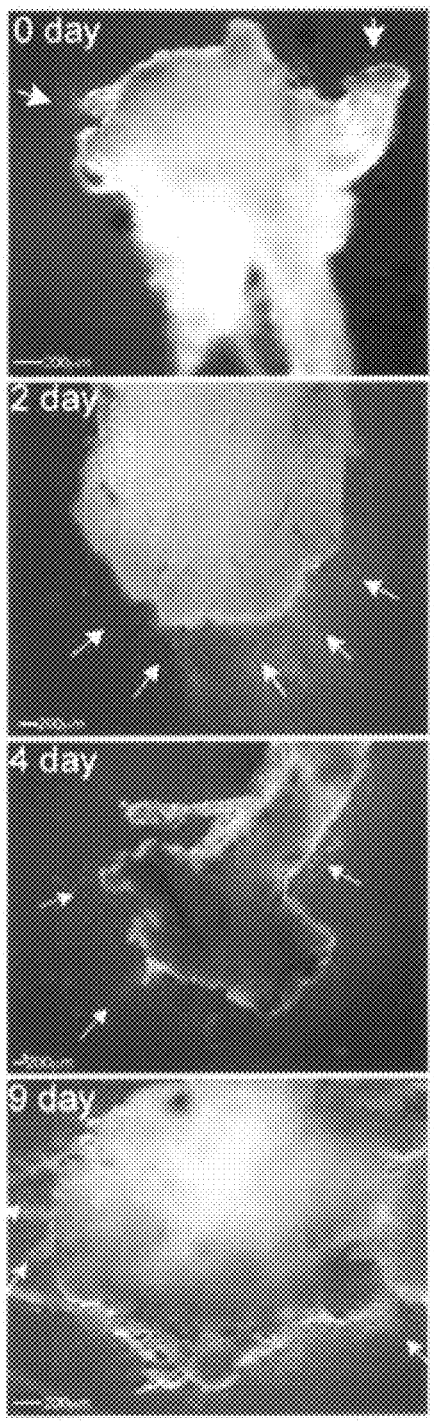
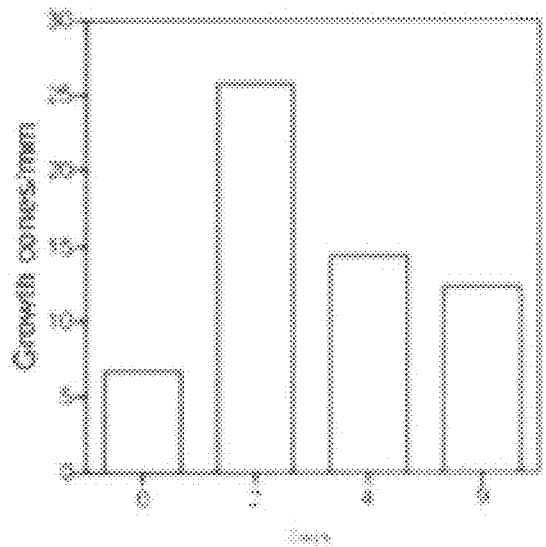
FIG. 17B
FIG. 17A

SHH was withheld initially then given for 4 days in organ culture.

SHH was given initially and then withheld in organ culture.

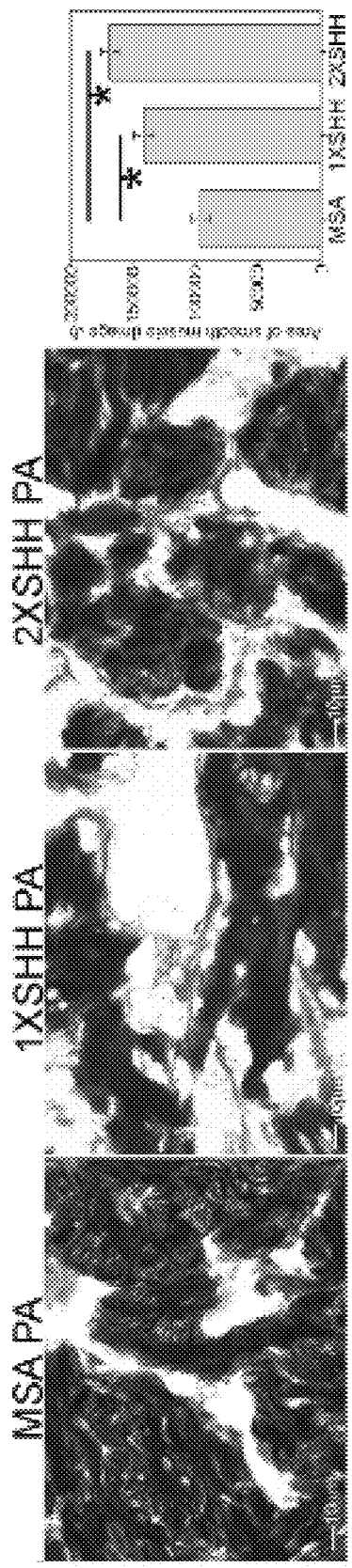
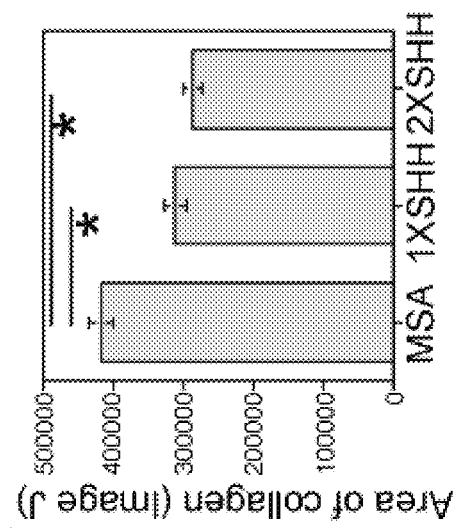
FIG. 20B
FIG. 20C

METHODS FOR TREATMENT OF ERECTILE DYSFUNCTION WITH SONIC HEDGEHOG COMPOUNDS

PRIORITY

This application claims priority to U.S. Provisional Patent Application No. 62/670,473, filed May 11, 2018, the entire contents of which are incorporated herein by reference.

STATEMENT OF FEDERAL INTEREST

This invention was made with government support under grant number R01DK101536 awarded by the NIH. The government has certain rights in the invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 6,848 Byte ASCII (Text) file named "37785-202_ST25.TXT," created on Aug. 28, 2019.

FIELD OF INVENTION

Provided herein is technology relating to compositions comprising sonic hedgehog protein and a delivery vehicle and therapeutic uses thereof. In particular, the technology relates to compositions comprising a sonic hedgehog protein and one or more peptide amphiphiles for use in methods of treating or preventing stress urinary incontinence and/or erectile dysfunction in a subject.

BACKGROUND

Stress urinary incontinence (SUI) is an important public health concern, affecting both men and women, and with increasing incidence in the elderly. In particular, SUI affects men following prostatectomy. While it is possible to regain reasonable urinary control following prostatectomy through pelvic floor strengthening exercises, many will suffer from bothersome SUI requiring incontinence pads and garments, with detrimental impact on quality-of-life. Surgical therapies for SUI, including urethral slings and artificial urinary sphincters, have variable outcomes and significant side effects, including device failure, erosion of the urethra, transient pain and infection, and urinary retention, leading to a revision rate of 80% of patients by 10-15 years. Thus, there is a critical unmet need for methods to prevent or treat stress urinary incontinence, with important clinical implications not only for men undergoing prostatectomy, but also for all patients suffering from the stigma of urinary incontinence.

Erectile dysfunction (ED) critically impacts quality of life in prostatectomy, diabetic and aging patients. The underlying mechanism involves cavernous nerve (CN) damage, resulting in ED in 80% of prostatectomy patients. Loss of innervation causes smooth muscle apoptosis in the penis, which initiates a remodeling process in the corpora cavernosa, leading to a fibrotic penis that can no longer respond to normal neurotransmitter signaling mechanisms. Moreover, state of the art treatments are ineffective in up to 69% of ED patients with peripheral neuropathy. Thus, novel methods to prevent or treat ED are needed.

SUMMARY

Provided herein are compositions comprising a sonic hedgehog protein and a delivery vehicle. In some embodiments, the delivery vehicle comprises one or more peptide amphiphiles. In some embodiments, each peptide amphiphile comprises a hydrophobic tail comprising an 8-24 carbon alkyl chain ($C_{8-24}$), a structural peptide segment comprising $V_2A_2$ or $V_3A_3$, a charged peptide segment comprising $E_{2-4}$, and a C-terminal moiety independently selected from —H, —OH, —COOH, —COONH$_2$, and —NH$_2$. In some embodiments, each peptide amphiphile comprises $C_{16}$—$V_3A_3E_3$-COOH or $C_{16}$—$V_2A_2E_2$-NH$_2$.

The compositions provided herein may be administered to a subject to achieve various therapeutic purposes. In some embodiments, the compositions may be used in methods for treating and/or preventing stress urinary incontinence in a subject. In some embodiments, the composition may be administered to the subject prior to or at the time of prostatectomy or to prevent stress urinary incontinence in a subject. The composition may be administered to the subject by applying to one or more of the pelvic ganglia, hypogastric nerve, the pelvic nerve, and the rhabdosphincter of the subject.

In other embodiments, the compositions may be used in methods for treating and/or preventing erectile dysfunction in a subject. The composition may be administered to the subject by applying to one or more of the corpora cavernosa, the pelvic ganglia, and the cavernous nerve of the subject.

Additional embodiments will be apparent to persons skilled in the relevant art based on the teachings contained herein.

BRIEF DESCRIPTION OF THE DRAWINGS

The patent or application file contains at least one drawing executed in color. Copies of this patent or patent application publication with color drawings will be provided by the Office upon request and payment of the necessary fee.

(FIG. 1A) Trichrome stain of human RS indicates abundant striated skeletal muscle and collagen. Arrows indicate muscle. IHC analysis of human RS shows SHH, PTCH1 and SMO protein localization in RS muscle. (FIG. 1B) GLI-1, GLI-2 and GLI-3 are abundant in RS muscle. Arrows indicate protein. 100-200× magnification.

(FIG. 2A) Photo of cells outgrowing in the primary culture. Muscle cells have characteristic skeletal muscle shape (FIG. 2B) and stain intensely with skeletal muscle ACTIN (FIG. 2C). Nuclei were stained with DAPI (blue). Arrows indicate muscle cells 100-400× magnification. (FIG. 2D) Skeletal muscle fibers stained intensely for ACTIN (red) whereas SHH protein (green) was abundant both in the cytoplasm and perinuclear region of the RS muscle cells. Nuclei were stained with DAPI (blue). Arrows indicate protein. 400× magnification.

(FIG. 4A) Rat pelvic plexus. CN=cavernous nerve. PN=pelvic nerve. MPG=pelvic ganglia. HYG=hypogastric nerve ANC=accessory nerves. (FIG. 4B) Diagram of a neuron including the cell body, nucleus, axon. Schwann cells and satellite glial cells. (FIG. 4C) Diagram of fluorogold injection into the wall of the bladder and urethra (arrows).

(FIG. 5A) Sham MPG show many fluorogold staining neurons, indicating intact innervation.

(FIG. 6A) Immunohistochemical analysis for caspase 3 cleaved protein (apoptotic marker) in the MPG of rats that underwent sham surgery, where the MPG was exposed but the nerves were uninjured. Caspase 3 cleaved protein was present at a low level in the CN, PN, HYG and ANC nerves, indicating a low level of apoptosis under normal homeostatic conditions. Arrows indicate caspase 3 cleaved protein. 100× magnification. (FIG. 6B) TUNEL assay of the sham rat MPG confirms a low level of apoptosis in all nerves of the MPG Arrows indicate apoptotic cells 100× magnification.

(FIG. 7A) Immunohistochemical analysis for caspase 3 cleaved protein in the CN, PN, HYG, and ANC nerves of the rat MPG, 1-7 days after bilateral CN crush/MPG tension injury. Abundant caspase 3 protein was observed in all of the MPG nerves, in a time dependent manner, in response to CN crush. Staining appeared primarily in glial cells of the MPG and Schwann cells of the nerves. Arrows indicate caspase 3 cleaved protein. 200-400× magnification. (FIG. 7B) TUNEL assay of CN, PN, HYG, and ANC nerves 1-7 days after CN crush injury. Apoptosis appeared primarily in glial/Schwann cells of all nerves in a time dependent manner after CN crush injury. Arrows indicate apoptotic cells. 200-400× magnification.

(FIG. 8A) Immunohistochemical analysis of caspase 9 protein in MPG, CN, PN, and ANC nerves, 1-7 days after CN crush injury Caspase 9 protein was identified primarily in glial/Schwann cells of all MPG nerves and in a small number of neurons, indicating that the mechanism of how apoptosis takes place in the pelvic plexus after injury is primarily through the intrinsic apoptotic pathway. Arrows indicate caspase 9 protein 200-400× magnification. (FIG. 8B) Immunohistochemical analysis of caspase 8 protein in MPG, CN, PN, and ANC nerves, 1-7 days after CN crush injury. Caspase 8 protein was absent in all pelvic plexus nerves, indicating the absence of extrinsic apoptotic pathway activity. 200-400× magnification.

(FIG. 13A) Diagram of the MPG and CN with crush injury. (FIG. 13B) Diagram of Wallerian degeneration in the CN in response to crush injury. The axonal skeleton and membrane break apart. Schwann cells proliferate, phagocytize the debris, and release cytokines that recruit macrophages. The proximal end of damaged axons attempts repair, which involves initial swelling and some retrograde degeneration, clearing of debris and axonal sprouting-neurite formation. Neurites grow towards bands of Büngner, which are formed of aligned Schwann cells. Neurites are attracted by growth factors produced by Schwann cells. (FIG. 13C) Immunohistochemical analysis for SHH protein in the CN four days after crush injury shows abundant SHH protein on either side of the crush site. Arrows indicate SHH protein. 200× magnification. MPG=major pelvic ganglia CN=cavernous nerve.

(FIG. 14A) Magnified view of neurites that grow from MPG and CN tissue in organ culture shows both elongating fibers and growth cones. Arrows indicate growth cones. Red line indicates enlarged region. (FIG. 14B) IHC analysis was performed for nNOS, a marker of penile projecting neurons, in order to confirm that dissection of the MPG only included the caudal portion of the MPG that provides innervation to the penis. Since antibodies do not migrate well within intact tissue, we sectioned the MPG/CN tissue prior to staining, nNOS was abundant in elongating neurites in the CN and in sprouting neurons of the MPG. Arrows indicate neurites and growth cones. (FIG. 14C) IHC for GAP43, a growth cone marker, was performed to confirm that what we are visualizing is neurite formation. Arrows indicate staining. Affi-Gel bead delivery vehicles, which were used to deliver PBS control, are high-lighted with asterisks, and non-specifically stain with fluorescent secondary. 100-200× magnification.

FIGS. 16A-16C: Normal adult MPG and CN tissues were grown in organ culture for three days with Affi-Gel beads delivering either the SHH inhibitor cyclopamine and DMSO control (FIG. 16A, FIG. 16C), or 5e1 SHH inhibitor and PBS control (FIG. 16B, FIG. 16C). Neurite formation was inhibited (particularly in the region near the Affi-Gel beads) by 82% with cyclopamine, and 86% with 5e1 SHH inhibitor. Arrows indicate neurites. Red lines represent enlarged regions. 50× magnification.

FIGS. 17A-17B: MPG and CN tissue from Sprague Dawley rats that underwent bilateral CN crush, and MPG/CN tissues were harvested at time of crush, and after 2, 4 and 9 days, and were grown in organ culture for 4 days. (FIG. 17A) Neurite formation was observed at all time points after CN crush, with most abundant neurites observed at 2 days after CN crush. While less abundant, neurite formation was possible at later time points after CN injury, with a similar neurite sprouting potential observed after 4 and 9 days. Arrows indicate neurites. 50-80× magnification. Number of grown cones per millimeter are quantified in FIG. 17B.

(FIG. 18A) Very little neurites were observed after CN injury with continuous MSA treatment. (FIG. 18B) Continuous SHH treatment induced intense neurite formation in a wide area along the MPG and CN. The number of neurites increased by 298%0/with SHH treatment. Number of grown cones per millimeter in the various treatment conditions are quantified in FIG. 18C. (FIG. 18D) SHH protein treatment was able to rescue neurite sprouting potential, with an increase of 181% in the number of neurites even when not given until four days after crush injury. (FIG. 18E) When SHH protein was applied initially for four days in vivo, and then withheld in organ culture, neurites increased 141% in comparison to MSA controls, and continued to grow at a lower level once initiated, in comparison to continuous SHH treated MPG/CN. Arrows indicate neurites and the PA vehicle. Red lines represent enlarged regions. 50-80× magnification.

FIGS. 20A-20C. Apoptotic index was quantified at 4 days after injury in corpora cavernosal tissue of Sprague Dawley rats that underwent sham surgery or CN crush and 1×SHH, 2×SHH or MSA (control) treatment by PA injected into the corpora cavernosa. (FIG. 20A) Apoptosis increased 117% 4 days after CN injury (p=0.0001). SHH PA suppressed apoptosis 27% (p=0.005). Doubling the concentration of SHH protein delivered to the penis decreased the apoptotic index 29% (p=0.003), which was not significantly different from the 1×SHH treated group (p=0.999). Results are quantified in the bottom right panel. (FIG. 20B) Trichrome stain quantification of smooth muscle showed 48% more smooth muscle in the 1×SHH treated group (p=0.005). Doubling the concentration of SHH resulted in 76% more smooth muscle (p=0.0001). There was no significant difference in smooth muscle between the 1× and 2×SHH treated groups (p=0.066). Results are quantified in the far right panel. (FIG. 20C) Trichrome stain quantification of collagen showed 26% less collagen in the 1×SHH treated group (p=0.002), and 32% less collagen with 2×SHH treatment (p=0.0001). There was no difference in collagen abundance between the 1× and 2×SHH treated groups (p=0.522).

(FIG. 21A) Apoptotic index was quantified 9 days after CN injury in corpora cavernosal tissue of Sprague Dawley rats that underwent sham surgery or CN crush with one or two SHH PA injections into the corpora cavernosa. Apoptosis index increased 26% at 9 days after CN injury (p=0.014). Two SHH PA injections decreased apoptosis 22% (p=0.021). One SHH PA injection (protein depleted by ~6 days), had apoptotic levels that were not different from untreated 9 day CN crushed rats (p=0.830). Results are quantified in the bottom right panel. (FIG. 21B) Trichrome stain quantification of smooth muscle showed 100% more muscle in the two SHH injection group (p=0.001). With one SHH injection, 110% more smooth muscle was identified compared to MSA controls (p=0.001). There was no difference in smooth muscle preservation between the one and two SHH PA injected penis (p=0.921). Results are quantified in the far right panel. (FIG. 21C) Trichrome stain quantification of collagen showed 24% less collagen in the two SHH injection group (p=0.003), and 21% less in the one SHH PA injection group (p=0.022). The one and two SHH injection groups were not different from each other with regard to collagen preservation (p=0.919).

(FIG. 22A) Apoptotic index was quantified 4 days after CN crush in Sprague Dawley rats that underwent CN crush and SHH or MSA (control) protein was delivered by PA to the penis and PG/CN. Apoptosis decreased 27% with SHH treatment (p=0.0001). Results are quantified in the far right panel. (FIG. 22B) Trichrome stain quantification of penile smooth muscle showed 127% more smooth muscle in SHH treated rats (p=0.0004). Results are quantified in the far right panel. (FIG. 22C) Trichrome stain quantification of collagen showed 30% less collagen in the rats treated with SHH in the penis and PG/CN (n=7) (p=0.0003).

(FIG. 25A) Photos of the pelvic plexus from adult (P115-120) and aged (P200-329) Sprague Dawley rats. The CN is flat and thin in the adult rat with a small, clearly defined MPG. In the aged rat, the CN is thicker and rounder in appearance, with a larger, less well-defined MPG. The vascular supply does not appear diminished with age. (FIG. 25B) Magnified view of MPG treated with SHH protein, shows growing neurites with clearly visible growth cones at the tips and elongating fibers. (FIG. 25C) Neurites were confirmed with GAP43 (growth cones marker). 100-800× magnification.

DETAILED DESCRIPTION

Figure 1A:
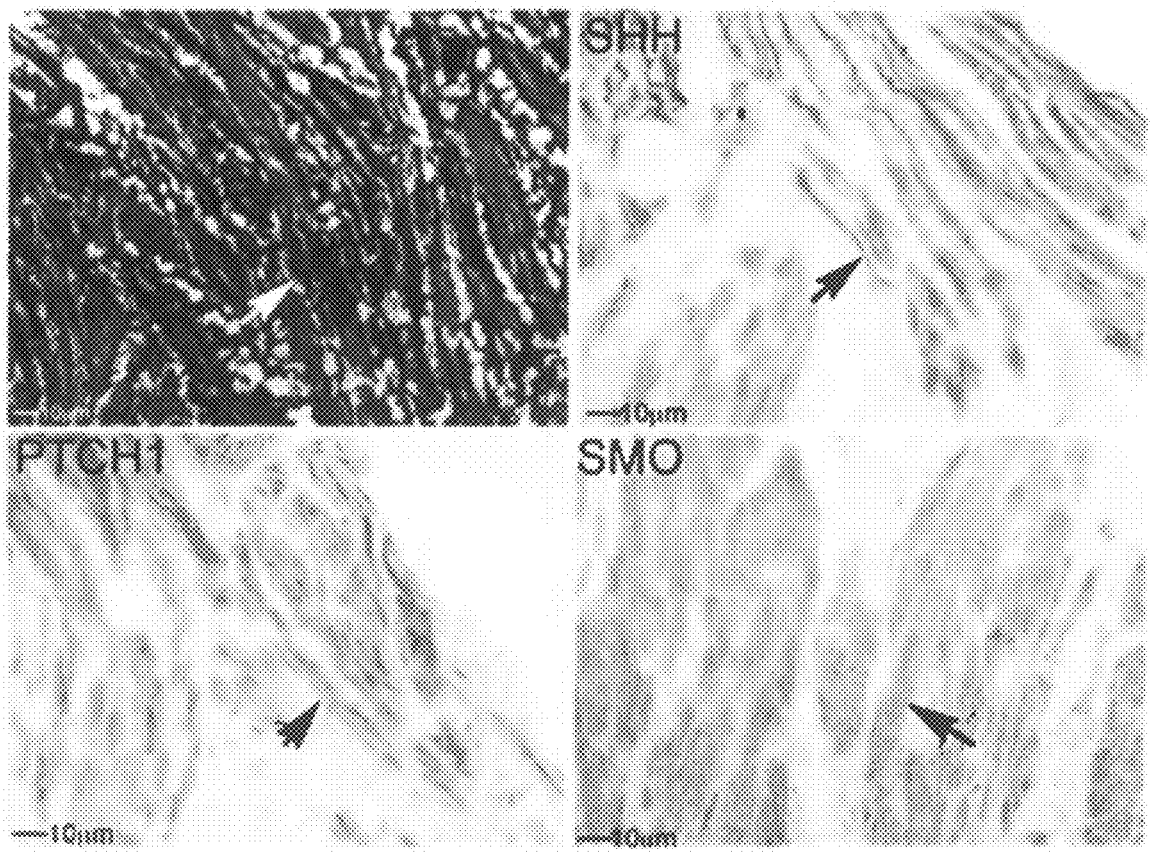
FIGS. 1A-1B show trichrome stain and IHC analysis for SHH pathway in human RS muscle.

Described herein are compositions comprising a sonic hedgehog protein and a delivery vehicle. In some embodiments, the delivery vehicle comprises one or more peptide amphiphiles. The compositions may be used for a variety of methods, including methods of preventing and/or treating stress urinary incontinence, methods of preventing and/or treating erectile dysfunction, methods of preventing smooth muscle apoptosis, and methods of promoting regeneration of tissue in a subject.

1. Definitions

Although any methods and materials similar or equivalent to those described herein can be used in the practice or testing of embodiments described herein, some preferred methods, compositions, and materials are described herein. However, before the present materials and methods are described, it is to be understood that this invention is not limited to the particular molecules, compositions, methodologies or protocols herein described, as these may vary in accordance with routine experimentation and optimization. It is also to be understood that the terminology used in the description is for the purpose of describing the particular versions or embodiments only and is not intended to limit the scope of the embodiments described herein.

Unless otherwise defined, all technical and scientific terms used herein have the same meaning as commonly understood by one of ordinary skill in the art to which this invention belongs. However, in case of conflict, the present specification, including definitions, will control. Accordingly, in the context of the embodiments described herein, the following definitions apply.

As used herein and in the appended claims, the singular forms "a", "an" and "the" include plural reference unless the context clearly dictates otherwise. Thus, for example, reference to "a peptide amphiphile" is a reference to one or more peptide amphiphiles and equivalents thereof known to those skilled in the art, and so forth.

As used herein, the terms "comprise", "include", and linguistic variations thereof denote the presence of recited feature(s), element(s), method step(s), etc. without the exclusion of the presence of additional feature(s), element(s), method step(s), etc. Conversely, the term "consisting of" and linguistic variations thereof, denotes the presence of recited feature(s), element(s), method step(s), etc. and excludes any unrecited feature(s), element(s), method step(s), etc., except for ordinarily-associated impurities. The phrase "consisting essentially of" denotes the recited feature(s), element(s), method step(s), etc. and any additional feature(s), element(s), method step(s), etc. that do not materially affect the basic nature of the composition, system, or method. Many embodiments herein are described using open "comprising" language. Such embodiments encompass multiple closed "consisting of" and/or "consisting essentially of" embodiments, which may alternatively be claimed or described using such language.

The term "amino acid" refers to natural amino acids, unnatural amino acids, and amino acid analogs, all in their D and L stereoisomers, unless otherwise indicated, if their structures allow such stereoisomeric forms.

Natural amino acids include alanine (Ala or A), arginine (Arg or R), asparagine (Asn or N), aspartic acid (Asp or D), cysteine (Cys or C), glutamine (Gln or Q), glutamic acid (Glu or E), glycine (Gly or G), histidine (His or H), isoleucine (Ile or I), leucine (Leu or L), Lysine (Lys or K), methionine (Met or M), phenylalanine (Phe or F), proline (Pro or P), serine (Ser or S), threonine (Thr or T), tryptophan (Trp or W), tyrosine (Tyr or Y) and valine (Val or V).

Unnatural amino acids include, but are not limited to, azetidinecarboxylic acid, 2-aminoadipic acid, 3-aminoadipic acid, beta-alanine, naphthylalanine ("naph"), aminopropionic acid, 2-aminobutyric acid, 4-aminobutyric acid, 6-aminocaproic acid, 2-aminoheptanoic acid, 2-aminoisobutyric acid, 3-aminoisbutyric acid, 2-aminopimelic acid, tertiary-butylglycine ("tBuG"), 2,4-diaminoisobutyric acid, desmosine, 2,2'-diaminopimelic acid, 2,3-diaminopropionic acid, N-ethylglycine, N-ethylasparagine, homoproline ("hPro" or "homoP"), hydroxylysine, allo-hydroxylysine, 3-hydroxyproline ("3Hyp"), 4-hydroxyproline ("4Hyp"), isodesmosine, allo-isoleucine, N-methylalanine ("MeAla" or "Nime"), N-alkylglycine ("NAG") including N-methylglycine, N-methylisoleucine, N-alkylpentylglycine ("NAPG") including N-methylpentylglycine. N-methylvaline, naphthylalanine, norvaline ("Norval"), norleucine ("Norleu"), octylglycine ("OctG"), ornithine ("Orn"), pentylglycine ("pG" or "PGly"), pipecolic acid, thioproline ("ThioP" or "tPro"), homoLysine ("hLys"), and homoArginine ("hArg").

The term "amino acid analog" refers to a natural or unnatural amino acid where one or more of the C-terminal carboxy group, the N-terminal amino group and side-chain bioactive group has been chemically blocked, reversibly or irreversibly, or otherwise modified to another bioactive group. For example, aspartic acid-(beta-methyl ester) is an amino acid analog of aspartic acid; N-ethylglycine is an amino acid analog of glycine; or alanine carboxamide is an amino acid analog of alanine. Other amino acid analogs include methionine sulfoxide, methionine sulfone, S-(carboxymethyl)-cysteine, S-(carboxymethyl)-cysteine sulfoxide and S-(carboxymethyl)-cysteine sulfone.

As used herein, the term "artificial" refers to compositions and systems that are designed or prepared by man and are not naturally occurring. For example, an artificial peptide, peptoid, or nucleic acid is one comprising a non-natural sequence (e.g., a peptide without 100% identity with a naturally-occurring protein or a fragment thereof).

As used herein, a "conservative" amino acid substitution refers to the substitution of an amino acid in a peptide or polypeptide with another amino acid having similar chemical properties, such as size or charge. For purposes of the present disclosure, each of the following eight groups contains amino acids that are conservative substitutions for one another:
1) Alanine (A) and Glycine (G);
2) Aspartic acid (D) and Glutamic acid (E);
3) Asparagine (N) and Glutamine (Q);
4) Arginine (R) and Lysine (K);
5) Isoleucine (I), Leucine (L), Methionine (M), and Valine (V);
6) Phenylalanine (F), Tyrosine (Y), and Tryptophan (W);
7) Serine (S) and Threonine (T); and
8) Cysteine (C) and Methionine (M).

Naturally occurring residues may be divided into classes based on common side chain properties, for example: polar positive (or basic) (histidine (H), lysine (K), and arginine (R)); polar negative (or acidic) (aspartic acid (D), glutamic acid (E)); polar neutral (serine (S), threonine (T), asparagine (N), glutamine (Q)); non-polar aliphatic (alanine (A), valine (V), leucine (L), isoleucine (I), methionine (M)); non-polar aromatic (phenylalanine (F), tyrosine (Y), tryptophan (W)); proline and glycine; and cysteine. As used herein, a "semi-conservative" amino acid substitution refers to the substitution of an amino acid in a peptide or polypeptide with another amino acid within the same class.

In some embodiments, unless otherwise specified, a conservative or semi-conservative amino acid substitution may also encompass non-naturally occurring amino acid residues that have similar chemical properties to the natural residue. These non-natural residues are typically incorporated by chemical peptide synthesis rather than by synthesis in biological systems. These include, but are not limited to, peptidomimetics and other reversed or inverted forms of amino acid moieties. Embodiments herein may, in some embodiments, be limited to natural amino acids, non-natural amino acids, and/or amino acid analogs.

Non-conservative substitutions may involve the exchange of a member of one class for a member from another class.

As used herein, the term "peptide" refers an oligomer to short polymer of amino acids linked together by peptide bonds. In contrast to other amino acid polymers (e.g., proteins, polypeptides, etc.), peptides are of about 50 amino acids or less in length. A peptide may comprise natural amino acids, non-natural amino acids, amino acid analogs, and/or modified amino acids. A peptide may be a subsequence of naturally occurring protein or a non-natural (artificial) sequence.

As used herein, the term "sequence identity" refers to the degree of which two polymer sequences (e.g., peptide, polypeptide, nucleic acid, etc.) have the same sequential composition of monomer subunits. The term "sequence similarity" refers to the degree with which two polymer sequences (e.g., peptide, polypeptide, nucleic acid, etc.) differ only by conservative and/or semi-conservative amino acid substitutions. The "percent sequence identity" (or "percent sequence similarity") is calculated by: (1) comparing two optimally aligned sequences over a window of comparison (e.g., the length of the longer sequence, the length of the shorter sequence, a specified window, etc.), (2) determining the number of positions containing identical (or similar) monomers (e.g., same amino acids occurs in both sequences, similar amino acid occurs in both sequences) to yield the number of matched positions, (3) dividing the number of matched positions by the total number of positions in the comparison window (e.g., the length of the longer sequence, the length of the shorter sequence, a specified window), and (4) multiplying the result by 100 to yield the percent sequence identity or percent sequence similarity. For example, if peptides A and B are both 20 amino acids in length and have identical amino acids at all but 1 position, then peptide A and peptide B have 95% sequence identity. If the amino acids at the non-identical position shared the same biophysical characteristics (e.g., both were acidic), then peptide A and peptide B would have 100% sequence similarity. As another example, if peptide C is 20 amino acids in length and peptide D is 15 amino acids in length, and 14 out of 15 amino acids in peptide D are identical to those of a portion of peptide C, then peptides C and D have 70% sequence identity, but peptide D has 93.3% sequence identity to an optimal comparison window of peptide C. For the purpose of calculating "percent sequence identity" (or "percent sequence similarity") herein, any gaps in aligned sequences are treated as mismatches at that position.

Any polypeptides described herein as having a particular percent sequence identity or similarity (e.g., at least 70%) with a reference sequence ID number, may also be expressed as having a maximum number of substitutions (or terminal deletions) with respect to that reference sequence. For example, a sequence having at least Y % sequence identity (e.g., 90%) with SEQ ID NO:Z (e.g., 100 amino acids) may have up to X substitutions (e.g., 10) relative to SEQ ID NO:Z, and may therefore also be expressed as "having X (e.g., 10) or fewer substitutions relative to SEQ ID NO:Z."

As used herein, the terms "peptide amphiphile" or "PA" are used interchangeably to refer to a molecule that, at a minimum, includes a hydrophobic, non-peptide segment, a structural peptide segment (e.g., β-sheet forming), and a charged peptide segment. The peptide amphiphile may express a net charge at physiological pH, either a net positive or negative net charge, or may be zwitterionic (i.e., carrying both positive and negative charges).

As used herein and in the appended claims, the term "lipophilic moiety" or "hydrophobic moiety" refers to the moiety (e.g., an acyl, alkyl, ether, sulfonamide, or phosphodiestermoiety) disposed on one terminus (e.g., C-terminus, N-terminus) of the peptide amphiphile, and may be herein and elsewhere referred to as the lipophilic or hydrophobic segment or component. The hydrophobic segment should be of a sufficient length to provide amphiphilic behavior and aggregate (or nanosphere or nanofiber) formation in water or another polar solvent system. Accordingly, in the context of the embodiments described herein, the hydrophobic component preferably comprises a single, linear alkyl chain of the formula $C_{8-24}$. In other embodiments, the hydrophobic component comprises a single, linear acyl chain of the formula: $C_{n-1}H_{2n-1}C(O)$— where n=2-25. In some embodiments, a linear acyl chain is the lipophilic group (saturated or unsaturated carbons), palmitic acid. However, other lipophilic groups may be used such as steroids, phospholipids and fluorocarbons.

As used herein, the term "structural peptide" refers to a portion of a peptide amphiphile, typically disposed between the hydrophobic segment and the charged peptide segment. The structural peptide is generally composed of three to ten amino acid residues with non-polar, uncharged side chains (e.g., His (H), Val (V), Ile (I), Leu (L), Ala (A), Phe (F)) selected for their propensity to form hydrogen bonds or other stabilizing interactions (e.g., hydrophobic interactions, van der Waals' interactions, etc.) with structural segments of adjacent structural segments. In some embodiments, nanofibers of peptide amphiphiles having structural peptide segments display linear or 2D structure when examined by microscopy and/or α-helix and/or β-sheet character when examined by circular dichroism (CD). In some embodiments, the structural peptide comprises $V_2A_2$. In other embodiments, the structural peptide comprises $V_3A_3$.

As used herein, the term "beta (β)-sheet-forming peptide segment" refers to a structural peptide segment that has a propensity to display β-sheet-like character (e.g., when analyzed by CD). In some embodiments, amino acids in a beta (β)-sheet-forming peptide segment are selected for their propensity to form a beta-sheet secondary structure. Examples of suitable amino acid residues selected from the twenty naturally occurring amino acids include Met (M), Val (V), Ile (I), Cys (C), Tyr (Y), Phe (F), Gln (Q), Leu (L), Thr (T), Ala (A), and Gly (G) (listed in order of their propensity to form beta sheets). However, non-naturally occurring amino acids of similar beta-sheet forming propensity may also be used. Peptide segments capable of interacting to form beta sheets and/or with a propensity to form beta sheets are understood (See, e.g., Mayo et al. Protein Science (1996), 5:1301-1315; herein incorporated by reference in its entirety).

As used herein, the term "charged peptide segment" refers to a portion of a peptide amphiphile that is rich (e.g., >50%, >75%, etc.) in charged amino acid residues, or amino acid residue that have a net positive or negative charge under physiologic conditions. A charged peptide segment may be acidic (e.g., negatively charged), basic (e.g., positively charged), or zwitterionic (e.g., having both acidic and basic residues). In some embodiments, the charged peptide segment comprises $E_{2-4}$.

As used herein, the terms "carboxy-rich peptide segment," "acidic peptide segment," and "negatively-charged peptide segment" refer to a peptide sequence of a peptide amphiphile that comprises one or more amino acid residues that have side chains displaying carboxylic acid side chains (e.g., Glu (E), Asp (D), or non-natural amino acids). A carboxy-rich peptide segment may optionally contain one or more additional (e.g., non-acidic) amino acid residues. Non-natural amino acid residues, or peptidomimetics with acidic side chains could be used, as will be evident to one ordinarily skilled in the art. There may be from about 2 to about 7 amino acids, and or about 3 or 4 amino acids in this segment.

As used herein, the terms "amino-rich peptide segment", "basic peptide segment," and "positively-charged peptide segment" refer to a peptide sequence of a peptide amphiphile that comprises one or more amino acid residues that have side chains displaying positively-charged acid side chains (e.g., Arg (R), Lys (K), His (H), or non-natural amino acids, or peptidomimetics). A basic peptide segment may optionally contain one or more additional (e.g., non-basic) amino acid residues. Non-natural amino acid residues with basic side chains could be used, as will be evident to one ordinarily skilled in the art. There may be from about 2 to about 7 amino acids, and or about 3 or 4 amino acids in this segment.

As used herein, the term "biocompatible" refers to materials and agents that are not toxic to cells or organisms. In some embodiments, a substance is considered to be "biocompatible" if its addition to cells in vitro results in less than or equal to approximately 10% cell death, usually less than 5%, more usually less than 1%.

As used herein, the term "nanofiber" refers to an elongated or threadlike filament (e.g., having a significantly greater length dimension that width or diameter) with a diameter typically less than 100 nanometers.

As used herein, "biodegradable" as used to describe the polymers, hydrogels, and/or wound dressings herein refers to compositions degraded or otherwise "broken down" under exposure to physiological conditions. In some embodiments, a biodegradable substance is a broken down by cellular machinery, enzymatic degradation, chemical processes, hydrolysis, etc. In some embodiments, a wound dressing or coating comprises hydrolyzable ester linkages that provide the biodegradability.

As used herein, the phrase "physiological conditions" relates to the range of chemical (e.g., pH, ionic strength) and biochemical (e.g., enzyme concentrations) conditions likely to be encountered in the intracellular and extracellular fluids of tissues. For most tissues, the physiological pH ranges from about 7.0 to 7.4. An exception is in the acidic environment in the vagina, which has a pH between 4.0 and 4.5.

As used herein, the term "supramolecular" (e.g., "supramolecular complex," "supramolecular interactions," "supramolecular fiber," "supramolecular polymer," etc.) refers to the non-covalent interactions between molecules (e.g., polymers, macromolecules, etc.) and the multicomponent assemblies, complexes, systems, and/or fibers that form as a result.

As used herein, the terms "self-assemble" and "self-assembly" refer to formation of a discrete, non-random, aggregate structure from component parts; said assembly occurring spontaneously through random movements of the components (e.g. molecules) due only to the inherent chemical or structural properties and attractive forces of those components As used herein, the terms "prevent," "prevention," and preventing" refer to reducing the likelihood of a particular condition or disease state (e.g., stress urinary incontinence, erectile dysfunction) from occurring in a subject not presently experiencing or afflicted with the condition or disease state. The terms do not necessarily indicate complete or absolute prevention. For example "preventing stress urinary incontinence" refers to reducing the likelihood of SUI occurring in a subject not presently experiencing or diagnosed with SUI. In order to "prevent stress urinary incontinence" a composition or method need only reduce the likelihood of SUI, not completely block any possibility thereof "Prevention," encompasses any administration or application of a therapeutic or technique to reduce the likelihood of a disease developing (e.g., in a mammal, including a human). Such a likelihood may be assessed for a population or for an individual.

As used herein, the terms "treat," "treatment," and "treating" refer to reducing the amount or severity of a particular condition, disease state (e.g., stress urinary incontinence, erectile dysfunction), or symptoms thereof, in a subject presently experiencing or afflicted with the condition or disease state. The terms do not necessarily indicate complete treatment (e.g., total elimination of the condition, disease, or symptoms thereof). "Treatment," encompasses any administration or application of a therapeutic or technique for a disease (e.g., in a mammal, including a human), and includes inhibiting the disease, arresting its development, relieving the disease, causing regression, or restoring or repairing a lost, missing, or defective function; or stimulating an inefficient process.

As used herein, the term "administration" refers to any suitable method of providing a composition described herein to a subject. Administration may be by any suitable method. For example, administration may occur by directly applying the composition to a tissue of the subject. For example, the composition may be placed directly on top of the tissue of the subject. Suitable routes of administrating the composition described herein include, without limitation: topical, subcutaneous, transdermal, intradermal, intralesional, intraarticular, intraperitoneal, intravesical, transmucosal, gingival, intradental, intracochlear, transtympanic, intraorgan, epidural, intrathecal, intramuscular, intravenous, intravascular, intraosseus, periocular, intratumoral, intracerebral, and intracerebroventricular administration. In some embodiments, the PA compositions are administered parenterally. In some embodiments, parenteral administration is by intrathecal administration, intracerebroventricular administration, or intraparenchymal administration. The PA compositions herein can be administered as the sole active agent or in combination with other pharmaceutical agents such as other agents used in the treatment of erectile dysfunction and/or stress urinary incontinence in a subject.

Administration "at the time of prostatectomy" may include any suitable time over the course of the prostatectomy while the tissue of the subject is exposed. For example, administration at the time of prostatectomy may indicate that administration occurs immediately prior to the prostatectomy, during the prostatectomy, or immediately after the prostatectomy, so long as the tissue is still exposed.

Administration "before a prostatectomy" or "prior to a prostatectomy" as used interchangeably herein may include administration at any suitable time point before the prostatectomy. For example, the composition may be administered one year, six months, three months, one month, two weeks, one week, three days, one day, or immediately before prostatectomy.

Administration "following" or "after" an event, such as a prostatectomy or other injury, may comprise administering the composition to the subject at any suitable time point following the prostatectomy or other injury. For example, administration may occur one day, two days, three days, four days, five days, six days, seven days, eight days, nine days, ten days, two weeks, or more than two weeks following the prostatectomy or other injury.

As used herein, the terms "co-administration" and "co-administering" refer to the administration of at least two agent(s) or therapies to a subject (e.g., a composition disclosed herein and one or more therapeutic agents). In some embodiments, the co-administration of two or more agents or therapies is concurrent. In other embodiments, a first agent/therapy is administered prior to a second agent/therapy. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent(s), and/or when co-administration of two or more agents results in sensitization of a subject to beneficial effects of one of the agents via co-administration of the other agent.

The term "corpora cavernosa" as used herein refers to the mass of erectile tissue forming the bulk of the penis, or the mass of erectile tissue forming the bulk of the clitoris. When used in reference to a male subject, the "corpora cavernosa" is understood to refer to the corpora cavernosa of the penis. When used in reference to female subjects, the "corpora cavernosa" is understood to refer to the corpora cavernosa of the clitoris.

As used herein, the term "pelvic ganglia" refers to a region of the body that supply innervation to all of the pelvic viscera. The pelvic ganglia in the male provide innervation to the penis, bladder, colorectum, internal reproductive organs, and anal accessory muscles. In the female, the pelvic ganglia provide innervation to the uterus, vagina, bladder, colon, and anal accessory muscles. The term pelvic ganglia encompass the cavernous nerve, hypogastric nerve, pelvic nerve, and ancillary nerve.

As used herein, the term "prostatectomy" refers to any procedure wherein at least a portion of the prostate is removed. The term "prostatectomy" includes procedures wherein a portion of the prostate is removed (e.g. a "simple prostatectomy") and procedures wherein the entire prostate is removed. Procedures wherein the entire prostate is removed are also referred to herein as a "radical prostatectomy". The term "prostatectomy" also includes procedures wherein additional tissue is removed. For example, the term "prostatectomy" also includes a "cystoprostatectomy" wherein at least a portion of the prostate and the bladder are removed. The term "prostatectomy" further includes a "radical cystoprostatectomy" wherein the entire prostate and the bladder are removed.

The term "smooth muscle" as used herein refers to involuntary muscle tissue (i.e., muscle tissue not under voluntary control) in which the contractive fibrils are not highly ordered.

The term "striated muscle" as used herein refers to muscle tissue in which the contractile fibers are aligned in parallel bundles. In some embodiments, the term "striated muscle" may refer to the striated muscle of the rhabdosphincter.

The terms "sonic hedgehog protein" and "SHH" are used interchangeably herein to refer to all forms of the sonic hedgehog protein. Suitable forms of sonic hedgehog protein include recombinant protein, modified protein, and active forms of the protein.

The terms "stress urinary incontinence" or "SUI" are used interchangeably herein to refer to a condition in which unintentional loss of urine occurs when pressure (e.g. stress) is placed on the bladder. Stress incontinence may occur when physical movement or activity such as coughing, sneezing, running, or heavy lifting puts pressure on the bladder. "Stress incontinence" differs from "urge incontinence", wherein unintentional loss of urine is caused by bladder muscle contraction.

As used herein, the terms "subject" and "patient" refer to any animal, such as a dog, cat, bird, livestock, and particularly a mammal, preferably a human. In some embodiments, the subject is a male. In other embodiments, the subject is a female. When referring to methods relating to male anatomy, it is understood that the subject is a male. In some embodiments, the subject is an "aged" subject. An "aged" subject in reference to a human subject refers to a subject over the age of 50 years old. For example, an aged subject may be over the age of 50, over the age of 55, over the age of 60, over the age of 65, over the age of 70, over the age or 75, or over the age of 80 years old. The subject may be diabetic or at risk of developing diabetes. The subject may have erectile dysfunction and/or urinary incontinence. The subject may display any number of the above characteristics. For example, the subject may be an aged subject that is also diabetic, or an aged subject that also has erectile dysfunction.

2. Compositions

In some embodiments, provided herein are compositions comprising a sonic hedgehog protein and a delivery vehicle. In some embodiments, the delivery vehicle comprises one or more peptide amphiphiles.

a. Sonic Hedgehog Protein

The sonic hedgehog protein may be any suitable form of sonic hedgehog protein. The sonic hedgehog protein may be an active form of SHH, a recombinant SHH protein, or a modified form of SHH. The sonic hedgehog protein be from any suitable mammalian source. For example, the sonic hedgehog protein may be a recombinant mouse sonic hedgehog protein. In some embodiments, the SHH may comprise the amino acid sequence MLSLFPSPGPGSSRCKDKLNALAISVMNQWPGVKLRVTEGWDEDGHHSEESLHYEGRAVDITTSDRDRSKYGMLARLAVEAGEDWVYYESKAHIHCSVKAVQSDEKSVESEPEAPGTAAPLAV (SEQ ID NO: 1). In some embodiments, the SHH may comprise an amino acid sequence having at least 70% sequence identity to SEQ ID NO: 1. For example, the SHH may comprise an amino acid sequence having at least 70%, at least 75%, at least 80%, at least 85%, at least 90%, at least 95%, or at least 99% identity with SEQ ID NO: 1. In some embodiments, the SHH may comprise the amino acid sequence CGPGRGFGKRRHPKKLTPLAYKQFIPNVAEKTLGASGRYEGKITRNSERFKELTPNYNPDIIFKDEENTGADRLMTQRCKDKLNALAISVMNQWPGVKLRVTEGWDEDGHHSEESLHYEGRAVDITTSDRDRSKYGMLARLAVEAGFDWVYYESKAHIHCSVKAENSVAAKSGGHHHHHH (SEQ ID NO: 2). In some embodiments, the SHH may comprise an amino acid sequence having at least 70% sequence identity to SEQ ID NO: 2. For example, the SHH may comprise an amino acid sequence having at least 70%, at least 75%, at least 80%, at least 85%, at least 90%, at least 95%, or at least 99% identity with SEQ ID NO: 2. In some embodiments, the sonic hedgehog protein may comprise the amino acid sequence MLLLLARCFLVILASSLLVCPGLACGPGRGFGKRRHPKKLTPLAYKQFIPNVAEKTLGASGRYEGKITRNSERFKELTPNYNPDIIFKDEENTGADRLMTQRCKDKLNALAISVMNQWPGVKLRVTEGWDEDGHHSEESLHYEGRAVDITTSDRDRSKYGMLARLAVEAGEDWVYYESKAHIHCSVKAENSVAAKSGGCFPGSATVHLEQGGTKLVKDLRPGDRVLAADDQGRLLYSDFLTELDRDEGAKKVEYVIETLEPRERLLLTAAHLLEVAPHNDSGPTPGPSALFASRVRPGQRVYVVAERGGDRRLLPAAVHSVTLREEEAGAYAPLTAHGTILINRVLASCYAVIEEHSWAHRAFAPERLAHALLAALAPARTDGGGGGSIPAAQSATEARGAEPTAGIHWYSQLLYHIGTWLLDSETMHPLGMAVKSS (SEQ ID NO: 3). In some embodiments, the SHH may comprise an amino acid sequence having at least 70% sequence identity to SEQ ID NO: 3. For example, the SHH may comprise an amino acid sequence having at least 70%, at least 75%, at least 80%, at least 85%, at least 90%, at least 95%, or at least 99% identity with SEQ ID NO: 3.

The sonic hedgehog protein may be a modified form of the protein. For example, the sonic hedgehog protein may be a modified form of the active protein. Examples of suitable modifications include cholesterol modifications, lipid modifications, pegylation of the protein, and the like.

b. Delivery Vehicle

The composition further comprises a delivery vehicle. Suitable delivery vehicles are capable of local, extended release of the sonic hedgehog protein, easily deliverable in vivo (such as at the time of prostatectomy), and biodegradable. In some embodiments, the delivery vehicle comprises a hydrogel. For example, the delivery vehicle may comprise a hyaluronic acid based hydrogel, a PLGA hydrogel, or other suitable hydrogels.

In particular embodiments, the delivery vehicle comprises one or more peptide amphiphiles. The peptide amphiphile molecules and compositions of the embodiments described herein may be synthesized using preparatory techniques well-known to those skilled in the art, preferably, by standard solid-phase peptide synthesis, with the addition of a fatty acid in place of a standard amino acid at the N-terminus (or C-terminus) of the peptide, in order to create the lipophilic segment. In some embodiments, alignment of nanofibers is performed via techniques not previously disclosed or used in the art (e.g., extrusion through a mesh screen). Synthesis typically starts from the C-terminus, to which amino acids are sequentially added. Amino acids may be sequentially added using a Rink amide resin (resulting in an —NH$_2$ group at the C-terminus of the peptide after cleavage from the resin). Amino acids may be sequentially added using a Wang resin (resulting in an —OH group at the C-terminus). Accordingly, some embodiments described herein encompass peptide amphiphiles having a C-terminal moiety that may be selected from the group consisting of —H, —OH, —COOH, —CONH$_2$, and —NH$_2$. In some embodiments, the C-terminal moiety may be aspartic acid.

In some embodiments, peptide amphiphiles comprise a hydrophobic segment (i.e. a hydrophobic tail) linked to a peptide. In some embodiments, the peptide comprises a structural segment (e.g., hydrogen-bond-forming segment, beta-sheet-forming segment, etc.), and a charged segment (e.g., acidic segment, basic segment, zwitterionic segment, etc.). In some embodiments, the peptide further comprises linker or spacer segments for adding solubility, flexibility, distance between segments, etc. In some embodiments, peptide amphiphiles comprise a spacer segment (e.g., peptide and/or non-peptide spacer) at the opposite terminus of the peptide from the hydrophobic segment. In some embodiments, the spacer segment comprises peptide and/or non-peptide elements. In some embodiments, the spacer segment comprises one or more bioactive groups (e.g., alkene, alkyne, azide, thiol, etc.). In some embodiments, various segments may be connected by linker segments (e.g., peptide (e.g., GG) or non-peptide (e.g., alkyl, OEG, PEG, etc.) linkers).

The lipophilic or hydrophobic segment may be incorporated at the N- or C-terminus of the peptide after the last amino acid coupling and is composed of a fatty acid or other acid that is linked to the N- or C-terminal amino acid through an acyl bond. In aqueous solutions, PA molecules may self-assemble (e.g., into cylindrical micelles (a.k.a., nanofibers)) that bury the lipophilic segment in their core. The structural peptide may undergo intermolecular hydrogen bonding to form beta sheets that orient parallel to the long axis of the micelle.

In some embodiments, compositions described herein comprise PA building blocks that in turn comprise a hydrophobic segment and a peptide segment. In certain embodiments, a hydrophobic (e.g., hydrocarbon and/or alkyl/alkenyl/alkynyl tail, or steroid such as cholesterol) segment of sufficient length (e.g., 2 carbons, 3 carbons, 4 carbons, 5 carbons, 6 carbons, 7 carbons, 8 carbons, 9 carbons, 10 carbons, 11 carbons, 12 carbons, 13 carbons, 14 carbons, 15 carbons, 16 carbons, 17 carbons, 18 carbons, 19 carbons, 20 carbons, 21 carbons, 22 carbons, 23 carbons, 24 carbons, 25 carbons, 26 carbons, 27 carbons, 28 carbons, 29 carbons, 30 carbons or more, or any ranges there between.) is covalently coupled to peptide segment (e.g., a peptide comprising a segment having a preference for beta-strand conformations or other supramolecular interactions) to yield a peptide amphiphile molecule. In some embodiments, a plurality of such PAs will self-assemble in water (or aqueous solution) into a nanostructure (e.g., nanofiber). In various embodiments, the relative lengths of the peptide segment and hydrophobic segment result in differing PA molecular shape and nanostructural architecture. For example, a broader peptide segment and narrower hydrophobic segment results in a generally conical molecular shape that has an effect on the assembly of PAs (See, e.g., J. N. Israelachvili Intermolecular and surface forces; 2nd ed.; Academic: London San Diego, 1992; herein incorporated by reference in its entirety). Other molecular shapes have similar effects on assembly and nanostructural architecture.

In some embodiments, to induce self-assembly of an aqueous solution of peptide amphiphiles, the pH of the solution may be changed (raised or lowered) or multivalent ions, such as calcium, or charged polymers or other macromolecules may be added to the solution.

In some embodiments, the hydrophobic segment is a non-peptide segment (e.g., alkyl/alkenyl/alkynyl group). In some embodiments, the hydrophobic segment comprises an alkyl chain (e.g., saturated) of 4-25 carbons (e.g., 4, 5, 6, 7, 8, 9, 10, 11, 12, 13, 14, 15, 16, 17, 18, 19, 20, 21, 22, 23, 24, 25), fluorinated segments, fluorinated alkyl tails, heterocyclic rings, aromatic segments, pi-conjugated segments, cycloalkyls, oligothiophenes etc. In some embodiments, the hydrophobic segment comprises an acyl/ether chain (e.g., saturated) of 2-30 carbons (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30). In particular embodiments, the hydrophobic segment comprise an alkyl chain comprising 8-24 carbons ($C_{8-24}$). For example, the hydrophobic segment may comprise an alkyl chain comprising 16 carbons ($C_{16}$).

In some embodiments, PAs comprise one or more peptide segments. Peptide segment may comprise natural amino acids, modified amino acids, unnatural amino acids, amino acid analogs, peptidomimetics, or combinations thereof. In some embodiments, peptide segment comprises at least 50% sequence identity or similarity (e.g., conservative or semi-conservative) to one or more of the peptide sequences described herein.

In some embodiments, peptide amphiphiles comprise a charged peptide segment. The charged segment may be acidic, basic, or zwitterionic.

In some embodiments, peptide amphiphiles comprise an acidic peptide segment. For example, in some embodiments, the acidic peptide comprises one or more (e.g., 1, 2, 3, 4, 5, 6, 7, or more) acidic residues (D and/or E) in sequence. In some embodiments, the acidic peptide segment comprises up to 7 residues in length and comprises at least 50% acidic residues. In some embodiments, an acidic peptide segment comprises $(Xa)_{1-7}$, wherein each Xa is independently D or E. In some embodiments, an acidic peptide segment comprises $E_{2-4}$. EE. In some embodiments, an acidic peptide segment comprises EEE. In other embodiments, an acidic peptide segment comprises EEEE.

In some embodiments, peptide amphiphiles comprise a basic peptide segment. For example, in some embodiments, the acidic peptide comprises one or more (e.g., 1, 2, 3, 4, 5, 6, 7, or more) basic residues (R, H, and/or K) in sequence. In some embodiments, the basic peptide segment comprises up to 7 residues in length and comprises at least 50% basic residues. In some embodiments, an acidic peptide segment comprises $(Xb)_{1-7}$, wherein each Xb is independently R, H, and/or K.

In some embodiments, peptide amphiphiles comprises a structural and/or beta-sheet-forming segment. In some embodiments, the structural segment is rich in one or more of H, I, L, F, V, G, and A residues. In some embodiments, the structural and/or beta-sheet-forming segment comprises an alanine- and valine-rich peptide segment (e.g., VVAA, VVVAAA, AAVV, AAAVVV, or other combinations of V and A residues, etc.). In some embodiments, the structural and/or beta sheet peptide comprises 4 or more consecutive A and/or V residues, or conservative or semi-conservative substitutions thereto. In some embodiments, the structural segment comprises $V_2A_2$. In some embodiments, the structural segment comprises $V_3A_3$.

In some embodiments, peptide amphiphiles comprise a non-peptide spacer or linker segment. In some embodiments, the non-peptide spacer or linker segment is located at the opposite terminus of the peptide from the hydrophobic segment. In some embodiments, the spacer or linker segment provides a reactive group (e.g., alkene, alkyne, azide, thiol, maleimide etc.) for functionalization of the PA. In some embodiments, the spacer or linker is a substantially linear chain of $CH_2$, O, $(CH_2)_2O$, $O(CH_2)_2$, NH, and C=O groups (e.g., $CH_2(O(CH_2)_2)_2NH$, $CH_2(O(CH_2)_2)_2NHCO$ $(CH_2)_2CCH$, etc.). In some embodiments, a spacer or linker further comprises additional bioactive groups, substituents, branches, etc. In some embodiments, the linker segment is a single glycine (G) residue.

Suitable peptide amphiphiles for use in the materials herein, as well as methods of preparation of PAs and related materials, amino acid sequences for use in PAs, and materials that find use with PAs, are described in the following patents: U.S. Pat. Nos. 9,044,514; 9,040,626; 9,011,914; 8,772,228; 8,748,569 8,580,923; 8,546,338; 8,512,693; 8,450,271; 8,236,800; 8,138,140; 8,124,583; 8,114,835; 8,114,834; 8,080,262; 8,076,295; 8,063,014; 7,851,445; 7,838,491; 7,745,708; 7,683,025; 7,554,021; 7,544,661; 7,534,761; 7,491,690; 7,452,679; 7,371,719; 7,030,167; all of which are herein incorporated by reference in their entireties.

The characteristics (e.g., shape, rigidity, hydrophilicity, etc.) of a PA supramolecular structure depend upon the identity of the components of a peptide amphiphile (e.g., hydrophobic segment, structural segment, charged segment, etc.). For example, nanofibers, nanospheres, intermediate shapes, and other supramolecular structures are achieved by adjusting the identity of the PA component parts. In some embodiments, characteristics of supramolecular nanostructures of PAs are altered by post-assembly manipulation (e.g., heating/cooling, stretching, etc.).

In some embodiments, a peptide amphiphile comprises: (a) a hydrophobic tail comprising an alkyl chain of 8-24 carbons; (b) a structural segment (e.g., comprising VVAA or VVVAAA); and (c) a charged segment (e.g., comprising EE, EEE, EEEE, etc.). In some embodiments, a peptide amphiphile comprises $C_{16}$—$V_3A_3E_3$-COOH. In some embodiments, a peptide amphiphile comprises $C_{16}$—$V_2A_2E_2$-$NH_2$. Any PAs within the scope described herein, comprising the components described herein, or within the skill of one in the field, may find use herein.

In some embodiments, the PA nanofiber described herein exhibit a small cross-sectional diameter (e.g., <25 nm, <20 nm, <15 nm, about 10 nm, etc.).

In some embodiments, the peptide amphiphile may be covalently coupled to the sonic hedgehog protein. Covalent coupling may occur upon combining the peptide amphiphile and the sonic hedgehog protein. In some embodiments, the peptide amphiphile and the sonic hedgehog protein may be combined immediately prior to use in a subject. For example, the peptide amphiphile and the sonic hedgehog protein may be combined in a suitable container (a petri dish, a glass slide, etc.) immediately prior to use in a subject.

The composition may comprise any suitable amounts of peptide amphiphile and sonic hedgehog protein in any desired ratio. In some embodiments, the composition may comprise a ratio of sonic hedgehog protein:peptide amphiphile of about 1:1. In other embodiments, the composition may comprise a ratio of sonic hedgehog protein:peptide amphiphile of about 2:1. For example, the composition may comprise a ratio of sonic hedgehog protein:peptide amphiphile of about 2:1, about 1.9:1 about 1.8:1, about 1.7:1, about 1.6:1, about 1.5:1, about 1.4:1, about 1.3:1, about 1.2:1, about 1.1:1, or about 1:1. In some embodiments, the composition may comprise a ratio of sonic hedgehog protein:peptide amphiphile of more than 2:1. For example, suitable ratios include 3:1, 4:1, 5:1, and the like.

In particular embodiments, the composition may additionally comprise a suitable salt. For example, the peptide amphiphile, the sonic hedgehog protein, and a suitable salt may be combined immediately prior to use in the subject. In general, suitable salts will shield the charge on the charged portion of the delivery vehicle (such as the peptide amphiphile). Suitable salts include, for example, calcium salts, sodium salts, magnesium salts, and the like. For example, a suitable salt may be calcium chloride. In particular embodiments, the peptide amphiphile, sonic hedgehog protein, and calcium chloride are combined immediately prior to use in a subject. In some embodiments, the concentration of the salt may be about 200 nM to about 100 mM. For example, the concentration of the salt may be about 200 nM to about 100 mM, about 500 nM to about 90 mM, about 1 µM to about 80 mM, about 10 µM to about 70 mM, about 100 µM to about 60 mM, about 500 µM to about 50 mM, about 750 µM to about 40 mM, about 1 mM to about 30 mM, about 2 mM to about 20 mM, or about 10 mM. In some embodiments, the composition may comprise 20 mM calcium chloride.

3. Methods of Use

The compositions comprising a sonic hedgehog protein and one or more peptide amphiphiles may be used in a variety of methods.

a. Stress Urinary Incontinence

In some embodiments, compositions may be used in a method of treating and/or preventing stress urinary incontinence in a subject. The methods may comprise administering the composition to the subject by applying to one or more of the pelvic ganglia, hypogastric nerve, pelvic nerve, and the rhabdosphincter of the subject. For example, the composition may be directly applied to any one of the hypogastric nerve, pelvic nerve, and the rhabdosphincter of the subject. Alternatively, the composition may be applied to any combination of the hypogastric nerve, the pelvic nerve, and the rhabdosphincter of the subject. The compositions may be administered to the subject at any suitable time point at any suitable frequency and duration to achieve the desired result. For example, the composition may be administered once to the subject. Alternatively, the composition may be administered more than once to the subject.

In some embodiments, the compositions may be used in a method of preventing stress urinary incontinence in a subject. In particular embodiments, the composition may be administered to the subject to prevent stress urinary incontinence in the subject that may otherwise develop as a result of a prostatectomy. For example, the composition may be administered to the subject prior to or at the time of a prostatectomy. For example, the composition may be administered to the subject prior to a prostatectomy to prevent stress urinary incontinence in the subject. Alternatively or in combination, the composition may be administered to the subject at the time of prostatectomy to prevent stress urinary incontinence in the subject. Alternatively or in combination, the composition may be administered to the subject following a prostatectomy to prevent stress urinary incontinence in the subject.

In other embodiments, the compositions may be used in a method of preventing stress urinary incontinence in a subject that may otherwise occur for reasons other than a prostatectomy. For example, the compositions may be used in a method of preventing stress urinary incontinence in a subject that may otherwise occur as a result of aging, diabetes, or other injury to the subject. For example, the compositions may be used in a method of preventing stress urinary incontinence in a subject following damage to one or more of the rhabdosphincter, pelvic ganglia, hypogastric nerve, and pelvic nerve of the subject. For example, the compositions may be administered to the subject following injury to one or more of the rhabdosphincter, pelvic ganglia, hypogastric nerve, and pelvic nerve of the subject. As another example, the composition may be administered to an aged subject, such as a subject over the age of 50, to prevent stress urinary incontinence in the subject. Alternatively, the composition may be administered to a subject diagnosed with or at risk of developing diabetes to prevent stress urinary incontinence in the subject.

In other embodiments, the compositions may be used in methods of treating stress urinary incontinence in a subject. In accordance with such embodiments, the method of treating stress urinary incontinence in a subject comprise administering to the subject a composition as described herein. The composition may be administered at any suitable time point, for any suitable duration, to achieve the desired result. For example, the composition may be administered once to the subject. Alternatively, the composition may be administered more than once to the subject. In some embodiments, the compositions may be used in methods of treating stress urinary incontinence caused by prostatectomy in a subject. In other embodiments, the compositions may be used in methods of treating stress urinary incontinence that develops in the subject as a result of aging, diabetes, or other injury to the subject, such as injury to one or more of the rhabdosphincter, pelvic ganglia, hypogastric nerve, and pelvic nerve of the subject.

b. Erectile Dysfunction

In some embodiments, the compositions provided herein may be used in methods of treating and/or preventing erectile dysfunction in a subject. The method may comprise administering the composition to the subject by applying to one or more of the corpora cavernosa (of the penis), the pelvic ganglia, and the cavernous nerve of the subject. The composition may be applied to any combination of the corpora cavernosa, the pelvic ganglia, and the cavernous nerve of the subject. For example, the composition may be applied to the corpora cavernosa and the cavernous nerve of the subject. Alternatively, the composition may be applied to only one of the corpora cavernosa, the pelvic ganglia, or the cavernous nerve of the subject. For example, the composition may be applied only to the corpora cavernosa of the subject. The compositions may be administered to the subject at any suitable time point at any suitable frequency and duration to achieve the desired result. For example, the composition may be administered once to the subject. Alternatively, the composition may be administered more than once to the subject. In particular embodiments, the composition may be administered by two or more applications to the corpora cavernosa of the subject.

In some embodiments, the compositions may be used in methods of preventing erectile dysfunction in the subject. For example, the compositions may be used in methods of preventing erectile dysfunction in a subject following injury to the subject. For example, the compositions may be used in methods of preventing erectile dysfunction following one or more of crush injury to the cavernous nerve, tension injury of the pelvic ganglia, and injury to the smooth muscle tissue of the subject. For example, the compositions may be used in methods of preventing erectile dysfunction in a subject following crush injury to the cavernous nerve or pelvic ganglia tension injury, such as that which may occur during prostatectomy. The compositions may be administered to the subject at any suitable time point after injury to the subject, at any suitable duration and frequency to achieve the desired result.

In some embodiments, the compositions may administered to the subject before and/or during and/or after prostatectomy to prevent erectile dysfunction in the subject. For example, the composition may be administered to the subject before the prostatectomy. Alternatively or in combination, the composition may be administered to the subject during the prostatectomy. Alternatively or in combination, the composition may be administered to the subject following a prostatectomy.

In some embodiments, the compositions may be administered to the subject to prevent erectile dysfunction that may otherwise develop as a result of aging and/or diabetes. For example, the compositions may be administered to an aged subject to prevent erectile dysfunction. As another example, the compositions may be administered to a patient diagnosed with or at risk of developing diabetes. In some embodiments, the subject may be aged and diagnosed with or at risk of developing diabetes.

In other embodiments, the compositions may be used in methods of treating erectile dysfunction in the subject. For example, the compositions may be used in methods of treating erectile dysfunction in a subject following injury to the subject. For example, the compositions may be used in methods of treating erectile dysfunction following one or more of crush injury to the cavernous nerve, tension injury of the pelvic ganglia, and injury to the smooth muscle tissue of the subject. For example, the compositions may be used in methods of treating erectile dysfunction in a subject following crush injury to the cavernous nerve, such as that which may occur during prostatectomy. The compositions may be administered to the subject at any suitable time point after injury to the subject, at any suitable duration and frequency to achieve the desired result.

In some embodiments, the compositions may be administered to the subject to treat erectile dysfunction that has developed independently of injury to the subject. For example, the compositions may be administered to the subject to treat erectile dysfunction that has developed in the subject a result of aging and/or diabetes. For example, the compositions may be administered to an aged subject to treat erectile dysfunction in the subject. As another example, the compositions may be administered to a patient diagnosed with or at risk of developing diabetes that also has erectile dysfunction. In some embodiments, the subject may be aged and diagnosed with or at risk of developing diabetes.

c. Penile Smooth Muscle Apoptosis

In some embodiments, the compositions provided herein may be used in methods of preventing penile smooth muscle apoptosis in a subject. Penile smooth muscle apoptosis initiates a remodeling process in the corpora cavernosa of the penis, leading to a fibrotic penis that can no longer respond to normal neurotransmitter signaling mechanisms. Accordingly, methods of preventing penile smooth muscle apoptosis also refer to the methods of preventing penile remodeling in a subject. In some embodiments, preventing penile smooth muscle apoptosis may also prevent erectile dysfunction in the subject.

The method may comprise administering the composition to the subject by applying to one or more of the corpora cavernosa (of the penis), the pelvic ganglia, and the cavernous nerve of the subject. The composition may be applied to any combination of the corpora cavernosa, the pelvic ganglia, and the cavernous nerve of the subject. For example, the composition may be applied to the corpora cavernosa and the cavernous nerve of the subject. Alternatively, the composition may be applied to only one of the corpora cavernosa, the pelvic ganglia, or the cavernous nerve of the subject. For example, the composition may be applied only to the corpora cavernosa of the subject. The compositions may be administered to the subject at any suitable time point at any suitable frequency and duration to achieve the desired result. For example, the composition may be administered once to the subject. Alternatively, the composition may be administered more than once to the subject. In particular embodiments, the composition may be administered by two or more applications to the corpora cavernosa of the subject.

In some embodiments, the compositions may be used in methods of preventing penile smooth muscle apoptosis in a subject following injury to the subject. For example, the compositions may be used in methods of preventing penile smooth muscle apoptosis following one or more of crush injury to the cavernous nerve, tension injury of the pelvic ganglia, and injury to the smooth muscle tissue of the subject. For example, the compositions may be used in methods of preventing penile smooth muscle apoptosis in a subject following crush injury to the cavernous nerve, such as that which may occur during prostatectomy. The compositions may be administered to the subject at any suitable time point after injury to the subject, for any suitable duration and frequency to achieve the desired result.

In some embodiments, the compositions may administered to the subject before and/or during and/or after prostatectomy to prevent penile smooth muscle apoptosis in the subject. For example, the composition may be administered to the subject before the prostatectomy. Alternatively or in combination, the composition may be administered to the subject during the prostatectomy. Alternatively or in combination, the composition may be administered to the subject following a prostatectomy.

d. Tissue Regeneration

In some embodiments, the compositions provided herein may be used in methods of promoting regeneration of one or more tissues in a subject. The composition may promote regeneration of one or more tissues selected from penile smooth muscle tissue, striated muscle tissue, cavernous nerve tissue, pelvic ganglia, hypogastric nerve tissue, and pelvic nerve tissue. Striated muscle tissue may be rhabdosphincter tissue.

Promoting regeneration of one or more tissues may enable treatment and/or prevention of stress urinary incontinence and/or erectile dysfunction, depending on which tissues are regenerated. For example, regeneration of rhabdosphincter tissue, pelvic ganglia, hypogastric nerve, and/or pelvic nerve may be useful for the treatment and/or preventing of SUI. Alternatively, regeneration of penile smooth muscle tissue and/or the cavernous nerve may be useful for the treatment and/or prevention of erectile dysfunction.

The method may comprise administering the composition to the subject by applying directly to the tissue to be regenerated. In other embodiments, the composition may be applied to a tissue to promote regeneration of tissue other than or in addition to the tissue to which the composition was directly applied. For example, application of the composition to the cavernous nerve may promote regeneration of corpora cavernosal tissue.

In particular embodiments, the composition may be administered to the subject to promote tissue regeneration in the subject following injury to the subject. For example, the compositions may be used in methods of promoting tissue regeneration in the subject following injury to one or more of the cavernous nerve, rhabdosphincter, pelvic ganglia, hypogastric nerve, and pelvic nerve of the subject. For example, the compositions may be used in methods of promoting tissue regeneration in the subject following one or more of crush injury to the cavernous nerve, tension injury of the pelvic ganglia, injury to penile smooth muscle tissue, or injury to striated muscle tissue of the subject. For example, the compositions may be used in methods of promoting tissue regeneration in a subject following crush injury to the cavernous nerve, such as that which may occur during prostatectomy. As another example, the compositions may be used in methods of promoting rhabdosphincter regeneration following a prostatectomy. In some embodiments, the compositions may be used to promote regeneration of multiple tissues in the subject following injury. The compositions may be administered to the subject at any suitable time point after injury to the subject, for any suitable duration and frequency to achieve the desired result.

In some embodiments, the compositions may administered to the subject before and/or during and/or after prostatectomy to promote tissue regeneration in the subject. For example, the composition may be administered to the subject before the prostatectomy. Alternatively or in combination, the composition may be administered to the subject during the prostatectomy. Alternatively or in combination, the composition may be administered to the subject following a prostatectomy.

e. Doses

For any of the uses described herein, the compositions may be administered to the subject at any suitable dose. Dosage may depend on various factors including the age of the subject, weight of the subject, frequency of administration, form of administration, other medications being administered to the subject, and the like. In some embodiments, the compositions comprise a peptide amphiphile concentration of 20 nM to 200 mM. For example, the compositions may comprise a peptide amphiphile concentration of 20 nM to 200 mM, 200 nM to about 100 mM, about 500 nM to about 90 mM, about 1 µM to about 80 mM, about 10 µM to about 70 mM, about 100 µM to about 60 mM, about 500 µM to about 50 mM, about 750 µM to about 40 mM, about 1 mM to about 30 mM, about 2 mM to about 20 mM, or about 10 mM. In some embodiments, the compositions may comprise a peptide amphiphile concentration of 10 mM to 20 mM. In some embodiments, the compositions may comprise about 1 µg to about 10 g sonic hedgehog protein. For example, the compositions may comprise about 1 µg, about 10 µg, about 100 µg, about 250 µg, about 500 µg, about 750 µg, about 1 mg, about 100 mg, about 200 mg, about 300 mg, about 400 mg, about 500 mg, about 600 mg, about 700 mg, about 800 mg, about 900 mg, about 1 g, about 1.5 g, about 2 g, about 2.5 g, about 3 g, about 3.5 g, about 4 g, about 4.5 g, about 5 g, about 5.5 g, about 6 g, about 6.5 g, about 7 g, about 7.5 g, about 8 g, about 8.5 g, about 9 g, about 9.5 g, or about 10 g of the sonic hedgehog protein. In some embodiments, at the time of application of the treatment, the following can be mixed together right before the application: a suitable concentration of calcium chloride, sonic hedgehog protein, and peptide amphiphile. In other embodiments, a suitable concentration of sonic protein and peptide amphiphile may be premixed, and a suitable concentration of calcium chloride can be mixed therewith prior to application.

Embodiments of the disclosed composition are set forth in the following non-limiting examples.

4. Kits

It is contemplated that embodiments of the technology are provided in the form of a kit. The kits comprise embodiments of the materials and methods described herein, and instructions for use of the kit. Individual components of the kit are packaged in appropriate containers and packaging (e.g., vials, boxes, blister packs, ampules, jars, bottles, tubes, and the like) and the components are packaged together in an appropriate container (e.g., a box or boxes) for convenient storage, shipping, and/or use by the user of the kit. For example, the kits may comprise a delivery vehicle, such as a lyophilized peptide amphiphile, and a sonic hedgehog protein. The kits may further comprise a salt to be combined with the delivery vehicle and sonic hedgehog protein prior to use in the subject. The kits may comprise a suitable container in which to combine the kit components (e.g. the delivery vehicle, the sonic hedgehog protein) prior to use. The kits are appropriate for use in a clinical setting and, in some embodiments, for use in a user's home. The components of a kit, in some embodiments, provide the functionalities of a system for delivery of sonic hedgehog protein to a subject. In some embodiments, certain components of the system are provided by the user. For example, the salt or the container may be provided by the user.

EXAMPLES

Example 1

Sonic Hedgehog Regulation of Human Rhabdosphincter Muscle and Implications for SUI Overview:

Rhabdosphincter (RS) muscle is damaged as a result of prostate and bladder cancer surgery, resulting in the development of stress urinary incontinence (SUI). During prostatectomy the bladder is disconnected from the urethra and then reattached after the prostate is removed. The RS is composed of specialized striated muscle that extends without interruption from the bladder neck to the pelvic floor, and the prostate is located inside the RS in humans, resulting in RS damage with prostate removal. The primary function of the RS is the initiation of voluntary micturition. Additional functions include random interruption of the urinary stream, reflex control during an increase in intra-abdominal pressure (coughing, sneezing, laughing, lifting), and complete emptying of the urethra after micturition. After prostatectomy an intact RS is important in order to support the urethra and bladder neck, which continues to be primarily responsible for continence to function as efficiently as possible.

Attempts to increase postoperative continence include preservation of as much RS muscle as possible along the length of the urethra. While the majority of men undergoing radical prostatectomy will regain reasonable urinary control through pelvic floor strengthening exercises, many will suffer from bothersome SUI requiring incontinence pads and garments, with detrimental impact on quality-of-life. Surgical therapies for SUI, including urethral slings and artificial urinary sphincters, have variable outcomes and significant side effects, including device failure, erosion of the urethra, transient pain and infection, and urinary retention, leading to a revision rate of 80% of patients by 10-15 years. Thus there is a critical unmet need for alternative methods to preserve or regenerate RS muscle, with important clinical implications not only for men undergoing prostatectomy, but also for all patients suffering from the stigma of urinary incontinence.

Materials and Methods

RS Tissue:

Human RS tissue was obtained from 10 patients who underwent radical cystoprostatectomy at Southern Illinois University and at Loyola University Medical Center. These patients all underwent cutaneous urinary diversion, thus there was no need for preservation of the RS muscle. A small amount of the periurethral muscle was removed and saved from the specimen side during surgery. Part of the RS tissues were frozen in liquid nitrogen prior to storage at −80° C. for histological examination and the remaining tissues were incubated in serum containing DMEM/F12 media for primary RS cell culture. The complete study protocol, including experimental procedures, was approved by the institutional review board of Southern Illinois University, Loyola University Health Systems, and the University of Illinois at Chicago, and written informed consent was obtained from all patients.

Primary RS Cell Culture:

Human RS tissue was obtained from the cystoprostatectomy specimens. Primary cell culture was established using a modified half-dry method. Briefly, RS tissues were cut into 1×1 mm² pieces and placed into the bottom of 25 cm² flasks. Culture flasks containing 2 ml of medium were placed upside-down in a 5% $CO_2$ incubator at 3° C. for 2 hours to allow the tissues to attach. Flasks were gently turned over and attached tissues were slowly covered by DMEM/F12 media containing 20% heat-inactivated fetal bovine serum (FBS) and an antibiotic cocktail (Penicillin, Streptomycin, Glutamine). The culture medium was replaced twice a week for three weeks, with increasing volume of media (up to 7 ml). Outgrowth of RS cells (passage 1) from tissues was monitored, and at confluence cells were split into new flasks for continued passages. Cell stocks were made from passages 1 to 3, and cells from passage 4 were used for experiments.

SHH Protein Treatment and SHH Inhibition of RS Cell Growth:

RS cells from passage 4 were grown in culture with Affi-Gel beads that were incubated over night at 4° C. with SHH protein (25 μl of a 1 μg/μl solution, R&D Systems), 5E1 SHH inhibitor (388 μg/ml, Hybridoma Bank), or PBS (control) for 3-6 days. Matrigel (100 μl) was placed at four places along the periphery of wells in six well plates. Affi-Gel beads (extended release vehicle) containing SHH protein, 5E1 SHH inhibitor or PBS were placed on the Matrigel and were gelled at 3° C. for 5 minutes. RS cells (15,000) were placed in the center of each well and the cells were allowed to adhere for one hour prior to adding 3.5 ml of DMEM/F12 media containing 10% FBS and antibiotic. Culture plates were placed in an atmosphere-controlled incubator (5% $CO_2$) at 3'C for 3-6 days. Cells were quantified by hemocytometer at 3 and 6 days. Four wells for each treatment group were quantified with four hemocytometer measurements performed on cells from each well. Experiments were performed in duplicate at each time point and were replicated on cells from three patients.

Trichrome:

Trichrome stain was performed on human RS tissue from cystectomy patients (n=6).

Immunohistochemical Analysis (IHC):

IHC was performed on frozen RS sections which were cut to 12 μm thickness and were post fixed in acetone at 4° C. for 15 minutes. OCT was removed with three washes of 1×PBS prior to blocking with 3% milk in PBS for one hour at 4° C. Sections were incubated overnight at 4° C. with 1/100 goat polyclonal antibody against SHH, PTCH1, and GLI-1 (Santa Cruz), rabbit polyclonal SMO (LSBio), mouse monoclonal skeletal muscle ACTIN (Abcam), and GLI-2, and GLI-3 (Rockland). Fluorescent secondary antibodies were 1/150 chicken anti-goat 488, and goat anti-mouse 594 (Molecular Probes, 1/150). H RP secondary antibodies were 1/150 rabbit anti-goat (Sigma-Aldrich), and mouse anti-rabbit (Santa Cruz). Sections were mounted using DPX Mounting media (Electron Microscopy Sciences, Hatfield, Pa.) and microscopy was performed using a Leica DM2500 microscope.

Apoptosis:

TUNEL assay was performed according to the ApopTag kit (Millipore) and all cells were co-stained for comparison with DAPI (0.02 μg/ml). Slides were mounted using Fluoromount (Thermo Fisher Scientific) and photography performed using a Leica DM2500 microscope.

Statistical Analysis:

Statistical analysis was performed by ANOVA with a Dunnett's posthoc test using the SPSS program. The results were reported ±the standard error of the mean. Results were significantly different if $p<0.05$.

Results

Figure 1B:
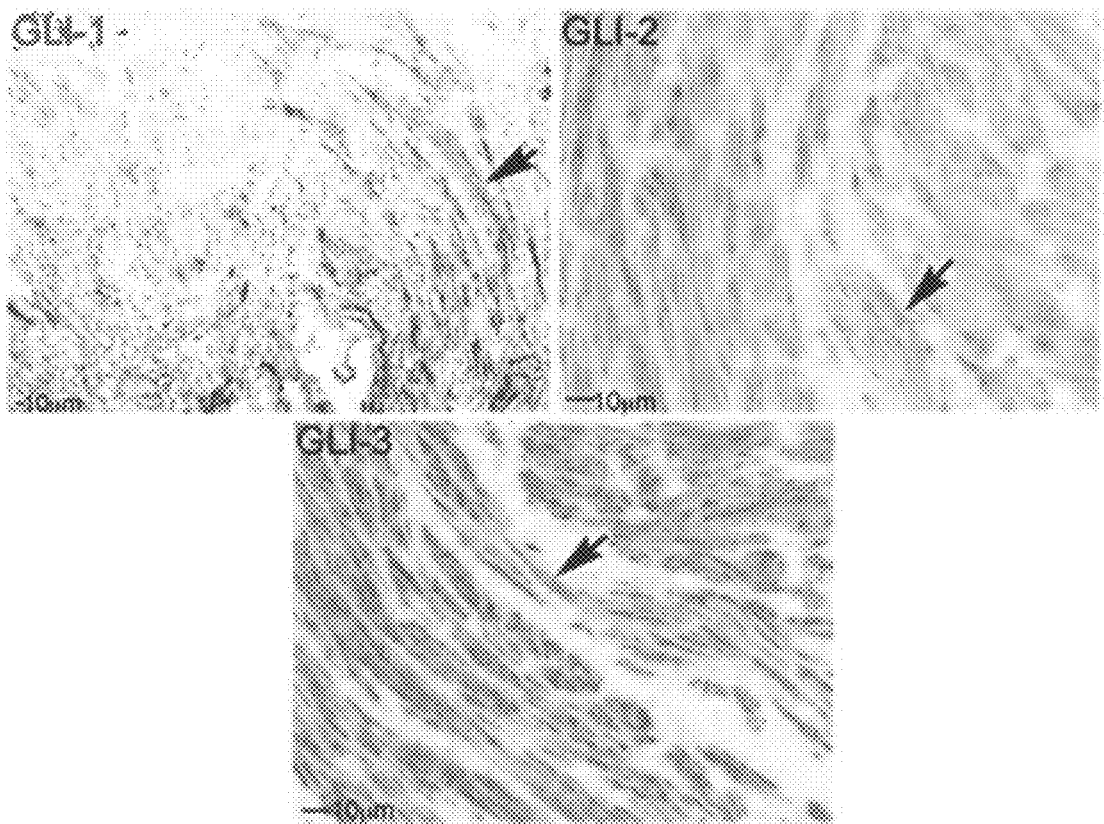

RS Tissue Morphology and Identification of SHH Pathway in Human RS:

Trichrome stain was performed on human RS tissue, which showed abundant skeletal muscle (red) and collagen (blue). IHC analysis was performed on human RS tissue assaying for SHH, and its receptors PTCH1 (binding) and SMO (non-binding). SHH, PTCH1 and SMO proteins were abundant in human RS muscle (FIG. 1A). The downstream targets of the SHH pathway, the GLI proteins were also expressed in human RS, with GLI-1, GLI-2 and GLI-3 identified in skeletal muscle (FIG. 1B).

Figure 2A:
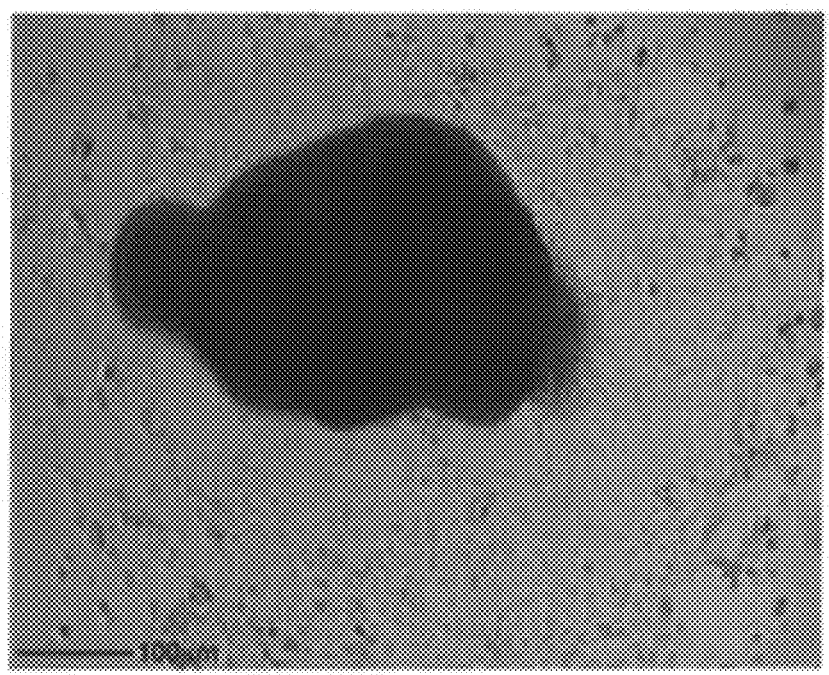
FIGS. 2A-2D show primary culture set up from human RS tissue.
Figure 2B:
Figure 2C:
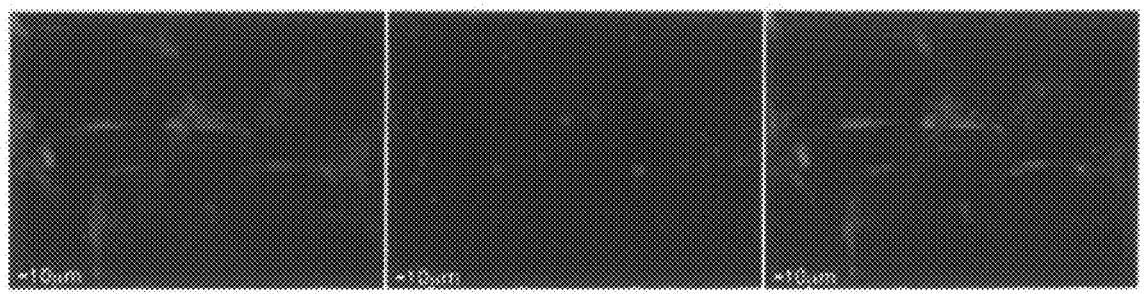
Figure 2D:
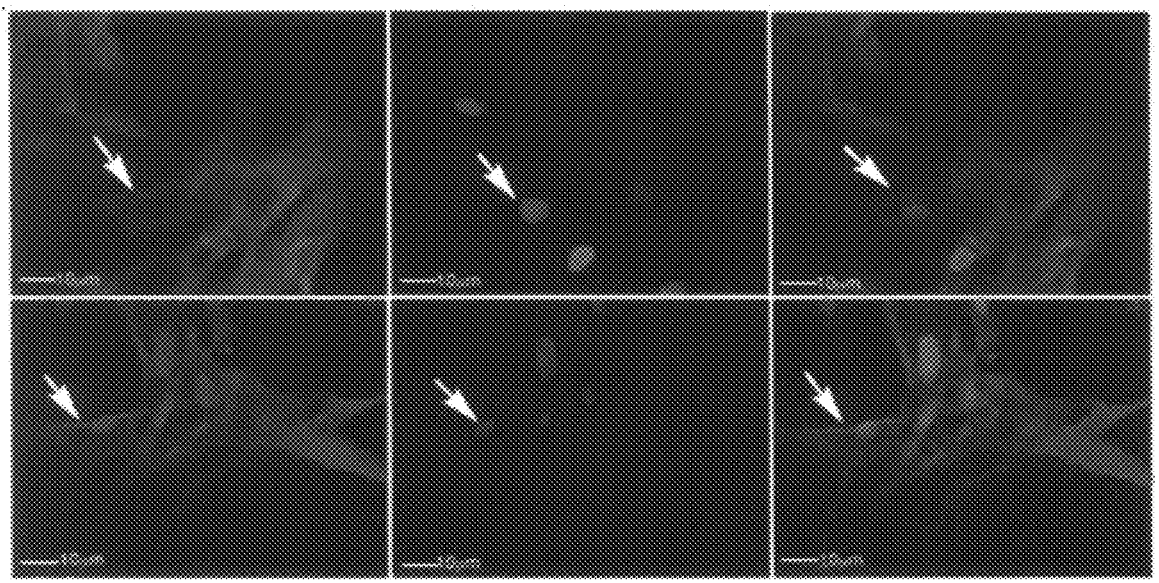

Establishing a Primary Culture from Human RS:

RS tissue was obtained at the time of cystoprostatectomy and RS cells were grown from primary culture (FIG. 2A). Cells had typical skeletal muscle architecture (FIG. 2B) and IHC analysis of cultured cells showed abundant staining for skeletal muscle actin (FIG. 2C). Skeletal muscle actin staining was abundant in muscle fibers (FIG. 2C). SHH protein was also identified in skeletal muscle fibers and was particularly abundant in the perinuclear region of muscle cells (FIG. 2D).

Figure 3A:
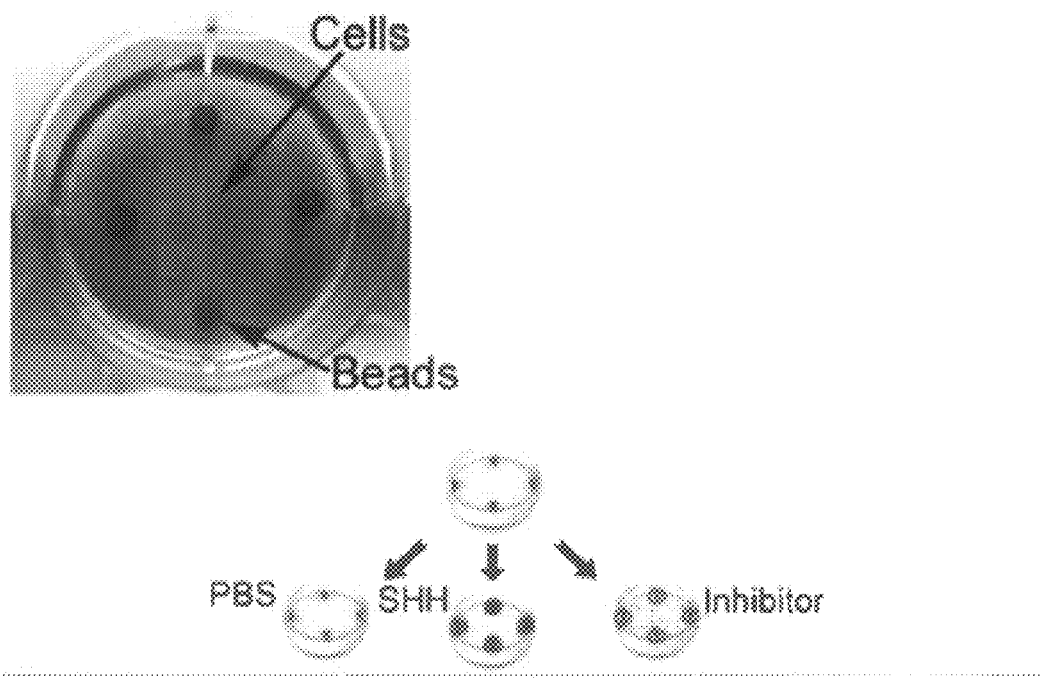
FIGS. 3A-3D show RS cells grown in 6 well plates in the presence of Affi-Gel beads containing, SHH protein, SHH inhibitor or PBS (control). Affi-Gel beads were placed in matrigel to hold them in place and RS cells were grown in the center of the wells (FIG. 3A). SHH treatment significantly increased the number of RS cells at 3 and 6 days of treatment, while SHH inhibition significantly decreased the number of RS cells (FIGS. 3B and 3C). TUNEL assay was performed on cells treated with PBS, SHH protein and 5E1 SHH inhibitor (FIG. 3D). Apoptosis occurred at low abundance in all cells, irrespective of treatment. Arrows indicate apoptotic nuclei. 200× magnification.
Figure 3B:
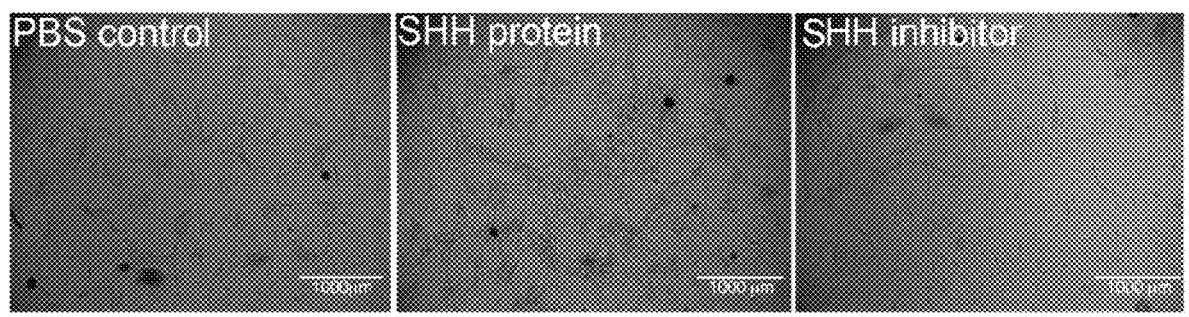
Figure 3C:
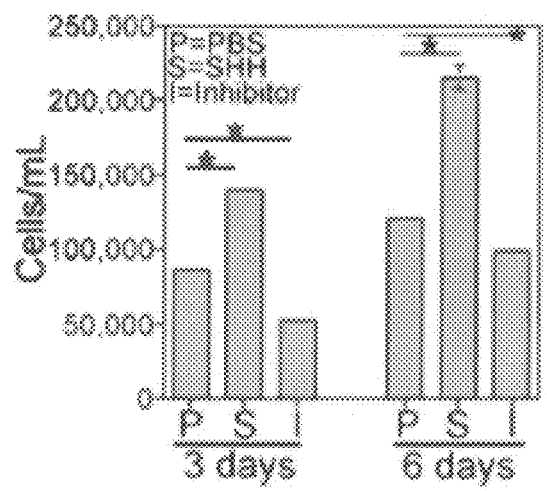
Figure 3D:
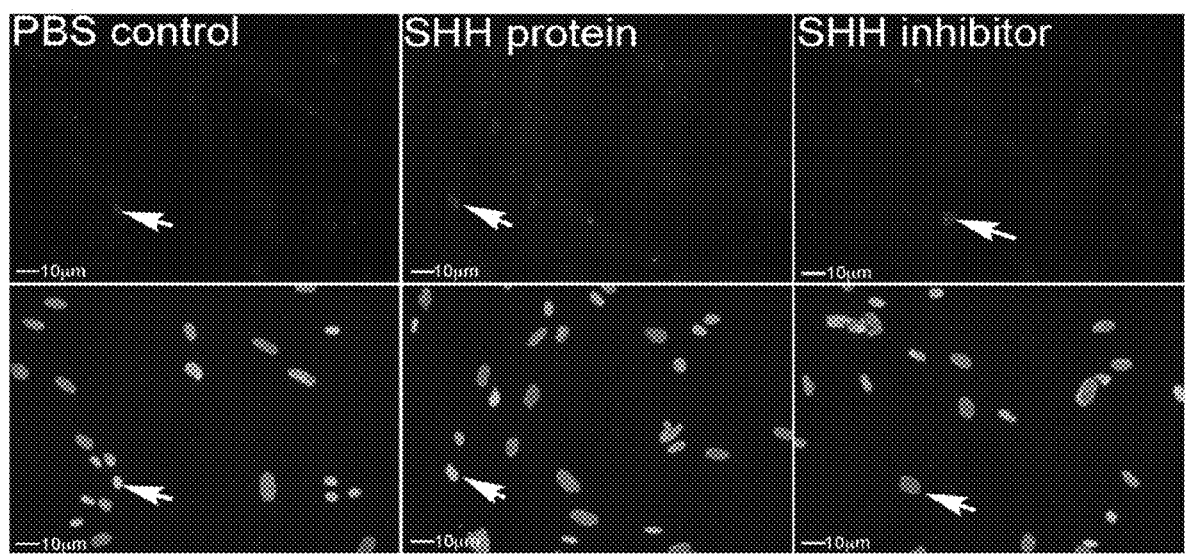

RS Growth with SHH Treatment and SHH Inhibition:

RS cells from passage four were grown in the wells of six well plates (FIG. 3A). Affi-Gel beads containing SHH protein, SHH inhibitor (5E1), or PBS (control) were placed in Matrigel in four corners of each well and media was added (FIG. 3A and FIG. 3B). Cells were grown from 3-6 days prior to counting cell number with a hemocytometer. The number of cells increased 1.62-fold (62%, p=0.0001) after three days of SHH protein treatment and decreased 1.66-fold (40%, p=0.0001) with SHH inhibition (5E1, FIG. 3B and FIG. 3C). At six days, cell growth increased 1.8-fold (78%, p=0.0001) with SHH treatment, and decreased 1.2-fold (18%, p=0.039) with SHH inhibition (FIG. 3B and FIG. 3C). TUNEL assay was performed on cells treated with PBS, SHH protein and 5E1 SHH inhibitor (FIG. 3D). Apoptosis occurred at low abundance in all cells irrespective of treatment (FIG. 3D).

DISCUSSION

This study identities members of the SHH pathway in striated skeletal muscle of human RS tissue obtained from cystoprostatectomy patients, suggesting SHH involvement in RS homeostasis. Manipulation of the SHH pathway through inhibition of SHH binding to its receptor PTCH1, decreased RS growth of cultured patient cells, and identified the necessity of active SHH signaling for RS growth and regeneration.

Exogenous SHH protein increased the number and speed of RS cell proliferation by comparison to controls, showing the responsiveness of RS muscle to SHH treatment, and suggesting that intervention with SHH may be possible to promote/enhance regeneration of RS muscle. During radical prostatectomy, RS may be excised or injured as the apex of the prostate is disconnected from the urethra and during creation of the urethrovesical anastomosis after the prostate is removed. The premise would be to apply SHH locally to the remaining RS muscle at the time of prostatectomy to enhance RS regeneration. SHH protein rather than RNA delivery is preferable since it has been shown that where there is interruption of innervation, that there is a block in SHH protein synthesis. Ideally, the delivery vehicle should be capable of local, extended release of SHH protein, easily deliverable in vivo at the time of prostatectomy, and biodegradable.

The in vitro analysis of human RS cells grown in culture shows a quick response in increased growth that is significantly enhanced 62% by three days of SHH treatment, and as much as 78% by six days of treatment. This suggests a short window of SHH treatment would be needed to enhance RS growth, and impact SUI.

A peptide amphiphile hydrogel delivers SHH protein as the hydrogel breaks down and with established release kinetics of 73% cumulative protein delivery by six days. While protein release is dependent on ionic strength and sheer stress within the tissue, this timing should be sufficient to promote RS regeneration and the hydrogel may be optimized for maximal RS delivery and regeneration enhancement. The results presented herein show that SHH response to skeletal muscle injury is similar enough to smooth muscle recovery that SHH PA delivery methods may be applicable to SUI prevention, and significantly impact SUI treatment strategies.

Current state of the art treatments to improve RS function involve isolation of muscle satellite cells to try and re-grow the muscle. The methodology described herein be a significant improvement over these strategies since the hydrogel delivery of SHH is a non-invasive, and biodegradable method of preserving/regenerating RS muscle. During embryogenesis, the SHH pathway is essential for muscle development, and SHH improves age associated impairment of skeletal muscle in mice. A potential mechanism for SHH function in RS may involve the GLI proteins Myf5, a skeletal muscle regulatory gene, is a direct target of long-range Shh signaling during muscle development through positive regulation by GLI transcription factors. Delayed ischemic muscle repair has been observed in old mice with an impaired upregulation of GLI-1. GLI signaling is complex, with several isoforms that are activated by the SMO part of the SHH receptor. Upon SHH binding to PTCH1, this releases the repression of PTCH1 on SMO, allowing SMO to preferentially upregulate the formation of GLI-2 and GLI-3 to their active forms. Active GLI-2 and GLI-3 regulate activation of SHH target genes, including GLI-1, which is indicative of high level SHH signaling. In this study GLI-1, GLI-2 and GLI-3 were abundant in human RS muscle, indicating active SHH signaling through GLI-1, which may be an exploitable avenue for intervention to further enhance RS regeneration.

Example 2

Pelvic and Hypogastric Nerves are Injured in a Rat Prostatectomy Model, Contributing to Development of Stress Urinary Incontinence Stress urinary incontinence (SUI) affects 40% of elderly men, is common in diabetic patients and in men treated for prostate cancer, with a prevalence of up to 44%. Seventy-two percent of prostatectomy patients develop SUI in the first week after surgery and individuals who do not recover within 6 months generally do no regain function without intervention. Incontinence has a profound impact on the physical and mental health of patients, who view incontinence pad use as detrimental to their quality of life. The artificial urinary sphincter (AUS) is the gold standard for the treatment of this disorder, however most men will continue to need at least one pad per day, and device failure, erosion of the urethra, urinary retention, transient pain and infection are significant side effects that lead to a revision rate of up to 80% by 10-15 years. Thus, a critical unmet need exists to develop novel and less invasive SUI treatments/preventions.

Figure 4A:
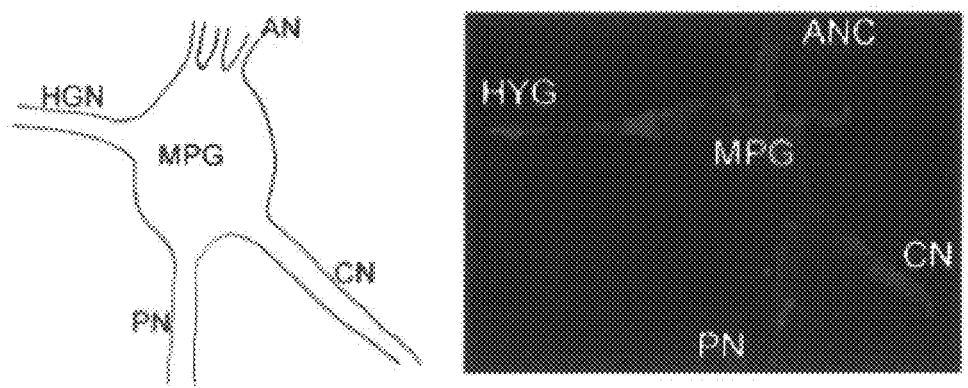
FIGS. 4A-4C show diagrams of rat anatomy.
Figure 4B:
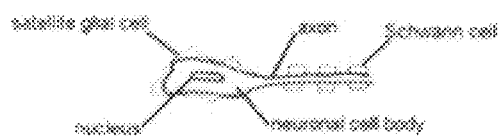
Figure 4C:
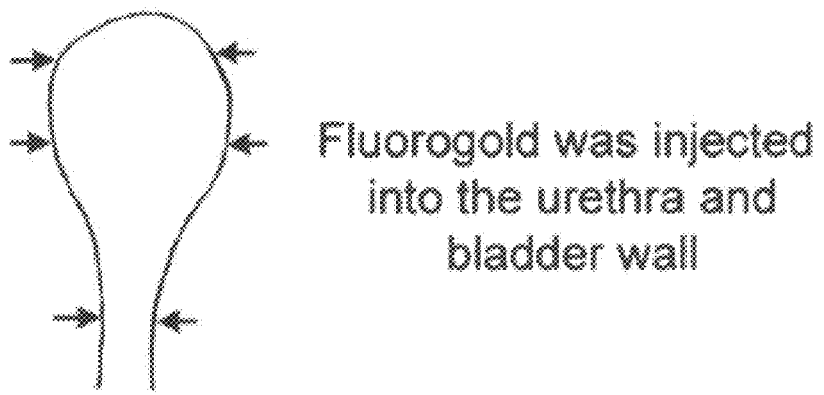

During prostatectomy, the cavernous nerve (CN), which provides innervation to the penis, undergoes crush, tension, and resection injury, resulting in downstream penile remodeling and erectile dysfunction (ED) in up to 85% of patients. There are other nerves that form part of the major pelvic ganglion (MPG), including the hypogastric (HYG, sympathetic) and pelvic (PN, parasympathetic) nerves, which provide innervation to the bladder and urethra (FIG. 4A). The HYG controls bladder neck contraction and bladder relaxation while the PN regulates contraction of the bladder and relaxes the bladder neck to expel urine. Each nerve contains neurons, and glial cells which control the microenvironment, providing support, nutrients and receptors for signaling and communication (FIG. 4B).

This study examined whether other parts of the MPG including the HYG and PNs are injured during prostatectomy, perhaps due to tension injury on the MPG, and contribute to the development of post prostatectomy SUI. This idea is novel since it has been presumed that surgical removal of rhabdosphincter muscle, which occurs when the bladder is disconnected from the urethra and then reconnected after prostate removal, is the cause of SUI. In this study it was evaluated whether prostatectomy induced injury to the MPG extends beyond the CN, to the PN and HYG, and contributes to SUI.

A role for the Sonic hedgehog (SHH) pathway in PN and HYG homeostasis and regeneration has not previously been examined. In this study, Affi-Gel beads were used for SHH protein delivery the subject in a rat prostatectomy model.

Materials and Methods

Animals:

Adult Sprague Dawley rats (n=37, P115-120) were obtained from Charles River. The study was carried out in accordance with the recommendations in the Guide for the Care and Use of Laboratory Animals of the National Institutes of Health, and the experiments comply with the current laws of the country in which they were performed. The animal care protocol was approved by the Office of Animal Care and Institutional Biosafety at the University of Illinois at Chicago, and animals were cared for in accordance with institutional OACIB approval.

Bilateral CN Crush/MPG Tension Injury:

Bilateral CN crush was performed on Sprague Dawley rats. Briefly, MPG/CN were exposed and microforceps (size 0.02×0.06 mm) were used to crush the CN bilaterally for 30 seconds. The extent and reproducibility of crush was previously verified by visible change in nerve color and indentation. Rats were sacrificed at 1, 2, 4 and 7 days after CN crush (n=3, 3, 4, and 4) and the CN, PN, EHYG, and ANC were dissected. Normal adult Sprague Dawley rats (n=13), and sham controls (n=6. CN exposed but not manipulated), were examined for comparison.

Fluorogold Injection into Urethra and Bladder Wall:

Sprague Dawley rats underwent sham (n=2) or CN crush (n=2) prior to fluorogold (5% w/v) injection into the wall of the urethra and bladder using a 10 µl Hamilton syringe with a 28-gauge needle (Restek). Three fluorogold injections were performed on each side (FIG. 1C). Two injections of 2.5 µl were performed into the bladder wall and one 5 µl injection into the wall of the bladder neck/urethra, while avoiding injection into the bladder lumen. Injection sites were sealed with glue. Rats were sacrificed after 7 days and the MPG were isolated.

Immunohistochemical Analysis (IHC):

IHC was performed on frozen CN, PN. HYG, and ANC nerves (n=8 each) that were sectioned 141 µm in thickness. OCT was removed with 1 XPBS prior to blocking in 3% milk Sections were incubated overnight at 4 degrees C. with 1/100 goat polyclonal antibodies for SHH (N19) and PTCH1 (Santa Cruz), and rabbit SMO (LifeSpan BioSciences), caspase 3 cleaved and caspase 9 (Cell Signaling), and mouse caspase 8 (Cell Signaling). Secondary antibodies were chicken anti-goat, chicken anti-rabbit, and goat anti-mouse 594 (Molecular Probes). Sections were mounted using DPX Mounting media and fluorescence was visualized using a Leica DM2500 microscope.

TUNEL:

Apoptotic cells were identified using the Apoptag kit (Millipore) on sham (n=6) and 1, 2, 4, and 7 day CN crushed (n=14) Sprague Dawley rat MPG. Fluorescence was visualized using a Leica DM2500 microscope.

Organ Culture:

Bilateral CN crush was performed and MPG tissues (n=4) were isolated after two days, and were embedded in sterile culture plates containing 150 µl of reduced growth factor Matrigel (Corning Life Sciences). Affi-Gel beads (100-200 mesh, BioRad), incubated overnight at 4 degrees C. with 1 XPBS (n=2) or SHH protein (25 µl of a 1 µg/µl solution, R&D Systems, n=2), were embedded in the Matrigel near the MPG. Matrigel was gelled at 3 degrees C. for 5 minutes prior to adding RPMI media (Sigma) and an antibiotic cocktail (100× Penicillin-Streptomycin-Glutamine, Thermo Fisher). Culture plates were placed in an atmosphere-controlled incubator (5% CO2) at 3 degrees C. for three days.

Results

Figures 5A, 5B:
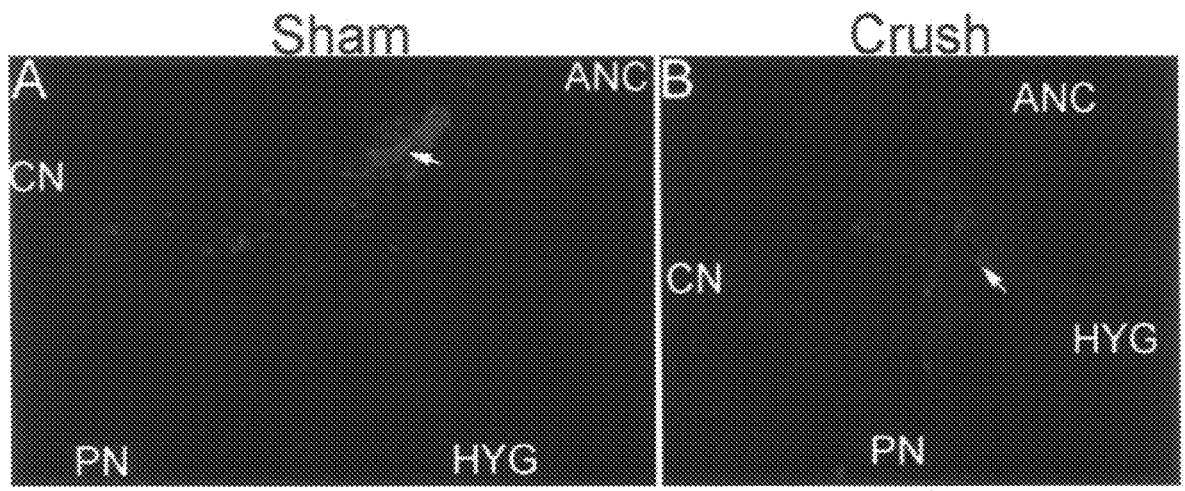
FIGS. 5A-SB show fluorogold staining in the bladder. Fluorogold was injected into the bladder and urethral wall of sham and CN crushed Sprague Dawley rats. After 7 days the MPG were isolated and examined for fluorogold, which underwent retrograde transport to neurons of the MPG that innervate the bladder and urethra, and composite photos of all nerves and MPG were assembled from 100× photos.
(FIG. 5B) Fluorogold stained neurons are reduced in the MPG with CN crush/MPG tension injury, indicating interruption of innervation between the MPG and bladder/urethra.
Figure 6A:
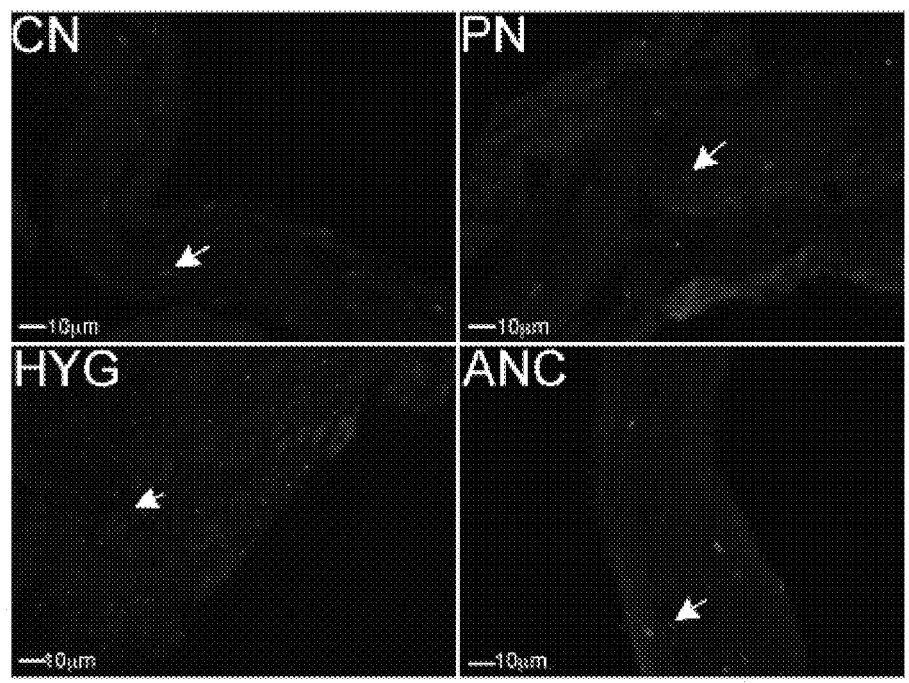
FIGS. 6A-6B show levels of apoptosis.
Figure 6B:
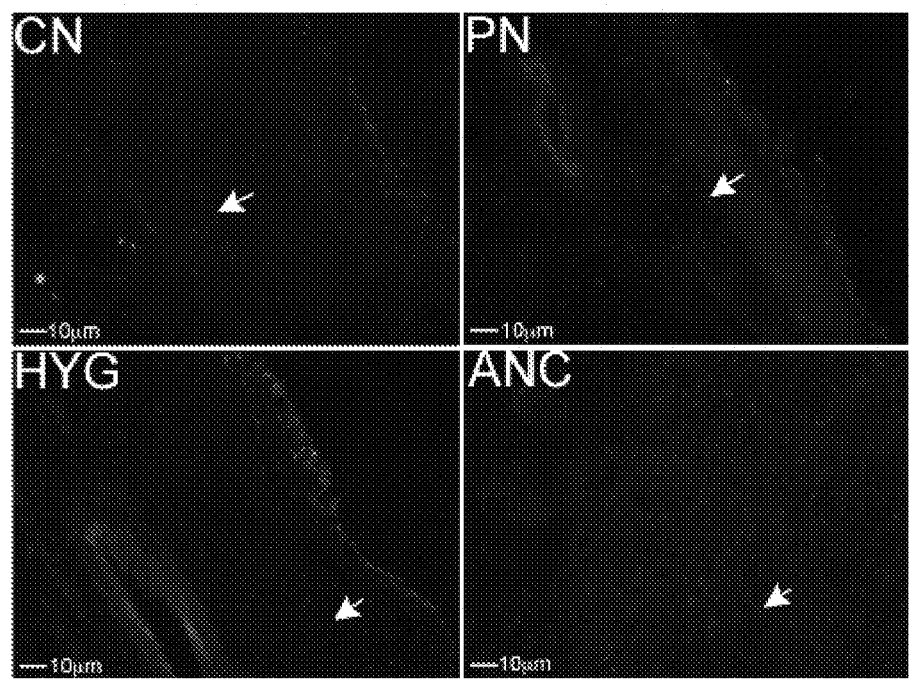

Interruption of Innervation Between the Urethra 'Bladder Neck'Bladder and MPG with CN Crush:

Fluorogold was abundant in neurons dispersed throughout the MPG in sham rats (FIG. 5A), indicating intact innervation. After CN crush, the number of fluorogold positive neurons decreased throughout the MPG (FIG. 5B), including regions that innervate the bladder and urethra, indicating interruption of innervation to the urethra/bladder neck/bladder occur with MPG tension/CN crush injury. Apoptosis under normal, homeostatic conditions: IHC was performed assaying for caspase 3 cleaved protein, a marker of apoptotic cells, in MPG from rats that underwent sham surgery. Caspase 3 cleaved was identified at a low level in the CN, PN, HYG, and ANC nerves (FIG. 6A), indicating low cell turnover under uninjured homeostatic conditions. Low abundance apoptosis was confirmed by TUNEL analysis (FIG. 6B) of sham MPG.

Figure 7A:
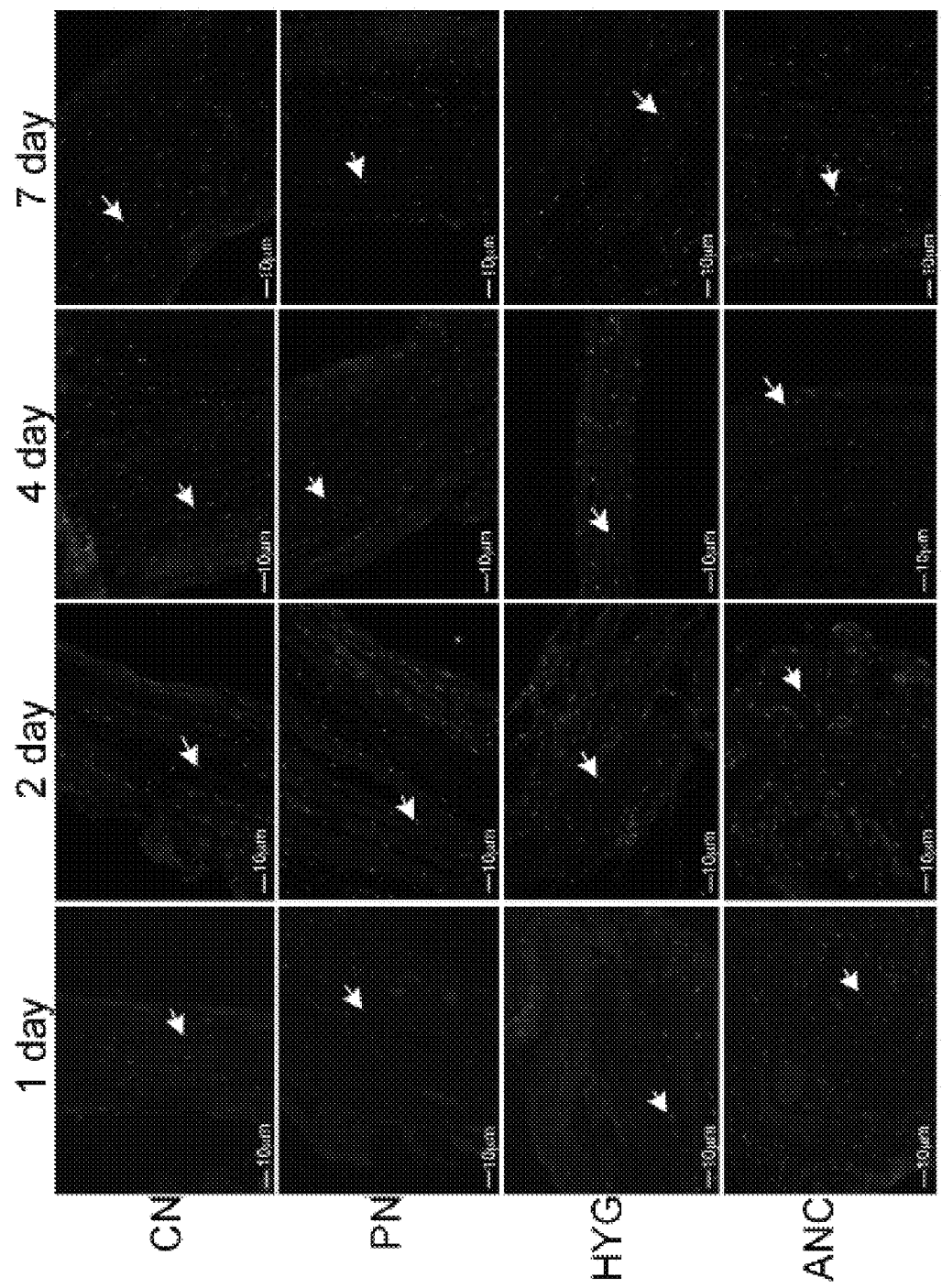
FIGS. 7A-7B.
Figure 7B:
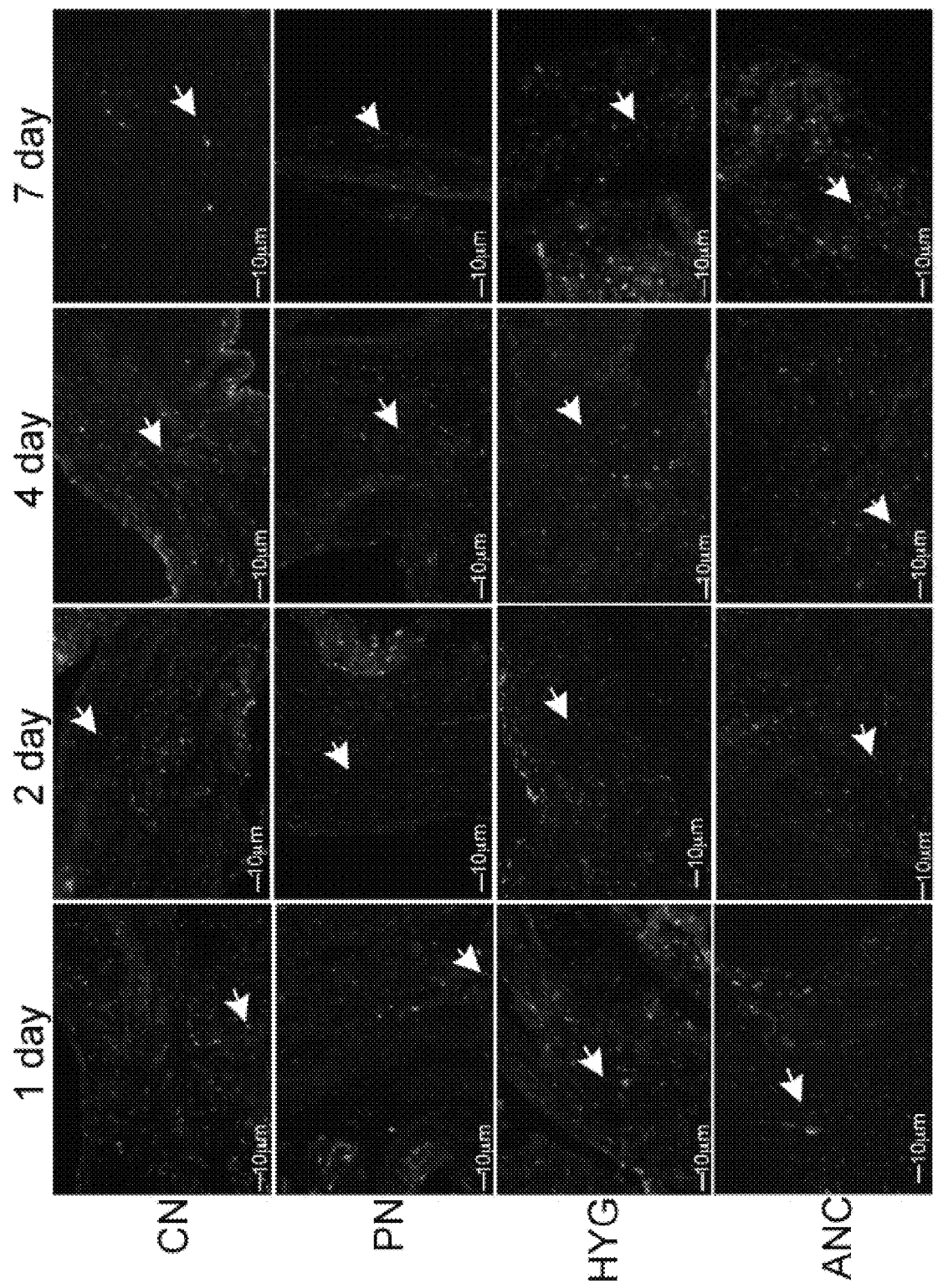

Apoptosis in MPG Nerves with CN Crush MPG Tension Injury:

IHC was performed on rat MPG 1-7 days after bilateral CN crush. Caspase 3 cleaved protein was upregulated in a time-dependent manner, primarily in glial cells of the CN, PN, HYG, and ANC nerves from 1-7 days after CN crush/MPG tension injury (FIG. 7A). Caspase 3 cleaved was most abundantly observed at day 1 after injury in the ANC nerves, which 150 provide innervation to the prostate. By day 2, caspase 3 cleaved was also abundant in the CN, PN and HYG nerves, and remained abundant at 4 and 7 days after injury (FIG. 7A). Apoptosis was confirmed by TUNEL assay in glial cells of all nerves (FIG. 7B).

Apoptotic Mechanism.

Figure 8A:
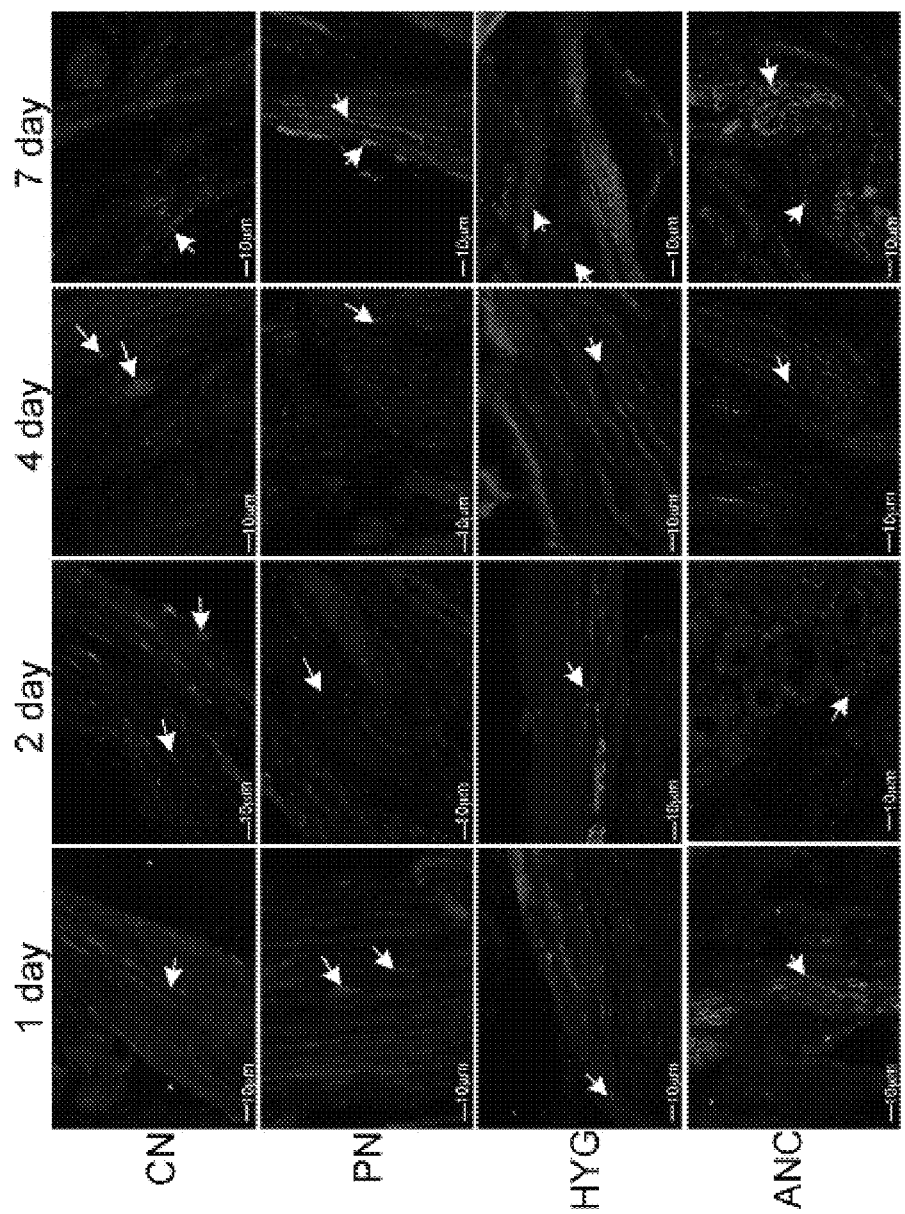
FIGS. 8A-8B show immunohistochemical analysis.
Figure 8B:
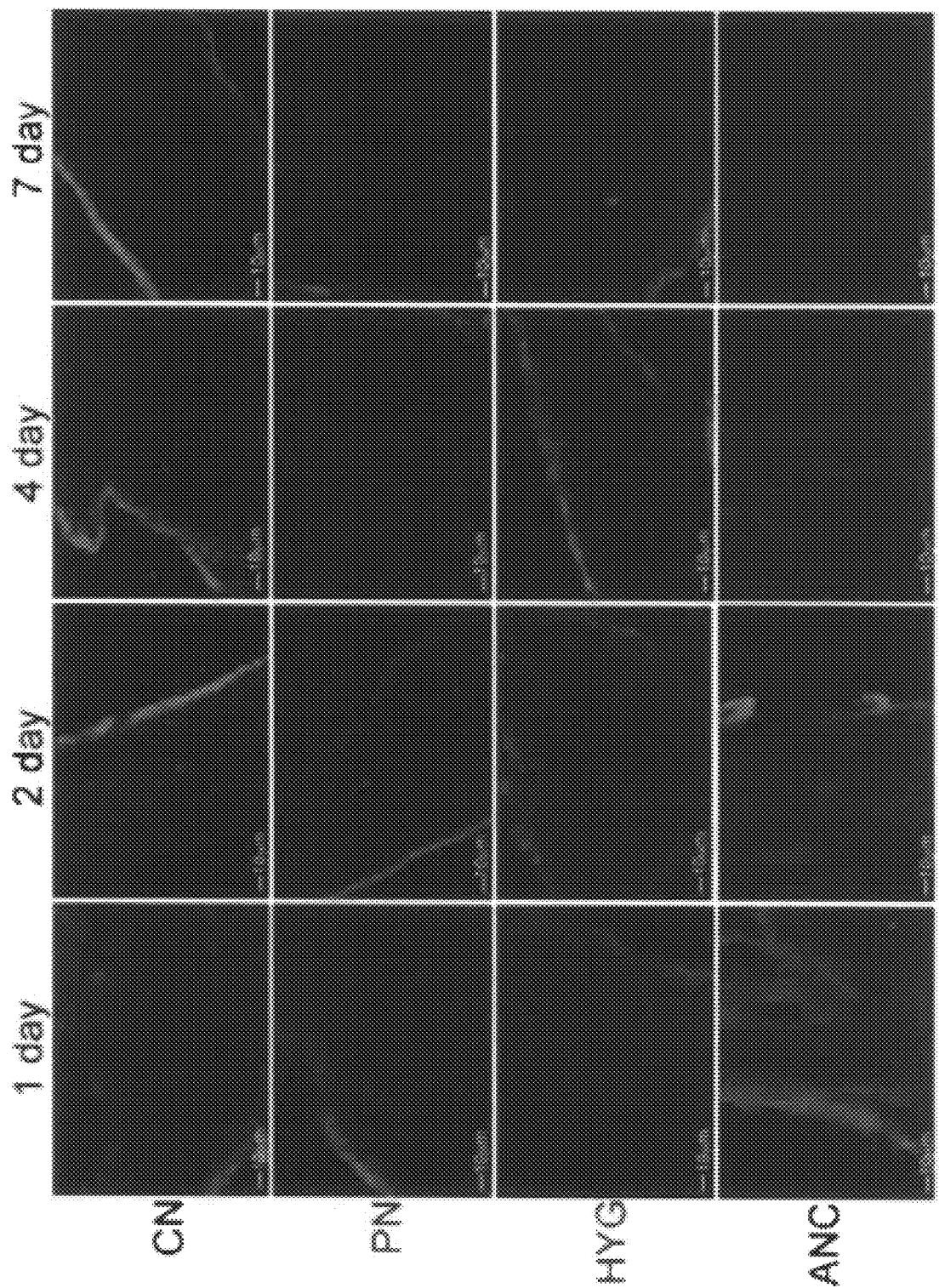

The pathway by which apoptosis takes place in the rat MPG after injury was evaluated by examining if caspase 9 and/or caspase 8 proteins were increased in the CN, PN, HYG and ANC nerves from 1-7 days after CN crush. Caspase 9 (intrinsic) was observed in all nerves of the MPG, and was primarily identified in Schwann cells of the CN, PN, HYG, and ANC nerves (FIG. 8A). Only a small number of neurons stained for caspase 9 (FIG. 8A), indicating that it is primarily glial cells/support cells that undergo apoptosis in the first week after CN injury. Caspase 8 (extrinsic) protein was not identified in any of the nerves of the MPG 1-7 days after CN injury (FIG. 8B), indicating that the apoptotic mechanism occurs primarily through the intrinsic pathway.

Figure 9:
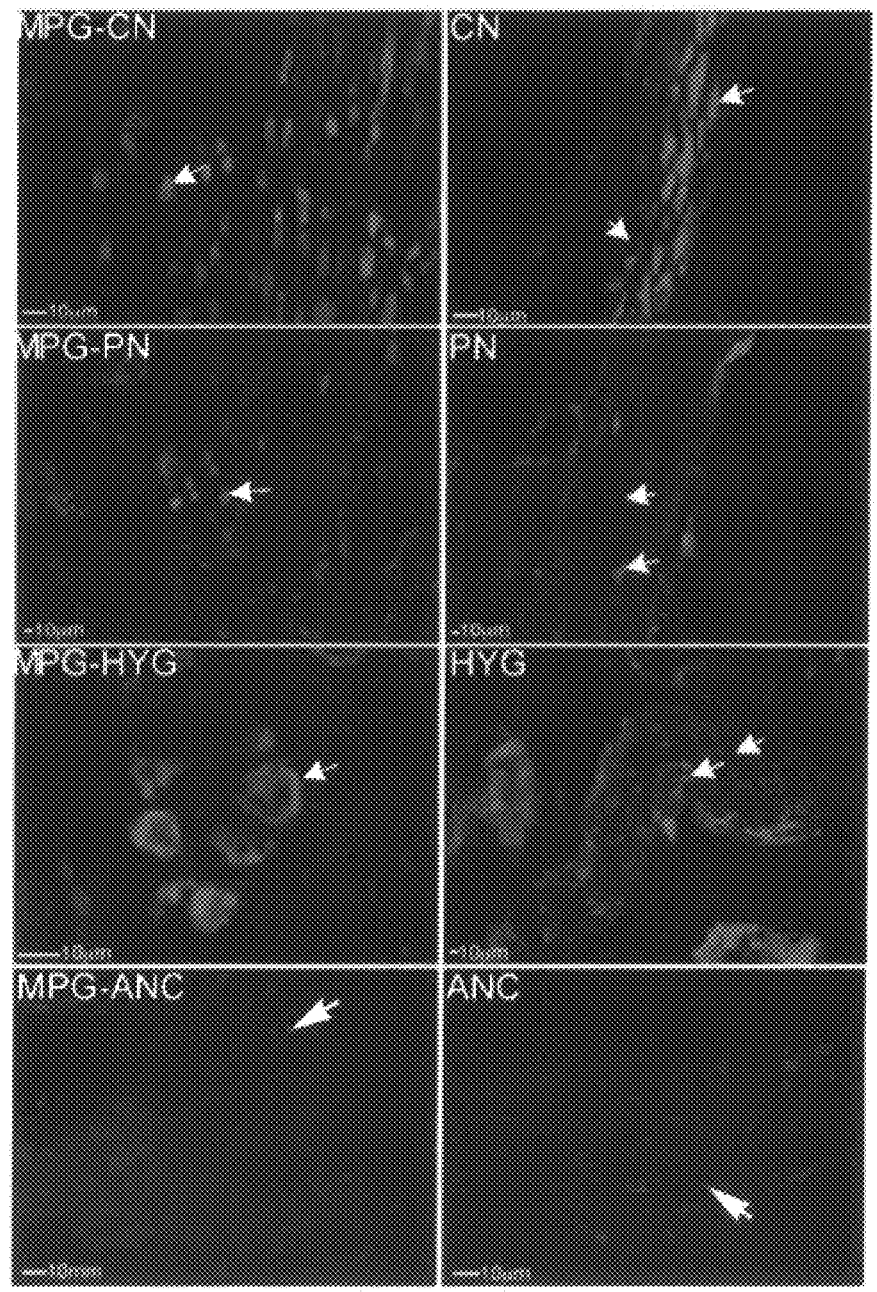
FIG. 9 shows immunohistochemical analysis of SHH protein in normal/uninjured MPG, CN, PN, HYG and ANC. SHH protein was abundant in MPG neurons that innervate the penis, bladder, and prostate and in neurons and glial cells of the CN, PN, HYG and ANC. Arrows indicate SHH protein. 100-200× magnification.
Figure 10:
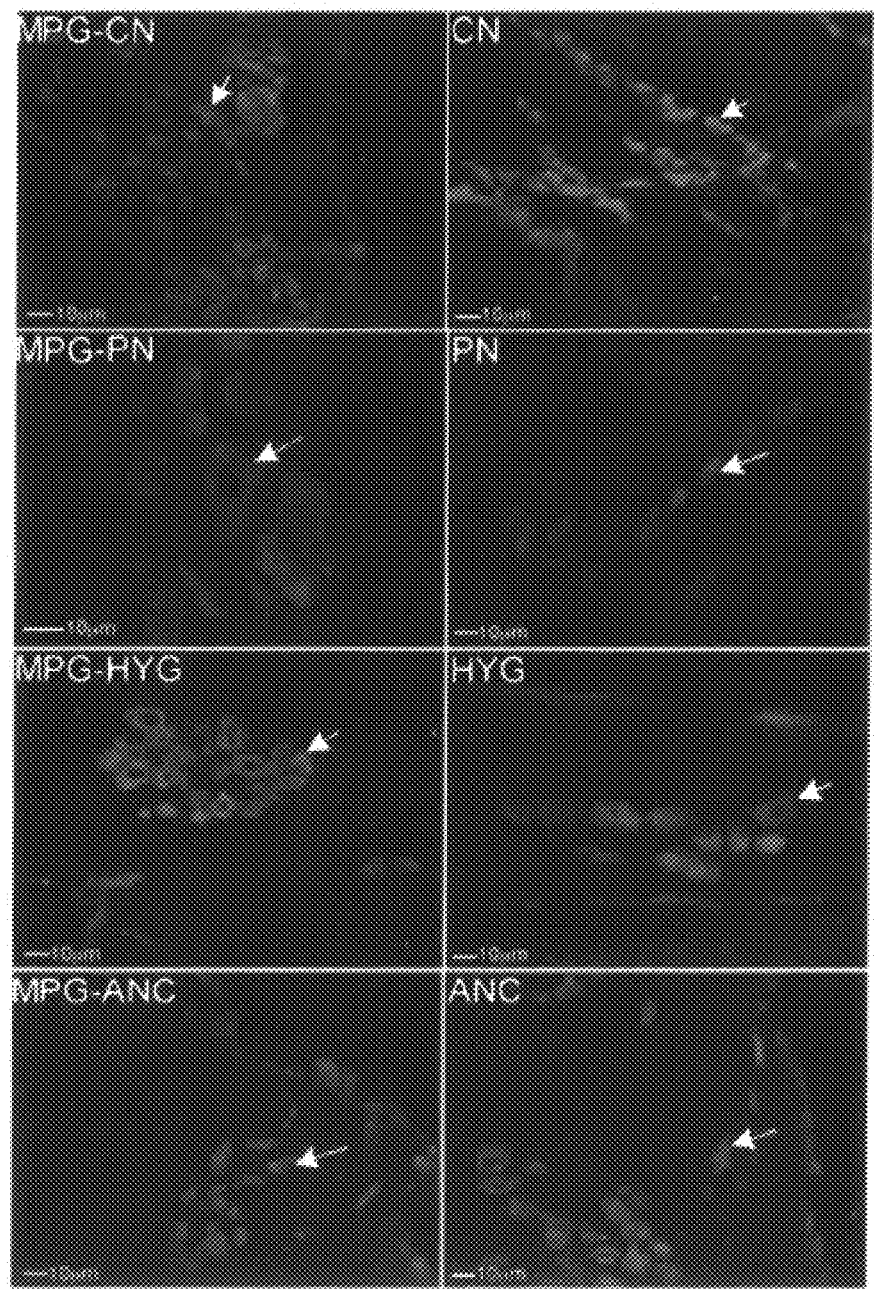
FIG. 10 shows immunohistochemical analysis of the SHH receptor PTCH1, in MPG from normal/uninjured rats PTCH1 protein was abundant in neurons of the MPG that innervate the penis, bladder and prostate and the associated CN, PN, HYG and ANC nerves. PTCH1 was not identified in glial cells. Arrows indicate PTCH1 protein. 200-400× magnification.
Figure 11:
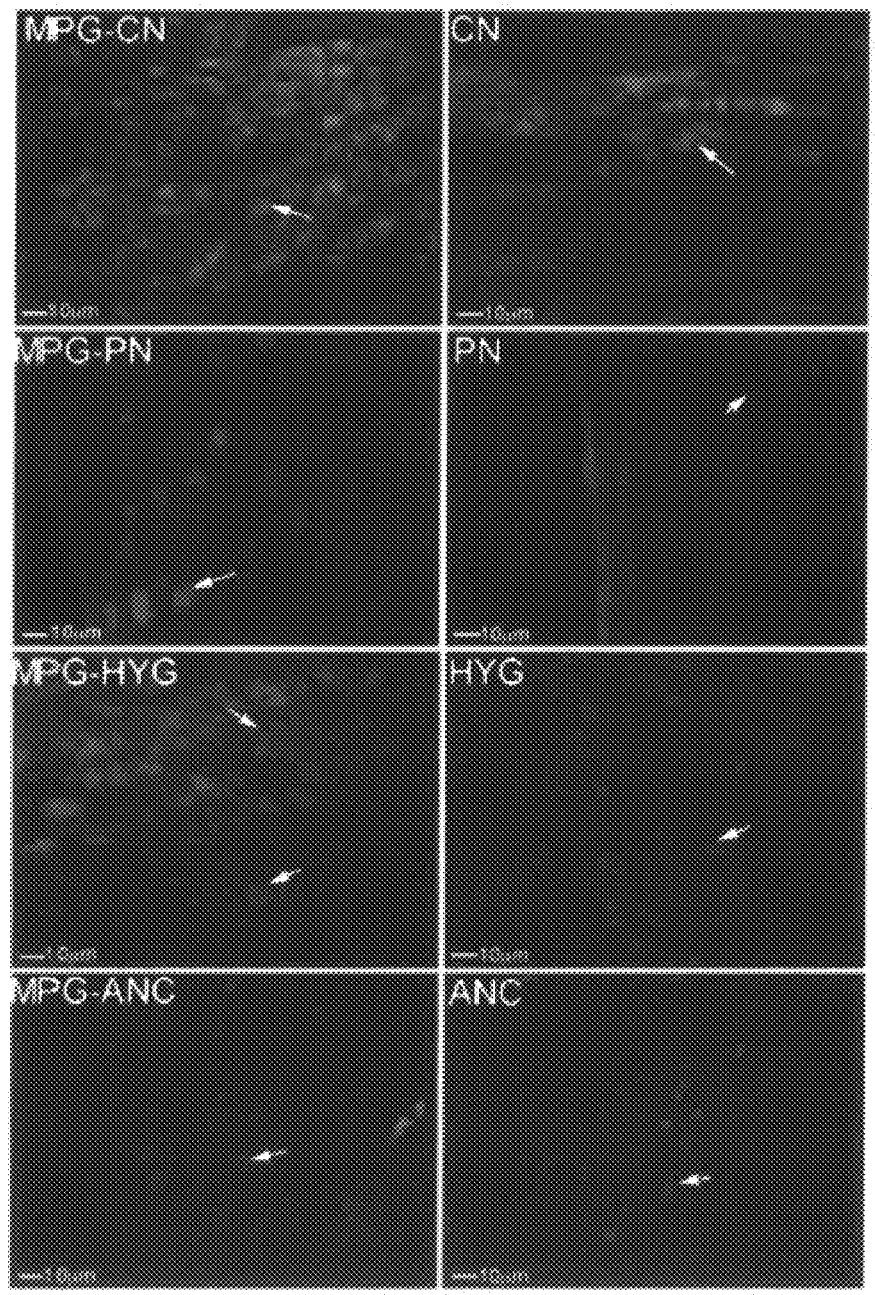
FIG. 11 shows immunohistochemical analysis of the SHH receptor SMO, in MPG from normal/uninjured rats SMO was abundant in neurons of the MPG that innervate the penis, bladder, and prostate and in the associated CN, PN, HYG and ANC nerves. Arrows indicate SMO protein. 200-400× magnification.

Sonic Hedgehog Pathway is Abundant in all Nerves of the Uninjured MPG:

IHC for SHH, and its receptors PTCH1 and SMO, were performed on normal/uninjured rat MPG isolated from Sprague Dawley rats (n=8). SHH protein was identified in neurons of the caudal portion of the MPG that innervates the penis, and in neurons and Schwann cells of the CN (FIG. 9). SHH protein was abundant in the region of the MPG that innervates the PN and the HYG, and in neurons and glial cells of the PN and HYG (FIG. 5) SHH protein was also present in ANC neurons (FIG. 9). PTCH1 was identified in neurons of the MPG that provide innervation to the penis, bladder, and prostate, and the respective nerves (FIG. 10). PTCH1 was not observed in glial cells (FIG. 10). SMO was abundant in MPG regions that innervate all nerves of the MPG and in the respective nerves (FIG. 11). Both neurons and associated glial cells stain for SMO (FIG. 11).

Figure 12A:
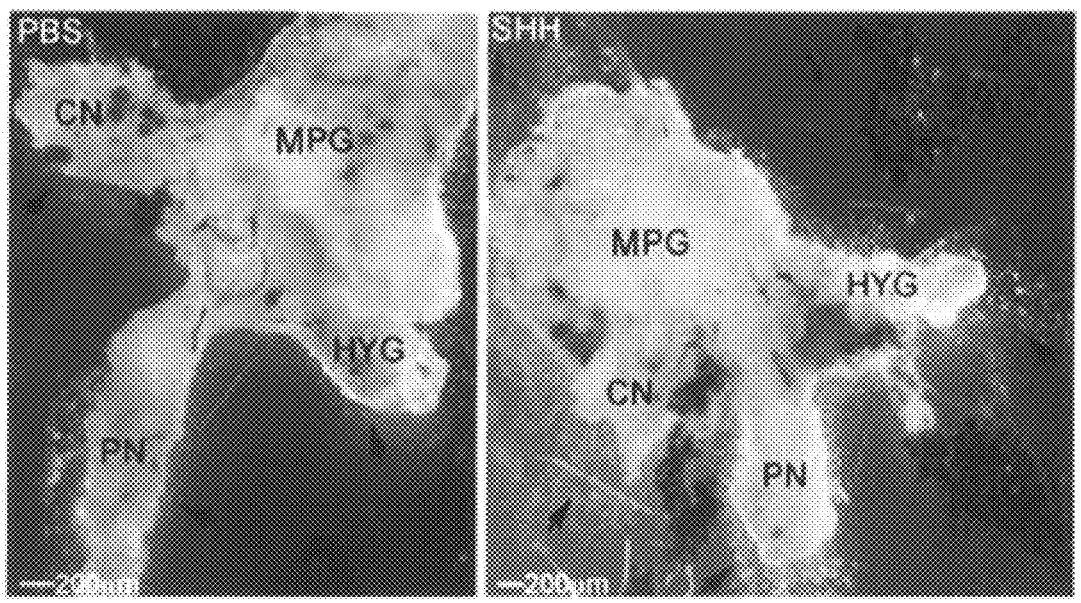
FIGS. 12A-12B. MPG from adult Sprague Dawley rats that underwent CN crush/MPG tension injury were dissected after two days and were grown in organ culture for three days with PBS or SHH protein. Low abundance neurite formation occurred from neurons in all nerves of the MPG with CN crush (FIG. 12A). SHH treatment increased the number of neurites that formed from all nerves after injury (FIG. 12A), indicating that PN and HYG neurons are responsive to SHH treatment. Arrows indicate neurites. Red bar is region expanded in FIG. 12B. 40× magnification. Enlarged regions of the PN and HYG show abundant neurite formation with SHH treatment in comparison to PBS controls (FIG. 12B).
Figure 12B:
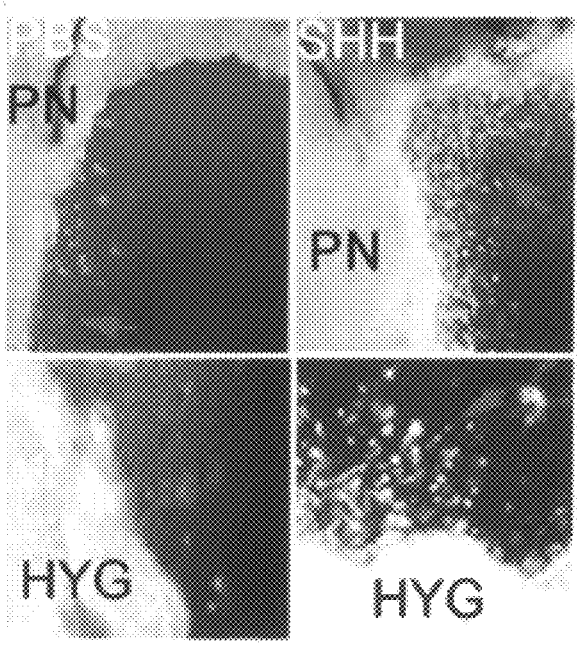

SHH Protein Treatment Induces Neurite Formation in PN and HYG Neurons:

MPG from Sprague Dawley rats that underwent CN crush/MPG tension injury were dissected after two days and grown in organ culture for three days with PBS or SHH protein. Low abundance neurite formation occurred from neurons in all nerves in response to CN crush (FIGS. 12A and B). SHH treatment increased the number of neurites that formed from all nerves after injury (FIGS. 12A and B), indicating that PN and HYG neurons are responsive to SHH treatment.

DISCUSSION

Unlike the penile projecting neurons of the CN, which cluster in the "horn" region of the MPG, bladder neurons are relatively evenly distributed throughout the ganglion. When the CN is crushed, simulating the MPG tension injury which occurs during prostatectomy, there is an interruption of innervation between the bladder/bladder neck/urethra and the MPG, as is shown by the decrease in fluorogold positive neurons (FIG. 5). This previously unsuspected loss of innervation may contribute to bladder dysfunction observed in men after prostatectomy. Injury to the entire MPG, including the PN and HYG nerves, was confirmed with IHC analysis of caspase 3 cleaved (apoptotic marker) and TUNEL assay. Apoptosis/cell turnover is normally low in the MPG under uninjured homeostatic conditions. However with CN crush/MPG tension injury, apoptosis increased in all nerves of the MPG in a time dependent manner, indicating that not only is the CN injured during prostatectomy, but also the PN and HYG, and thus may contribute to SUI development.

Apoptosis occurs primarily in glial cells of all nerves of the MPG in the first week after CN injury. Glial cells surround the neuronal cell body and control the microenvironment of sympathetic ganglia, providing support, nutrients and receptors for signaling and communication. It is suggested that the change in the neuronal microenvironment, caused by loss of growth factors and interaction provided by the glia, leads to later neuronal apoptosis, after the first week post-injury. The mechanism of how apoptosis takes place was examined in all nerves of the MPG. There are two apoptotic pathways that stimulate apoptosis via a caspase dependent mechanism. These are the extrinsic pathway, which is initiated by a death ligand, and the intrinsic pathway, which is dependent on the mitochondria and formation of the apoptosome, which facilitates activation of procaspase 9 to the active form. Once activated, caspase 8 in the extrinsic pathway, and caspase 9 in the intrinsic pathway, cleave and activate downstream caspase 3 and 7, resulting in activation of several target proteins and ultimately apoptosis. In this study caspase 3 cleavage was examined and TUNEL assay was performed to identify apoptotic cells, and then examined caspase 8 and 9 in all nerves of the MPG, to determine the mechanism. Caspase 9 was identified in glia of CN, PN. HYG and ANC nerves from 1-7 days after CN injury. Caspase 8 was not identified in any of the nerves after CN injury, indicating that the apoptotic mechanism takes place through an intrinsic, mitochondrial dependent mechanism. This is significant since intervention to prevent the apoptotic response may be possible using localized delivery of caspase inhibitors to the MPG at the time of prostatectomy, and thus impact nerve function, and potentially SUI and ED.

This study is the first identification that the SHH pathway is active in the PN and HYG. SHH function within PN and HYG neurons and glia is supported by neurite activation in the presence of exogenous SHH protein, suggesting that SHH may be useful to promote PN and HYG regeneration.

Example 3

Peptide Amphiphile Delivery of Sonic Hedgehog Protein Promotes Neurite Formation in Penile Projecting Neurons Peripheral neuropathy is common in diabetic and aging men and in prostate cancer patients, who undergo prostatectomy surgery to treat prostate cancer, resulting in loss of erectile function in up to 85% of patients. The cavernous nerve (CN), which provides innervation to the penis, is subject to crush, tension and resection injuries due to manipulation of the pelvic plexus to remove the prostate. State of the art treatments, including PDE5i, are ineffective in 61-69% of erectile dysfunction (ED) patients with peripheral neuropathy, so development of novel treatments, which target the regenerative process, are sorely needed to improve clinical outcome.

Figure 13A:
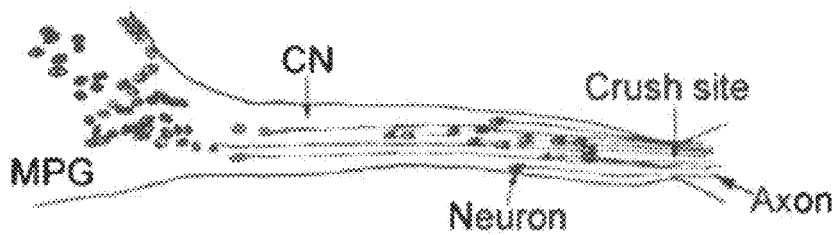
FIGS. 13A-13C.
Figure 13B:
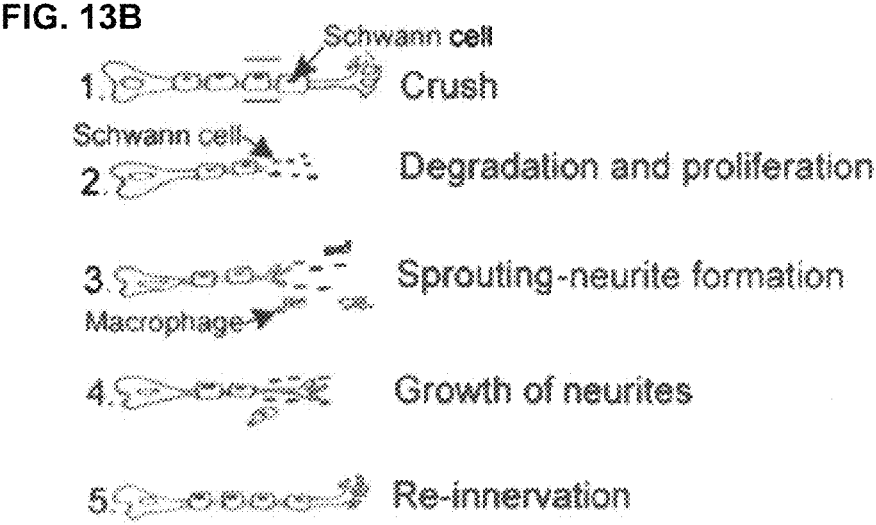

In this study the key regulatory role of the SHH pathway in promoting CN regeneration was examined by examining its function in Wallerian degeneration and neurite formation. Peripheral nerve regeneration is a complex process, initiated with injury to the CN (FIG. 13A). Separation of proximal and distal ends of the injury site occurs within 30 minutes and degeneration of the distal segment begins within 24-36 hours (FIG. 13 B). The axonal skeleton and membrane break apart, activating Schwann cells to demyelinate, if myelinated, proliferate, phagocytize the debris, and release cytokines that recruit macrophages to finish the cleanup process. Neurites initiate from the proximal end of damaged axons within 4 days, and grow towards bands of Büngner, which are formed of aligned Schwann cells. Neurites are attracted by growth factors produced by Schwann cells.

SHH protein is abundant in Schwann cells (co-localize with S100, a Schwann cell marker), which migrate to the injury site when the CN is damaged. SHH is critical to maintain normal CN architecture, is neuroprotective and plays a significant role in CN regeneration. With SHH inhibition, demyelination of CN fibers and degeneration of non-myelinated fibers occurs. CN injury decreases SHH protein in major pelvic ganglia (MPG) neurons that innervate the penis and reintroduction of SHH protein by extended release PA hydrogels improves erectile function (60%), improves neural morphology, and suppresses penile apoptosis which occurs with loss of innervation. Part of the regenerative mechanism in response to SHH treatment involves maintaining neural-glial interactions. Shh mRNA is synthesized in PG neurons, while immunohistochemical analysis identified SHH protein in both neurons and associated glial cells. Similarly the SHH receptor Patched protein was abundant in both neurons and glia, while Smoothened, the regulator of SHH pathway activity, was abundant in satellite glial cells, indicating the importance of the SHH pathway for neuronal-glial interaction and regulation of the neuronal microenvironment. In other organs, components of the SHH pathway are expressed in human macrophages, and Shh may act as a macrophage chemoattractant during initiation of gastritis in the stomach. The present study evaluated whether SHH is a key regulator of regenerative processes taking place at the proximal injury site, including neuronal sprouting/neurite formation. A role for SHH in neurite formation of MPG/CN neurons has not previously been investigated and is critical to understanding of how to facilitate peripheral nerve regeneration Materials and Methods Animals:

Sprague-Dawley rats (n=58) postnatal day 115-120 (P115-P120) were obtained from Charles River (Wilmington, Mass.). The study was carried out in accordance with the recommendations in the Guide for the Care and Use of Laboratory Animals of the National Institutes of Health. The animal care protocol was approved by the Office of Animal Care and Institutional Biosafety at the University of Illinois at Chicago and animals were cared for in accordance with institutional approval.

CN Crush Surgery:

MPG/CN were exposed and microforceps (size 0.02×0.06 mm) were used to crush the CN bilaterally for 30 seconds. CN crushed rats were sacrificed immediately (n=3), at 2 (n=3), 4 (n=7) and 9 (n=9) days after injury and were grown in organ culture.

Organ Culture:

The caudal portion of the MPG, which innervates the penis, and attached CN (n=39), were identified and isolated. The pelvic, hypogastric and ancillary nerves, along with the adjacent regions of the MPG that innervate the bladder, rectum and prostate, were not included in the dissection. MPG/CN were embedded in sterile 6 well culture plates containing 1-11 of reduced growth factor Matrigel (Corning Life Sciences 356231). The type of Matrigel used for the study is critical since some high growth factor forms of Matrigel commonly used can influence neurite formation. Affi-Gel beads (100-200 mesh, Bio Rad), incubated overnight at 115.4° C. with 1×PBS (n=13), DMSO (n=3), SHH protein (25 µl of a 10 µg/µl solution, R&D Systems, n=12), 5E1 SHH inhibitor (Hybridoma Bank, 286 µg/ml, n=6) or cyclopamine (10M, n=6), were embedded in the Matrigel near the MPG/CN. Matrigel was gelled at 37° C. for 5 minutes prior to adding RPMI media (Sigma) and an antibiotic cocktail containing Penicillin-Streptomycin-Glutamine (100×, Thermo Fisher Scientific). Culture plates were placed in an atmosphere-controlled incubator (50% CO2) at 3 degrees C. for three to five days. Additional rats underwent bilateral CN crush, and MPG/CN tissues (n=12) were isolated after three days and were embedded in Matrigel as described above. Affi-Gel beads were used to deliver either 1×PBS (n=4), or SHH protein (1 µg/l, R&D Systems, n=8). Neurite formation was examined after three days in culture.

Quantification of Neurites:

Quantification of neurites was performed by counting the total number of growth cones visible for each tissue grown in organ culture by a blinded observer at 160× magnification, normalized by tissue perimeter length (mm). Photos of the MPG/CN (representative photos are presented in the figures) were magnified on computer screen until growth cones were clearly visible, and all growth cones in the entire tissue were counted and the perimeter was measured. Three to five photos for each tissue were counted and averaged. Images were obtained using an Olympus SZ-CTV dissecting microscope and Axiocam R1.2 Carl Zeiss digital camera. Quantification of neurite length was performed by measuring the length of neurites for each tissue grown in organ culture by a blinded observer at 160× magnification. Photos of the MPG/CN were magnified on computer screen until growth cones were clearly visible, and neurite length was measured at seven representative points for each tissue. Neurite length is reported as the average length per tissue. Quantification of perimeter length over which neurites formed in each tissue was performed by a blinded observer at 160× magnification. Photos of the PMG/CN were magnified on computer screen until growth cones were visible, and the distance in cm along the tissue perimeter was measured in which sprouts formed for each tissue. Average perimeter length over which neurites formed was reported in cm.

Bilateral CN Crush Surgery with SHH or MSA Protein Treatment by PA:

(C16)-$V_2A_2E_2NH_2$) PA was prepared. PAs were synthesized at the Northwestern Institute for BioNanotechnology in Medicine Chemistry Core Facility. PAs were synthesized by standard methods via FMoc-based solid phase synthesis on Rink resins. Through standard deprotection and coupling procedures, the VVAAEE sequence was synthesized on the resin beads and terminated in a palmitic acid (C16) alkyl tail. Batches were cleaved from the resin, precipitated in cold ethyl ether, and lyophilized to a powder. PAs were then purified by preparative high-performance liquid chromatography and lyophilized to a powder. Each dry powder was redissolved in PBS, adjusted to pH 7 using dilute sodium hydroxide, and dialyzed against de-ionized water. The PA solutions were then re-lyophilized and stored at −80° C. as a dry powder until needed. 20 mM $CaCl_2$ was added to a glass slide and 8 µl of 20 mM PA plus either 2.27 µg SHH or mouse serum albumin (MSA, control) proteins were pipetted onto the slide to form the PA. Bilateral CN crush was performed and PA containing the protein intercalated within the hydrogel, was transferred with forceps on top of the crushed CNs. The release rate of SHH protein from the PA was previously determined to be 90% by 75 hours. MPG/CN were isolated 4 days after CN injury and were grown in organ culture for an additional 4 days with SHH or MSA PA. Groups were: Continuous SHH treatment {n=6), continuous MSA (control) treatment (n=5), SHH given initially and then withheld (n=7), and SHH withheld initially for 4 days and then given in vitro (n=5).

Immunohistochemical analysis (IHC):

Immunofluorescence, a form of immunohistochemical analysis that utilizes fluorescent secondary antibodies, was performed on frozen MPG/CN sections (14 µm) from rats treated with PBS (control, n=5), or SHH protein (n=5). Crushed CNs (n=3) were also examined. Sections were incubated overnight at 4° C. with primary antibodies against neuronal nitric oxide synthase (nNOS, Transduction Laboratories), growth associated protein 43 (GAP43, Chemicon), or SHH (Santa Cruz, N-19 antibody). Secondary antibodies were 1/150 goat anti-mouse 594 or chicken anti-goat 488 (Molecular Probes). Sections were mounted using DPX Mounting media (Electron Microscopy Sciences) and fluorescence was visualized using a Leica DM2500 microscope.

Statistics:

Where comparisons of three or more groups were made, ANOVA with a Scheffe's or Dunnett's posthoc test was performed using SPSS program Where two groups were compared, a Levine test (SPSS) was first performed to ensure equal variance between groups, and then at-test. The results were reported±the standard error of the mean. Where there was unequal variance between groups, a Mann-Whitney U Test was performed, and the results reported as the median with interquartile range. Results were considered significantly different if $p<0.05$.

Results

Figure 13C:
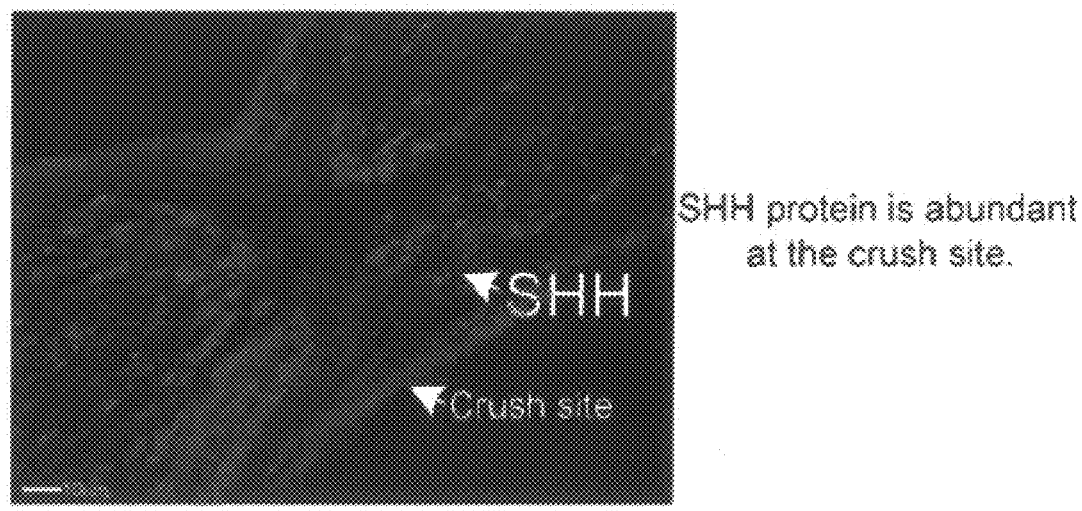

SHH Protein was Abundant in Crushed CN:

SHH protein localization was examined by IHC analysis of CN's that underwent crush injury and were sacrificed after 4 days (n=3). SHH protein was abundant in cells on either side of the crush site (FIG. 13C).

SHH co-localizes with S100 in Schwann cells of the CN that following tie placement, simulating a crush injury.

Figure 14A:
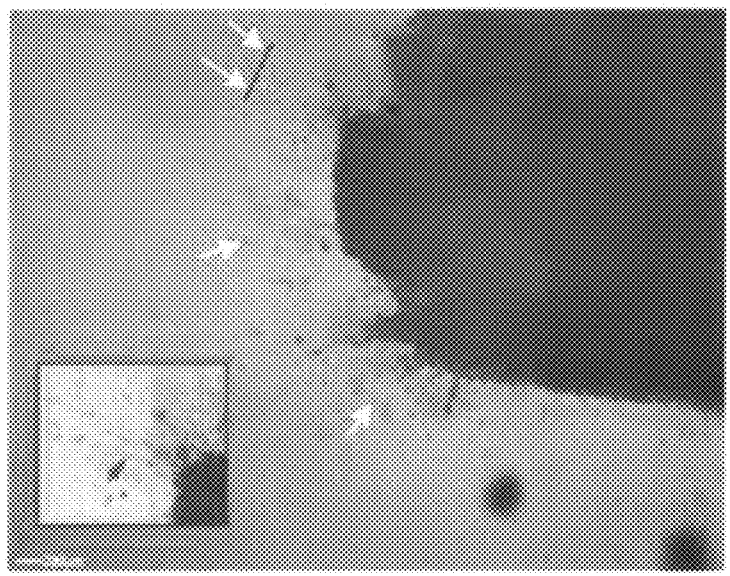
FIGS. 14A-14C.
Figure 14B:
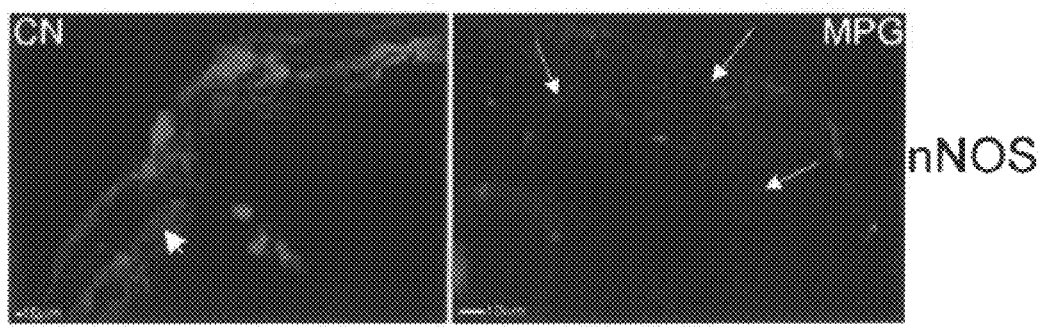
Figure 14C:
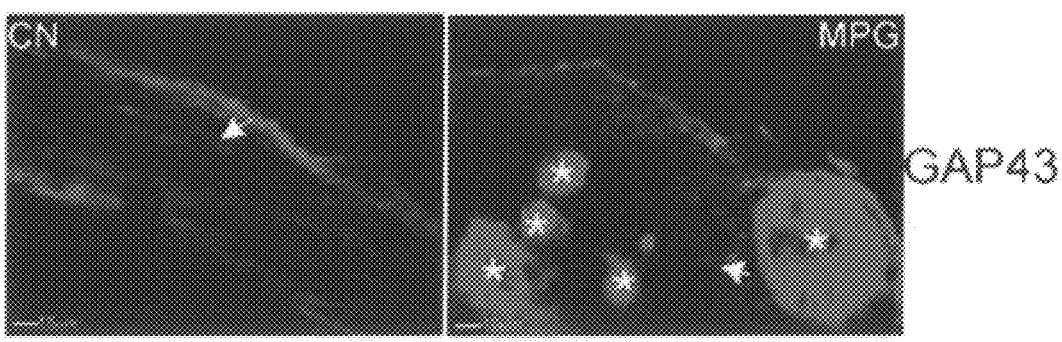

Neurite Formation in Uninjured MPG/CN:

Organ culture was performed on MPG/CN taken from uninjured Sprague Dawley rats and tissues were treated with PBS (control). A highly magnified view of a small portion of control MPG shows growing neurites with clearly visible growth cones at the tips and elongating fibers (FIG. 14A, arrows indicate visible growth cones). In order to confirm that neurites that are forming are from only the caudal portion of the MPG that provides innervation to the penis, nNOS IHC was performed. It has previously been well documented that nNOS is abundant in penile projecting neurons. Since antibodies do not migrate well in intact tissue, such as our organ culture MPG/CN, we sectioned the tissue prior to IHC analysis Many of the neurites break off with sectioning, however we were able to identify nNOS in elongating neurites of the CN and in growth cones of the MPG (FIG. 14B), indicating that they originate from penile projecting neurons. In order to confirm that nNOS protein was localized in growing neurites, we performed GAP43 (growth cones marker) staining on serial sections. GAP43 was abundant in elongating neurites of the CN and in growth cones of the MPG (FIG. 14C).

Figure 15A:
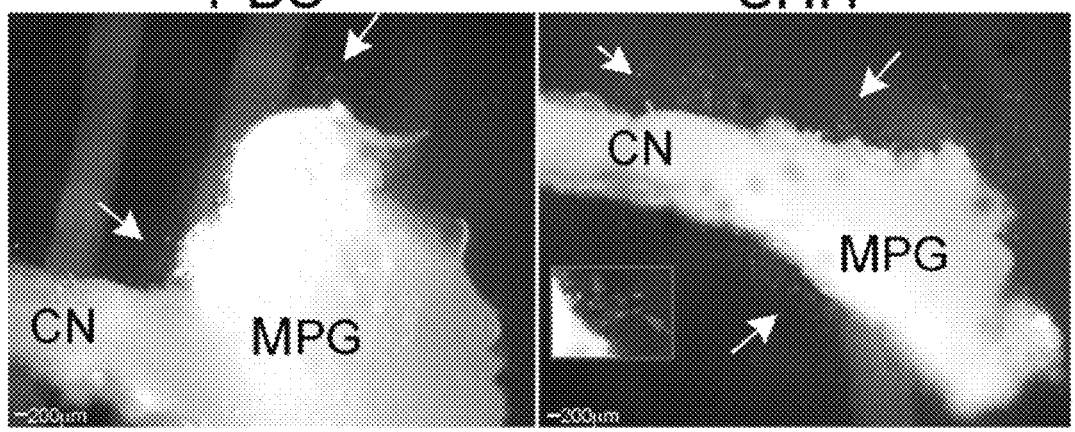
FIGS. 15A-15D: Normal/uninjured MPG and CN tissue grown in organ culture for three days with 1×PBS (control) or SHH protein (FIG. 15A) Limited sprouting of neurites appears in uninjured MPG/CN treated with PBS, in several discreet regions of the MPG. With SHH treatment, neurite formation increased 114% (FIG. 15C), in a wide area of the MPG and CN, and neurites were 82% longer. Arrows indicate neurites. MPG=major pelvic ganglia. CN=cavernous nerve. 60-160× magnification (FIG. 15B) The CN was crushed, and after three days, the MPG and CN were isolated and grown in organ culture for three days with 1×PBS (control) or SHH protein. Abundant neurites appeared in the crushed MPG/CN treated with PBS. With SHH treatment, neurites increased 49% (FIG. 15D), were 40% longer, and appeared over a 76% wider area of the MPG and CN (red arrows). White arrows indicate neurites. Red lines represent enlarged regions 80× magnification.

SHH Protein Promotes Neurite Formation in Uninjured MPG/CN Neurons:

Organ culture was performed on MPG/CN taken from uninjured Sprague Dawley rats and tissues were treated with PBS (control) or SHH protein. Control MPG/CN showed limited sprouting from neurons in the caudal portion of the MPG (region which innervates the penis) and CN (FIG. 15A). Arrows indicate growing neurites. SHH protein treatment caused abundant and extensive sprouting over a wide area (FIG. 15A). Neurites were quantified by counting the number of growth cones visible in highly enlarged photographs of entire MPG/CN tissues (FIG. 15A insert). This made the growth cones easily visible for counting. The number of sprouts increased 2.1-fold (114%, p-value=0.043), with SHH treatment (FIGS. 15A and C). The average length of sprouts was also quantified in U. SHH protein treatment increased the length of sprouts 1.8-fold (82%, PBS=178 8±47.2, SHH=326.1±33 5, p-value=0.02).

Figure 15B:
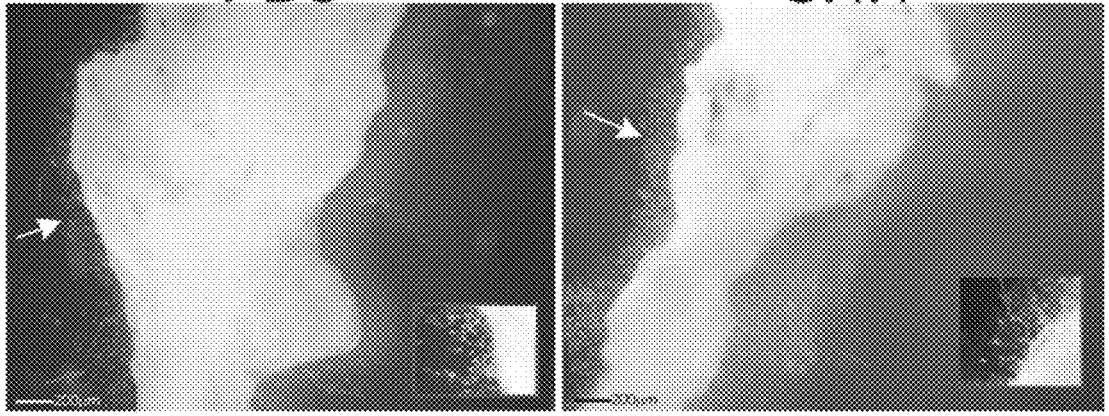
Figure 15C:
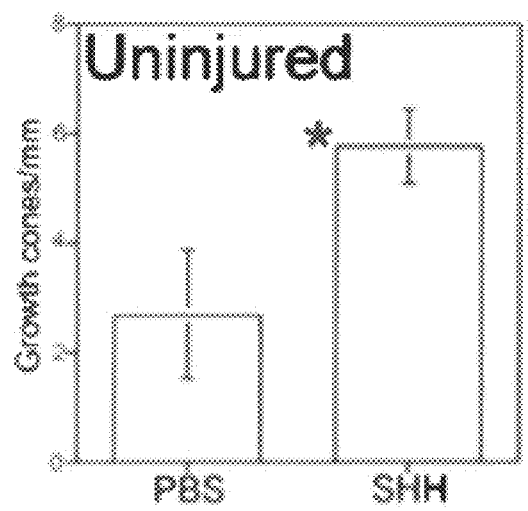
Figure 15D:
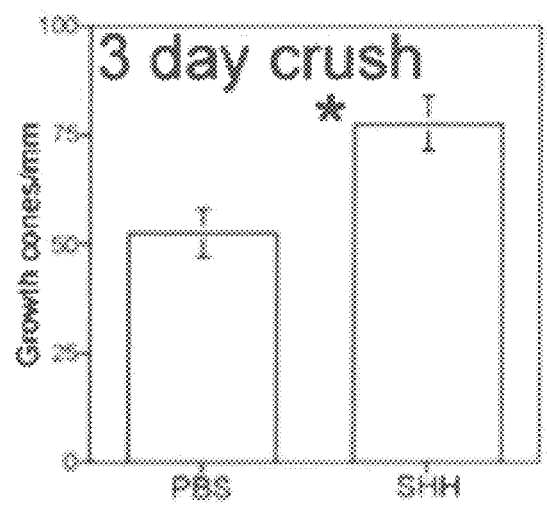

SHH Treatment Enhanced Neurite Formation in Crushed CNs:

Organ culture was performed on MPG/CN taken from Sprague Dawley rats that underwent bilateral CN crush and were isolated after three days and grown in organ culture with PBS or SHH protein delivered via AffiGel beads. Controls showed abundant neurite formation with CN injury (FIG. 15B). SHH protein treatment caused more abundant and extensive neurite formation. The number of neurites increased 1.5-fold (49%, p-value=0.013) with SHH treatment (FIG. 15D). Neurites were 1.4-fold longer (40%0, red arrows) with SHH treatment (Median PBS=216.3, interquartile range=57.7, Median SHH=303.6, interquartile range=240.7, p=0.048, FIG. 3B) and neurites appeared over a 1.8-fold (760%) wider area with SHH treatment (PBS=3.74±0.23, SHH=6.57±0.57, p=0.003).

SHH Inhibition Suppressed Neurite Formation:

Uninjured MPG/CN were grown in organ culture for three days with Affi-Gel beads delivering SHH inhibitors (cyclopamine or 5e1) or control treatments (DMSO, vehicle for cyclopamine, or PBS, FIG. 16A and FIG. 16B). Cyclopamine targets the smoothened part of the SHH receptor, while the 5e1 inhibitor prevents binding of SHH to Patched. Both SHH inhibitors caused a reduction of neurites near the 225 bead vehicles (FIG. 16A, 16B), with neurite formation reduced by 5.6-fold (82%, p-value=0.001) with cyclopamine, and 7.3-fold (86%, p-value=0.00003) with 5e1 antibody (FIG. 16C).

Neurite Formation after CN Injury:

MPG/CN underwent CN crush and were isolated 0, 2, 4 and 9 days after injury and grown in organ culture for 4 days. Neurites were observed at all time points after injury, with most abundant neurite formation after 2 days (FIG. 17A, FIG. 17B). While less abundant, neurite formation was possible at later time points, with similar neurite sprouting potential observed at 4 and 9 days (FIGS. 17A-17B).

Figure 18A:
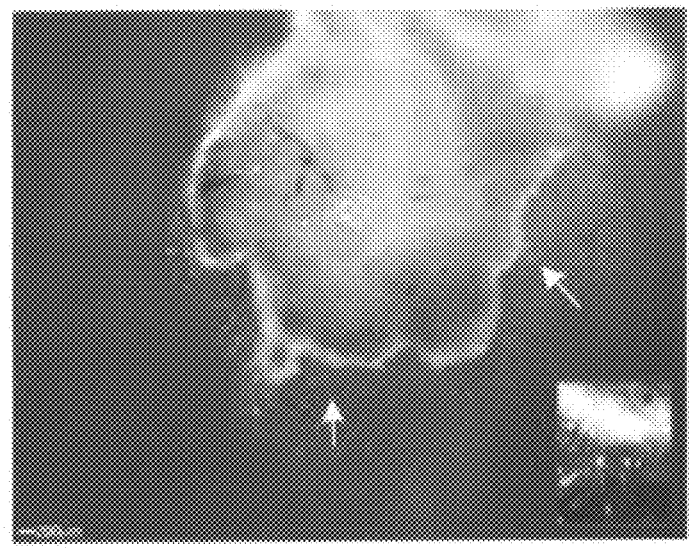
FIGS. 18A-18E. Adult Sprague Dawley rats underwent bilateral CN crush and were treated with either SHH protein or MSA (control) protein via peptide amphiphile (PA) nanofiber hydrogels, which delivered protein for 4 days in vivo and then in in vitro organ culture after isolation of the MPG/CN.
Figure 18B:
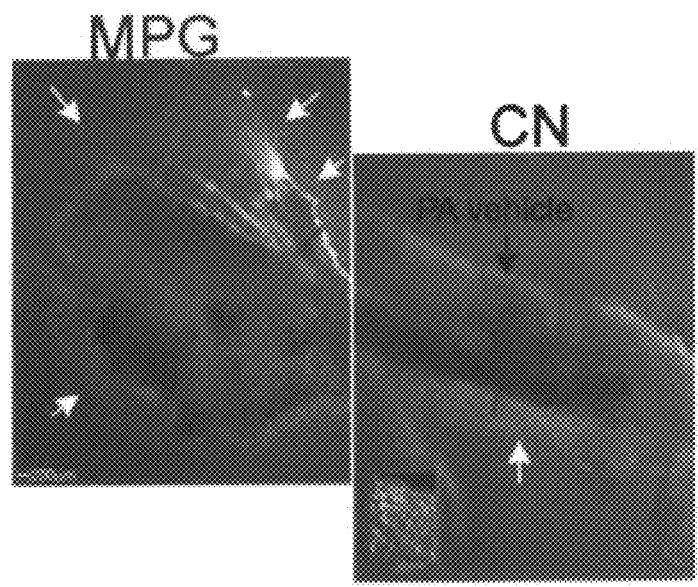
Figure 18C:
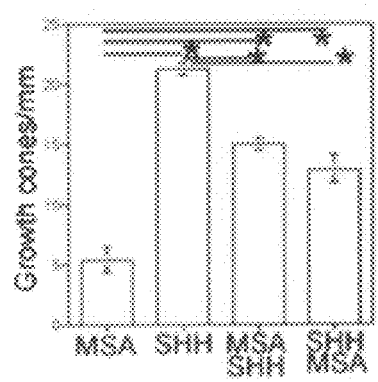
Figure 18D:
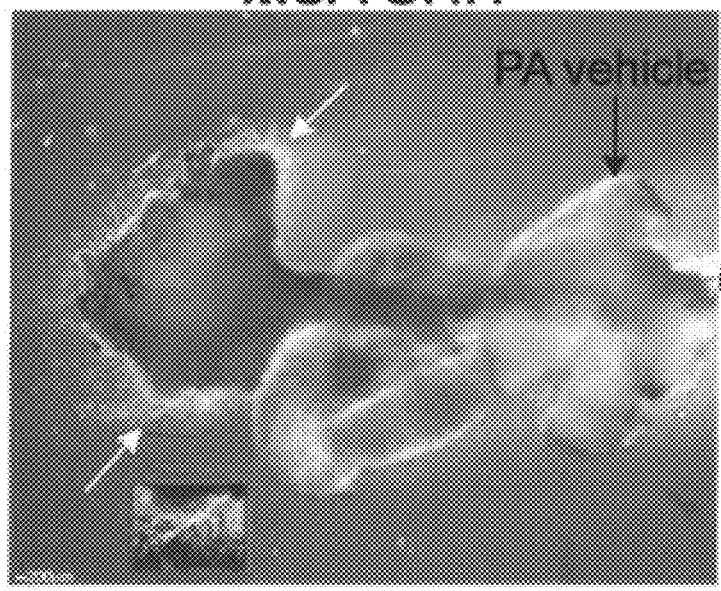
Figure 18E:
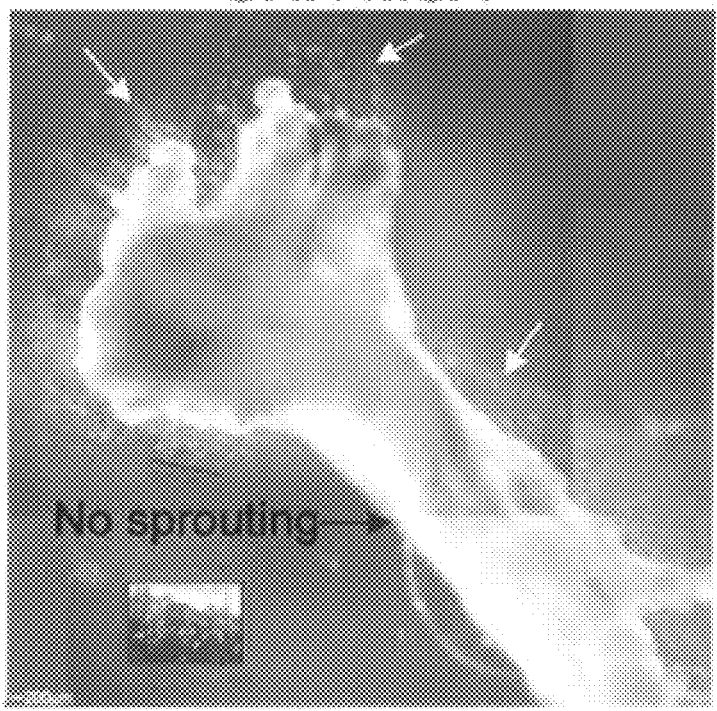

SHH Treatment by PA Promotes Abundant Neurite Formation:

Sprague Dawley rats underwent CN crush and were treated with SHH or MSA (control) protein in vivo for four days by PA. Isolated MPG/CN were grown in organ culture an additional four days with SHH or MSA protein delivered by PA. Little neurite formation was observed with MSA treatment (FIG. 18A), while SHH treatment (FIG. 18B) induced intense neurite formation in a wide area, with neurites increasing by 4-fold (298%, p-value=0.0001, FIG. 18C). SHH protein was able to rescue neurite sprouting potential, with an increase of 2.8-fold (181%, p-value=0.0001) in the number of neurites, after being withheld initially (FIG. 18D). When SHH was given immediately, and then withheld, neurites increased 2.4-fold (141%, p-value=0.0001), and continued to grow once initiated (FIG. 18E).

Figure 19A:
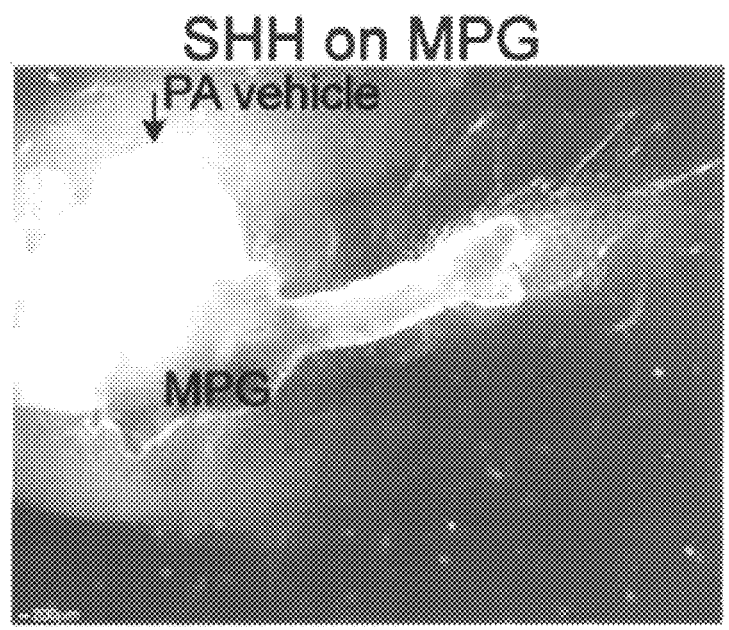
FIGS. 19A-19B: When SHH protein was delivered by PA to the MPG (FIG. 19A), neurites were abundant along the MPG and CN and neurites appeared longer in length, particularly along the severed end of the CN (FIG. 19B) in comparison to CN delivery (FIG. 7B). MPG=major pelvic ganglia. Line indicates length of sprouts. 50-160× magnification.
Figure 19B:
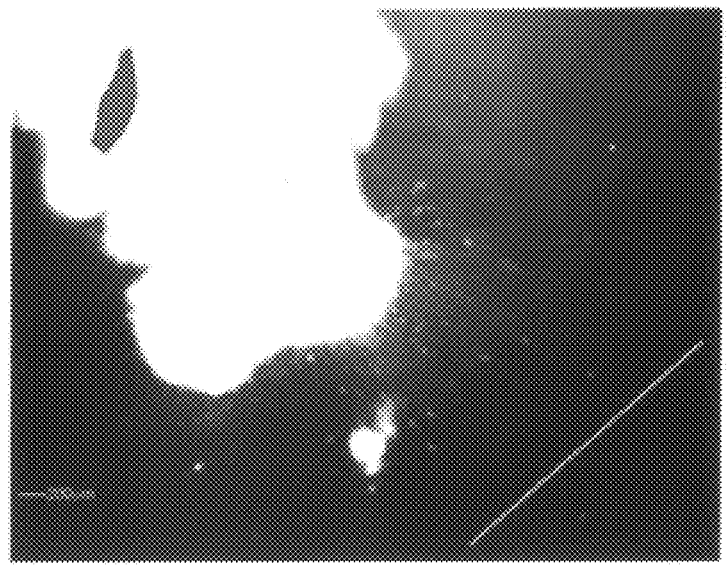

Location of SHH Delivery Influences Neurite Formation:

When SHH was delivered by PA to the MPG (FIG. 19A), neurites were abundant along the MPG and CN and neurites appeared longer in length, particularly along the severed end of the CN (FIG. 19B) in comparison to CN delivery (FIG. 19B).

DISCUSSION

SHH is an important regulator of neurite formation (axonal sprouting) of peripheral neurons, under uninjured homeostatic conditions and under regenerative conditions observed after prostatectomy surgery, with aging, and with peripheral neuropathy in diabetic patients. The number of neurites was increased with SHH treatment, as well as the length of neurites and the area over which sprouts form. Sprouting of neurons that innervate the penis was confirmed with identification of nNOS and GAP43 in growth cones and regenerating axons. The regulatory role of SHH in neurite formation, was confirmed with targeted inhibition of the SHH receptors, patched and smoothened [26-28], which severely reduced the number of neurites (>80%). The most robust neurite formation was observed with continuous SHH protein delivery by PA to the crushed CN, which impacted a wide area of MPG/CN, increasing neurites 298%, and sprouts appeared longer Once neurites were induced with SHH treatment, they continued to grow when SHH was withdrawn. When SHH was withheld initially, and not given until four days after injury, neurite sprouting was rescued, with initiation of abundant neurites, though less robust then when SHH was given continuously. These studies identify SHH as an essential regulator of neurite formation in peripheral neurons under normal and regenerative conditions and have important clinical implications for translation. SHH protein abundance decreases in the MPG/CN with CN injury, likely contributing to the poor regenerative response of the CN in prostatectomy and diabetic ED patients and animal models.

The results herein indicate that treatment of the MPG/CN with SHH protein at the time of CN injury/prostatectomy, would be beneficial to enhance neurite formation and regenerate the CN. This would have the added benefit of maintaining downstream morphology of the penis, which is irreversibly altered in response to loss of innervation. While SHH intervention has the most impact when given immediately with crush injury, it can be useful even at a later time to promote regeneration.

Neurite formation in uninjured MPG/CN was not abundant under the low growth factor conditions chosen for this study. This was intentional since growth factors commonly found in Matrigel, such as VEGF, may influence neurite formation, and compromise experimental conditions. Neurite formation was evaluated from 0 to 9 days after CN crush. Neurites were minimal the day of crush injury, and was most abundant two days after injury, suggesting that early responding factors produced during this window of time are critical. At four and nine days after injury, neurites were consistently low, however SHH treatment could induce robust neurite formation at four days after CN injury. The active form of SHH protein decreases in the MPG/CN as early as one day after injury, and similar SHH protein levels were observed at 4 and 7 days. This suggests a window of time when optimal neurite formation can be induced with exogenous signals. These temporal relationships have therapeutic implications should SHH supplementation transition from bench to the bedside.

Location of SHH delivery may contribute to differences in neurite sprouting potential. SHH protein delivered via PA to the crush site, has previously been shown to undergo retrograde transport to MPG neurons that innervate the penis, where SHH maintains signaling between MPG neurons and glia, and prevents neuronal apoptosis. In this study when SHH was applied to the MPG, rather than the CN, neurites formed in a similar manner to CN delivery, however neurites were longer, particularly at the resected portion of the CN, where there was extensive branching. This suggests that SHH delivery to the MPG activates normal neurite sprouting mechanisms more readily so that neurites form more quickly, are longer, and more extensively branched. When thinking about translation to prostatectomy patients, both the CN and MPG are responsive to SHH induction of neurite sprouting, and a treatment program which includes both as SHH targets, would be beneficial to promote regeneration and preserve erectile function.

Example 4

Optimization of Sonic Hedgehog Delivery to the Penis from Self-Assembling Nanofiber Hydrogels to Preserve Penile Morphology after Cavernous Nerve Injury Erectile dysfunction (ED) is a significant health concern, that effects 50% of men aged 40 to 70 and 22% under 40. ED has high impact on men's quality of life and health, and develops when the cavernous nerve (CN), which innervates penile tissues, is damaged at the time of radical prostatectomy surgery, and with peripheral neuropathy in aging and diabetic patients. Loss of innervation causes intensive, irreversible alterations to the architecture of the corpora cavernosa of the penis, including abundant apoptosis of smooth muscle, and increased collagen, resulting in ED. Current treatments, such as PDE5i, are not effective in up to 69% of patients with ED and cavernous nerve injury, including 82% of radical prostatectomy and 59% of diabetic patients, so novel therapies are needed which target this difficult to treat population.

The present example demonstrates the use of nanoscale self-assembling peptide amphiphile (PA) hydrogels to deliver SHH protein to the penis and CN in order to accelerate CN regeneration, suppress apoptosis in the penis, and improve erectile function. In particular, this study demonstrates optimization of the CN injury model to more effectively parallel the majority of radical prostatectomy patient injury, the concentration of SHH protein delivered, the duration of apoptosis suppression, and simultaneous distribution of SHH to the penis and CN. Optimization is examined by quantifying changes in penile morphology, with decreased apoptosis and preserved smooth muscle indicative of more normal penile morphology and preserved function.

Methods

Animals:

Ninety-seven Sprague-Dawley rats were obtained from Charles River. The rat age was between postnatal day 115-120 (P115-P120). The study was performed according to the recommendations outlined in the Guide for the Care and Use of Laboratory Animals of the National Institutes of Health and the Office of Animal Care, and Institutional Biosafety at the University of Illinois at Chicago approved the protocol.

Surgical Procedures for CN Crush (Bilateral) and Sham Surgeries:

After exposing the PG/CN, it was crushed for 30 seconds (mild crush) using microforceps (0.02×0.06 mm). This CN crush methodology is routinely used in the literature and the reproducibility and extent of injury were previously defined in our laboratory. Control (sham) surgical procedures were performed by exposing and identifying the CN without performing crush injury. Rats were sacrificed 4 and 9 days post injury. Severe crush injury (3 consecutive 30 second crushes, n=4) and CN resection (removal of a 5 mm portion of the CN>5 mm from the pelvic ganglia, n=4) were also performed to examine the effect of injury severity on the apoptotic index, and rats were sacrificed 4 days after damage.

Peptide Amphiphile (PA) Delivery of SHH Protein to the Penis for 4 Days after CN Injury:

CN damage was performed as cited in the previous section. $V_3A_3E_3$-COOH PA hydrogel was used to deliver either SHH (n=5) or mouse serum albumin (MSA, control, n=4) proteins to the penis. Briefly $V_3A_3E_3$-COOH PA (50 μl of a 20-mM solution), SHH or MSA protein (5 μl of a 1.25 μg/μl solution, R&D Systems, Minneapolis, Minn., USA) and $CaCl_2$ (50 μl of a 40 mM solution) were injected directly into the corpora cavernosa of the penis. The penis was exposed, a silk tourniquet was fixed at the proximal portion of the penis, and PA was injected with a 26-gauge needle (1-5 μl volume) directly into the distal portion of the corpora cavernosa. The PA gelled within 30 seconds to 1 minute, forming a thin layer coating the sinusoidal spaces. Final PA concentration was 10 mM, $CaCl_2$ was 20 mM, and SHH protein was 6.25 μg per rat (1×) or 2× (n=5). Additional rats underwent sham (n=6) and CN crush (n=6) surgeries. Penises were removed by sharp dissection from euthanized males 4 days after SHH protein/PA/$CaCl_2$ injection and were snap frozen in liquid nitrogen.

CN Injury with Increased Duration of SHH PA Treatment of the Penis for 9 Days:

CN crush injury was performed as described above and rats were injected immediately with SHH or MSA/bovine serum albumin (BSA, control) PA as described above. At day 5, when SHH protein was largely depleted from the PA as it lost its structural integrity, a second SHH (n=8) or MSA/BSA (n=7) PA injection was performed and rats were sacrificed after an additional 4 days (9 days total since CN crush surgery). An additional group that had been given one SHH PA injection at the time of CN crush was sacrificed after 9 days without further intervention (n=4). Sham (n=5) and CN crush (n=5) were also performed for comparison.

CN Crush Injury with Simultaneous Delivery of SHH PA to the Penis and CN for 4 Days:

CN crush injury (bilateral) was performed and rats were immediately injected with SHH (n=7) or MSA (control, n=4, 1 μg/μl) PA into the corpora cavernosa as described above. Following injection into the penis, SHH or MSA was delivered bilaterally to the CN using a second type of PA15. The highly-aligned "noodle" PAs used for CN protein delivery were made by heating a 100 mM solution of $V_2A_2E_2NH_2PA$ to 80° C. (30 minutes), and slowly cooling to room temperature. SHH protein (2.27 μg in 1.5 μl volume) was added to 8.5 μl PA, immediately prior to use in the animal. 500 μl 20 mM $CaCl_2$) was placed on a slide, and cooled PA/SHE mixture was slowly expressed through a pipet tip, into the $CaCl_2$) solution, forming a noodle-like hydrogel that could be laid on the exposed CN.

Apoptotic Index:

Apoptosis was quantified using the Apoptag kit (Millipore) on penis tissue that was frozen, cut 11 μM in thickness, and the tissue was post fixed in acetone for 15 minutes at 4° C. DAPI (0.005 μg/ml) was used to stain all cells for comparison. Fluorescence was observed using a Leica DM2500 microscope. Photography was performed using a Qicam 1394 digital camera. The apoptotic index (apoptotic cells/all cells) was determined by counting the number of apoptotic cells and all cells in five fields from each section and five sections per penis and was reported ±standard error of the mean.

Trichrome Stain:

Trichrome stain of penis tissue was performed and quantified by Image J (version 1.45 s, down load date May 22, 2012). The area of smooth muscle (red) and collagen (blue) were quantified individually in trichrome photos after background subtraction. Smooth muscle and collagen were quantified in 25 photos (200×) from each penis tissue that were selected randomly (5 photos per section and 5 sections per penis tissue).

PA Delivery of SIM or BSA (Control) Protein to the Penis:

Sprague Dawley rats (P120) were randomly assigned to two groups: CN resection (bilateral) with either SHH PA injection into the penis (n=12), or with BSA (control) (n=11). Penises were removed at 2, 4, and 7 days after injury, by sharp dissection.

Quantification of Proliferation:

The proliferative index was quantified in penis tissue treated with SHH (n=9) or BSA (n=9) protein by PA, by counting Ki67 stained cells and all cells which were stained with DAPI (0.005 μg/ml). Stained cells were observed with a fluorescent microscope (Leitz) and were photographed with a digital camera (Nikon). The number of proliferating cells/all cells was reported from five fields in each section and five sections per penis and was reported ±the standard error of the mean.

Immunohistochemical Analysis (IHC):

Dual staining using fluorescent IHC for Ki67/CD31 (endothelial marker) and Ki67/α-ACTIN (smooth muscle marker) were performed as described previously 11 assaying for 1/50 goat Ki67 (Santa Cruz, SC7846), 1/100 mouse α-ACTIN (Sigma, A-5691) and 1/100 mouse CD31 (Millipore, MAB1393). Alexa Fluor 488 chicken anti-goat (1/150), and Alexa Fluor 594 donkey anti-mouse (1/350, Molecular Probes) were used as secondary antibodies.

Statistical Analysis:

Statistics were performed by ANOVA with a Scheffe's posthoc test using the SSPS statistical program or using a Student's t-test. Differences were significant when p<0.05.

Results

Figure 20A:
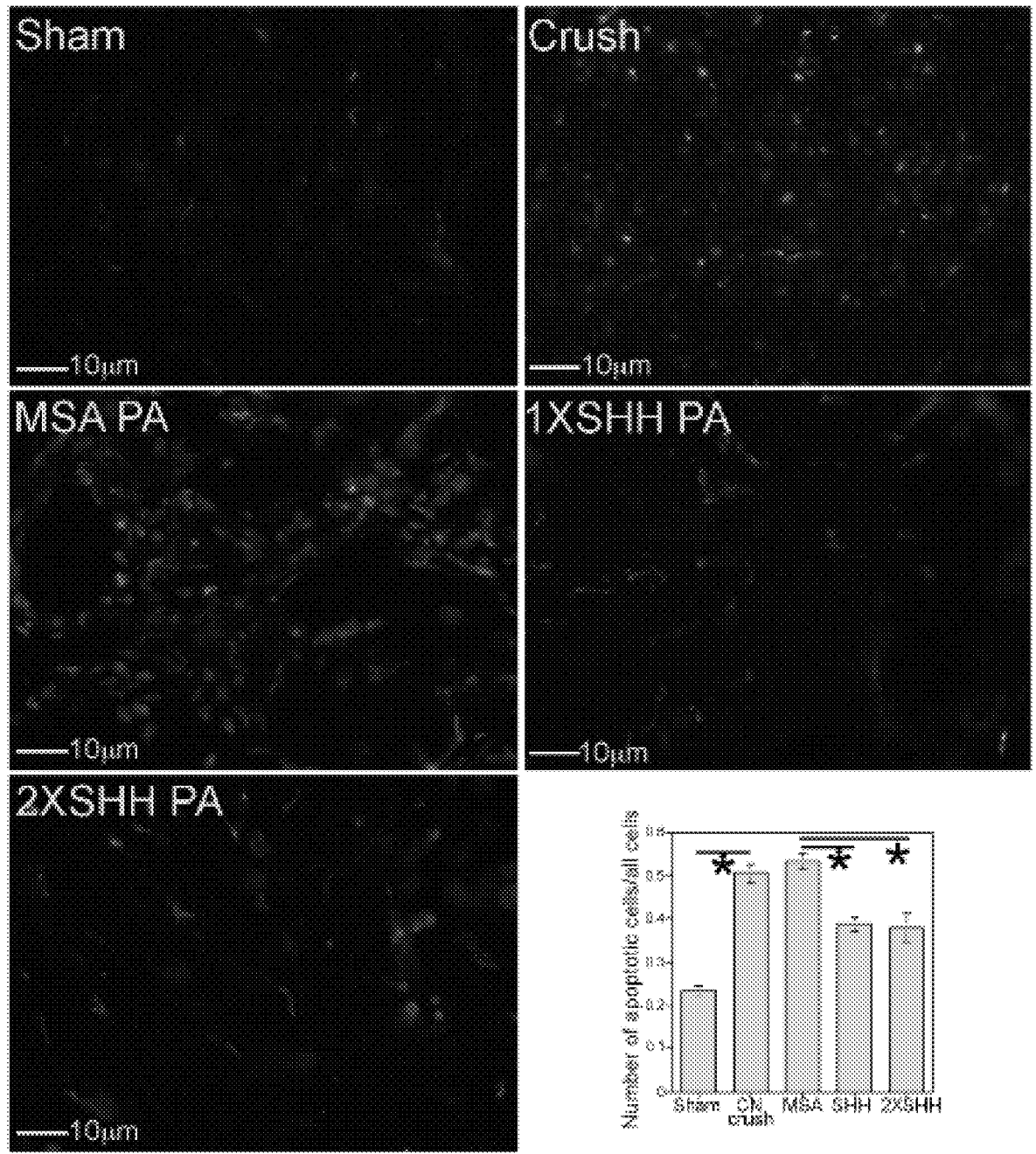

PA Delivery of SHH Protein to the Penis for 4 Days after CN Injury:

The PA ($V_3A_3E_3$-COOH) with SHH protein undergo targeted injection into the corpora cavernosa of the penis with subsequent gelation of the PA in vivo in the corpora cavernosa. It forms as a soft gel layer along the surface of the corpora cavernosal sinuses. SHH protein is enmeshed in the hydrogel as it forms during cation-based assembly and crosslinking, and is released as the PA breaks down. With the advent of nerve sparing techniques, the majority of radical prostatectomy induced injury derives from CN crush and manipulation of the PG/CN. The PAs were applied here in a CN crush ED model to examine if SHH protein released by PA in vivo in the penis, suppresses the apoptotic index (ratio of apoptotic cells/all cells stained with DAPI) and collagen induction. The SHH concentration delivered for maximal apoptosis suppression was also optimized, with two concentrations being examined. The apoptotic index is elevated for tissue injury/death, and decreases with effective therapeutic delivery. The apoptotic index increased 117% 4 days after CN injury (n=6) relative to sham controls (n=6, p=0.0001, FIG. 20A). SHH PA (n=5) suppressed apoptosis 27% in comparison to MSA PA (n=4) treated controls (p=0.005, FIG. 20A). Doubling the SHH protein concentration given to the penis (2×, n=5) decreased the apoptotic index 29% (p=0.003), which was not significantly different apoptosis suppression than the 1×SHH treatment group (p=0.999, FIG. 20A). Trichrome stain quantification of smooth muscle showed 48% more smooth muscle in the 1×SHH treated group (n=5) compared to MSA treated controls (n=4, p=0.005, FIG. 20B). Doubling the concentration of SHH (2×, n=5) resulted in 76% more smooth muscle than in MSA treated controls (p=0.0001, FIG. 20B). No significant difference in smooth muscle was observed between the 1× and 2×SHH treated groups (p=0.066, FIG. 20B), likely resulting from differences in distribution or break down of the PA in the penis, which would effect the SHH release rate. Since sheer stress within the sinusoidal lining where the PA forms may vary from penis to penis depending on the erectile state of the animal over several days during delivery, this can induce variability in apoptotic suppression and smooth muscle preservation which make reliable quantification of penile smooth muscle by western analysis challenging. Trichrome stain quantification of collagen showed 26% less collagen in the 1×SHH treated group (n=5) compared to MSA treated controls (n=4, p=0.002, FIG. 20C). Doubling the concentration of SHH (2×, n=5) resulted in 32% less collagen than in MSA treated controls (p=0.0001, FIG. 20C). A significant difference in collagen abundance was not observed between the 1× and 2×SHH treated groups (p=0.522, FIG. 20C).

Figure 21A:
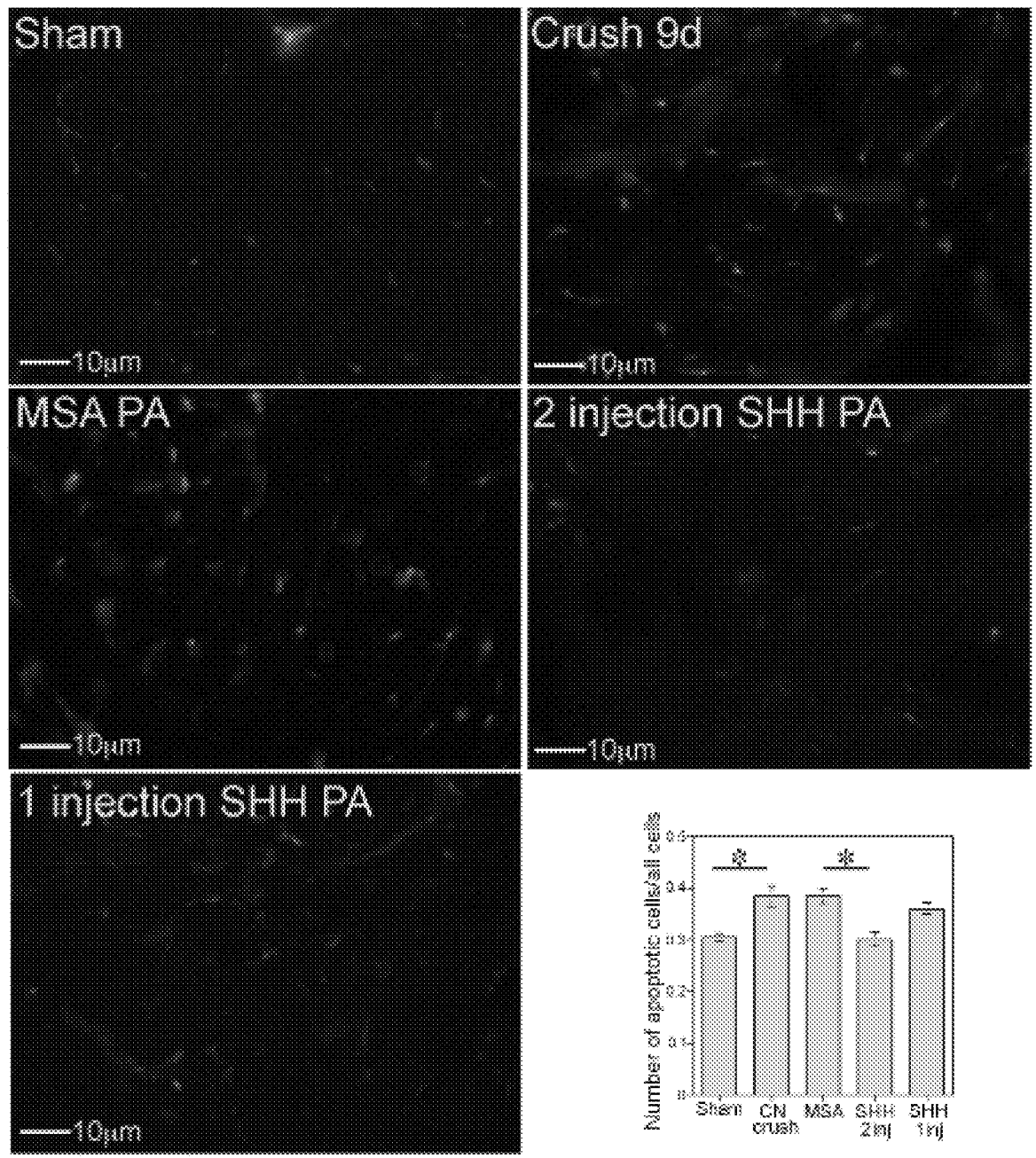
FIGS. 21A-21C.
Figure 21B:
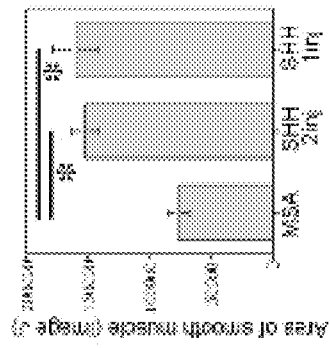
Figure 21B:
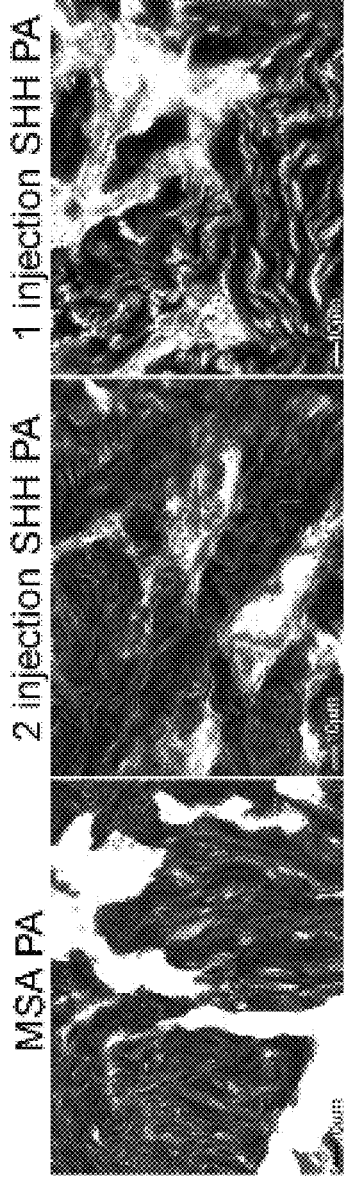
Figure 21C:
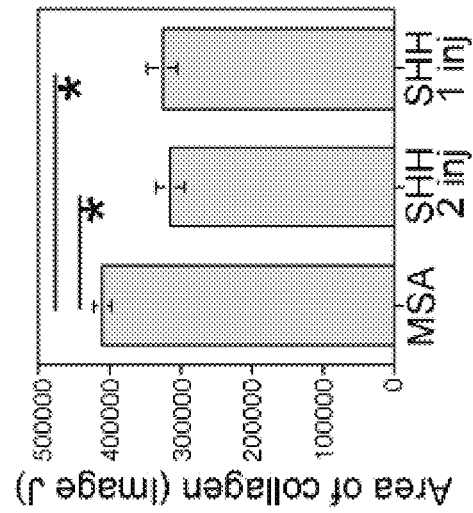

CN Injury with Increased Duration of SHH PA Treatment of the Penis for 9 Days:

In order to examine how long SHH PA injection can suppress apoptosis, if apoptosis is suppressed or delayed with SHH treatment, and to examine if multiple SHH PA injections would be advantageous to suppress apoptosis for a longer time after CN injury, CN crush was performed with SHH or MSA/BSA PA injection at time of surgery. A second SHH and MSA/BSA PA injection was performed at five days after injury, and rats were sacrificed nine days post CN crush. The apoptotic index was increased 26% at 9 days after CN injury (n=5) in comparison to sham (n=5, p=0.014, FIG. 21A). Two SHH protein PA injections (n=4) caused a 22% reduction in apoptosis at 9 days after CN crush in comparison to two MSA/BSA PA injections (n=4, p=0.021, FIG. 21A). Rats that had been given only one SHH PA injection (n=4) and were sacrificed at 9 days after CN crush, had apoptotic levels that were not significantly different than untreated CN crushed rats at 9 days post injury (p=0.830, FIG. 21A), indicating that once SHH protein is depleted from the PA, the corpora cavernosal tissue reverts to the apoptotic level that occurs at that time post injury, thus avoiding the initial bolus of apoptosis that occurs in the first few days (2-4 days) after injury. Trichrome stain quantification of smooth muscle showed 100% more smooth muscle in the two SHH injection group (n=7) compared to MSA controls (n=7, p=0.001, FIG. 21B). With one SHH injection (n=4), 110% more smooth muscle was present in comparison to MSA treated controls (p=0.001, FIG. 21B). The one and two SHH injection groups were not significantly different from each other with regard to smooth muscle preservation (p=0.921, FIG. 21B). Trichrome stain quantification of collagen showed 24% less collagen in the two SHH injection group (n=7) compared to MSA treated controls (n=7, p=0.003, FIG. 21C). With one SHH injection (n=4), 21% less collagen was present in comparison to MSA treated controls (p=0.022, FIG. 21C). The one and two SHH injection groups were not significantly different from each other with regard to collagen preservation (p=0.919, FIG. 21C).

Figures 22A, 22B:
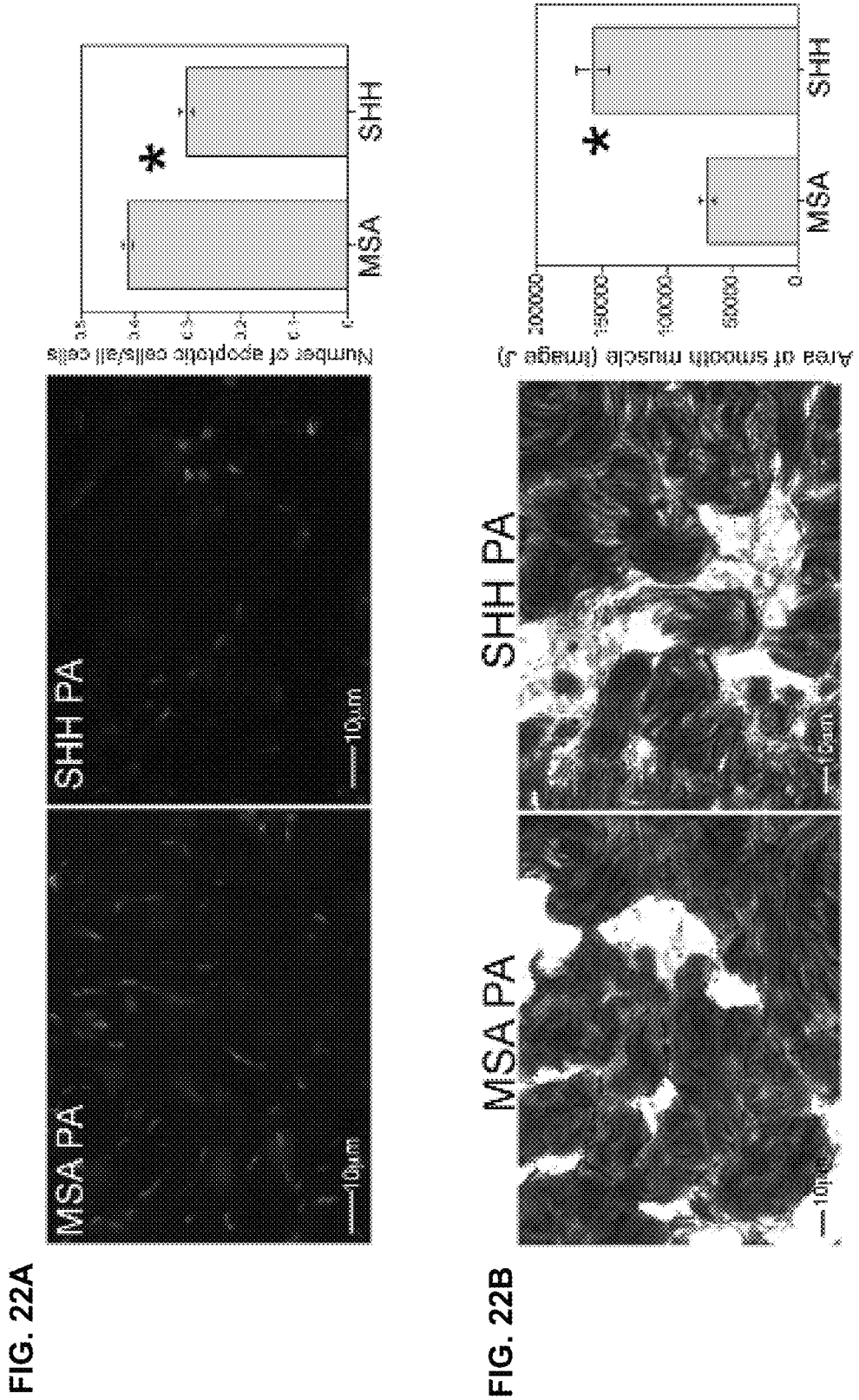
FIGS. 22A-22C.
Figure 22C:
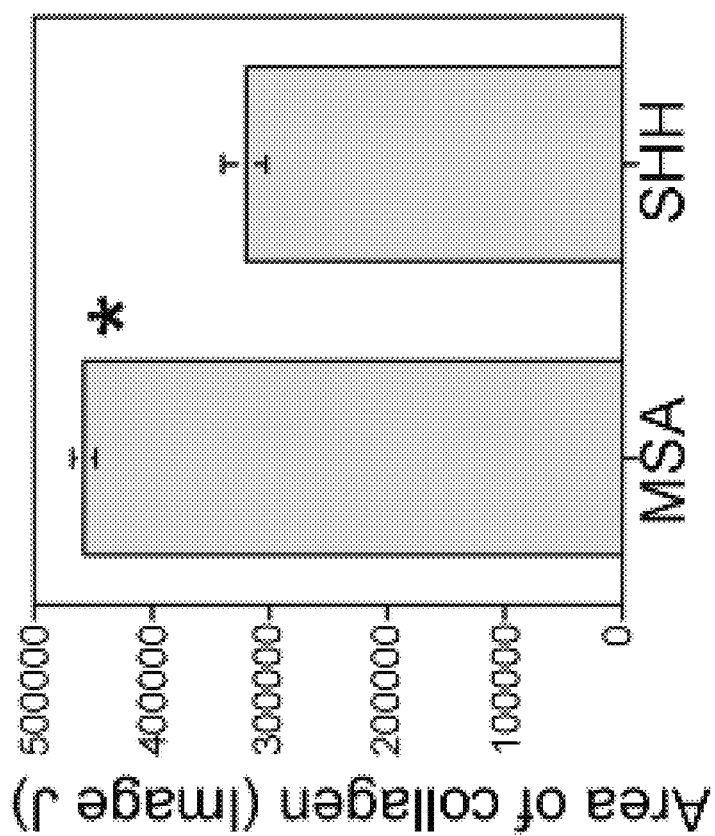

CN Crush Injury with Simultaneous Delivery of SHH PA to the Penis and CN for 4 Days:

Potential additive effects on suppression of morphology changes in the penis with simultaneous SHH distribution to the penis and CN, were examined. When SHH (n=7) or MSA (control, n=4) protein were delivered by PA into the penis and CN concurrent with CN injury, the apoptotic index decreased 27% 4 days after injury with SHH treatment in comparison to MSA controls (p=0.0001, FIG. 22A). Trichrome stain quantification of penile smooth muscle showed 127% more smooth muscle in the rats treated with SHH in the penis and CN (n=7) versus MSA treated controls (n=4, p=0.0004, FIG. 22B). This was the highest smooth muscle preservation observed in all groups examined. Trichrome stain quantification of penile collagen showed 30% less collagen in the rats treated with SHH in the penis and CN (n=7) versus MSA treated controls (n=4, p=0.0003, FIG. 22C).

Figure 23:
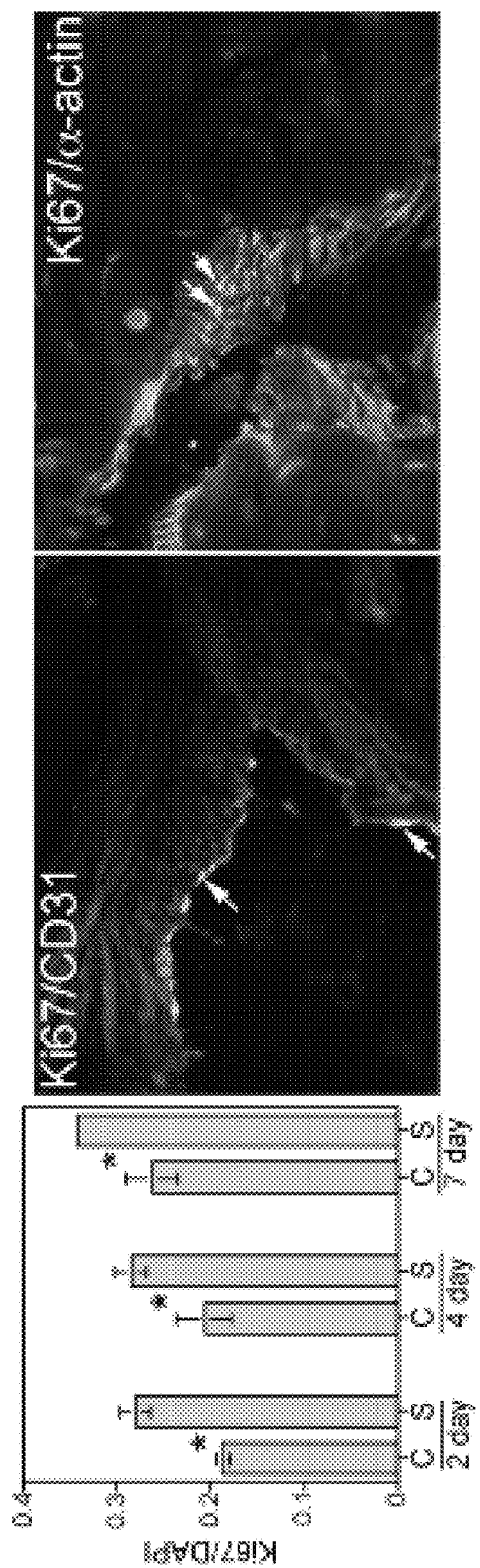
FIG. 23. Proliferative index (Ki67/DAPI) quantified in SHH and BSA (control) PA treated penis, shows increased proliferation at 2, 4 and 7 days of SHH treatment (p=0.003, p=0.042, and p=0.022). Co-localization of Ki67(green)/CD31 (red) and Ki67(green)/α-ACTIN (red), indicate proliferation in smooth muscle and endothelium FIG. 24. Apoptotic index was quantified on penis tissue from rats that underwent sham, mild or severe crush, or CN resection (4 days). Apoptosis increased 117%, 119% and 125% for mild and severe crush, and CN resection, relative to sham controls (p=0.0001). There was no difference in apoptosis between the injury groups.

Quantification of Proliferation in CN Injured Penis at 2, 4 and 7 Days Post Injury:

The proliferative index Ki67 (proliferation marker)/DAPI (stains all cells) was quantified in corpora cavernosal tissue from Sprague Dawley rats that had bilateral CN injury and either SHH (n=9) or BSA (control, n=9) PA injection into the corpora cavernosa at the time of injury. Tissues were examined at 2, 4 and 7 days after injury. SHH PA treatment increased the proliferative index 50% (p=0,003) at two days after injury, 38% (p=0.042) at 4 days after injury, and 31% (p=0.022) at 7 days after injury (FIG. 23). Dual IHC analysis for Ki67/CD31 and Ki67/α-ACTIN show that proliferation is taking place in both smooth muscle and endothelium (FIG. 23).

Figure 24:
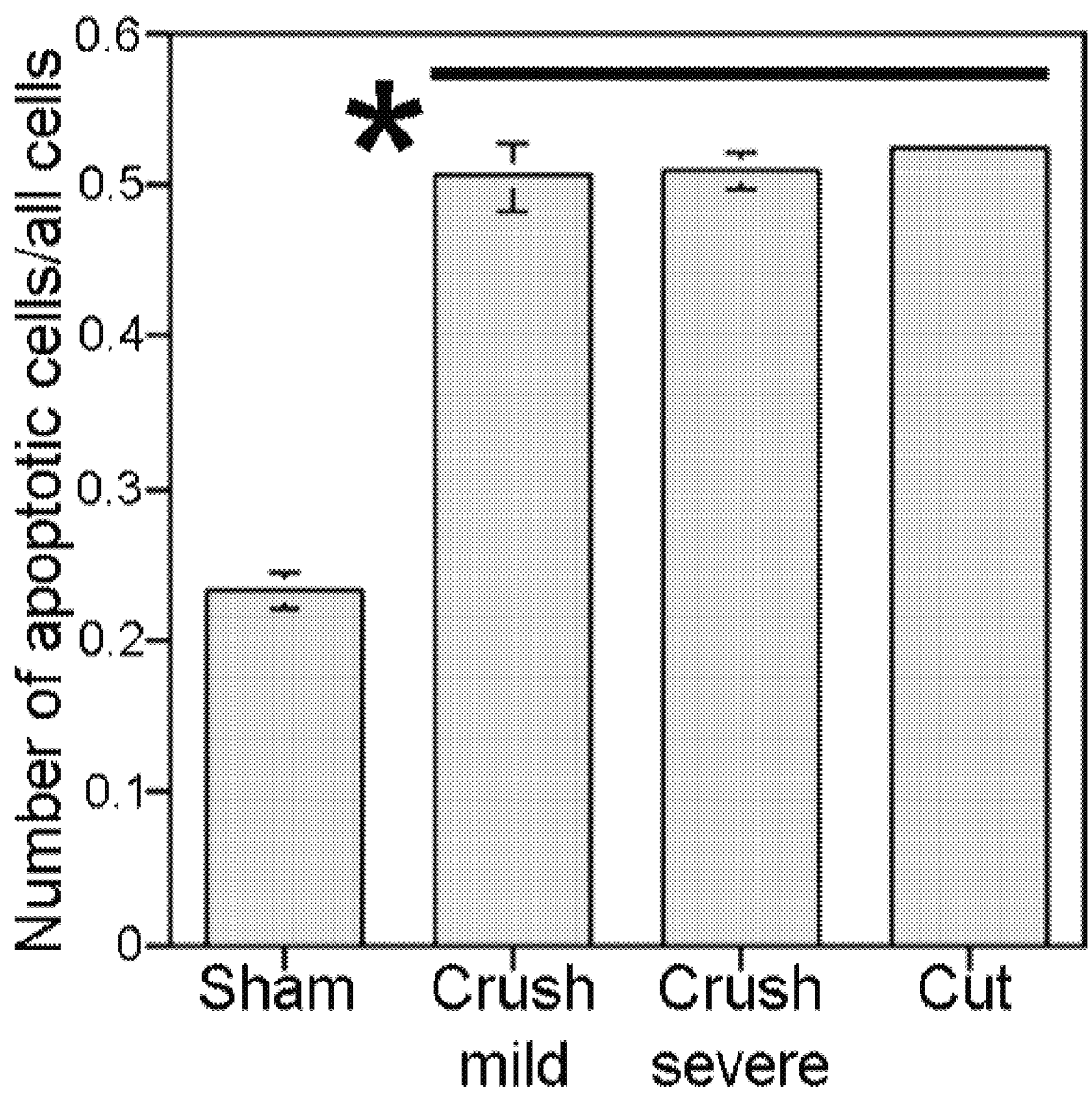

Effect of Severity of CN Injury on Penile Apoptotic Response:

The apoptotic index was quantified by TUNEL assay on penis tissue from rats that underwent, sham, mild CN crush, severe CN crush or CN resection injury, and tissues were assayed 4 days after CN damage. The apoptotic index increased 117%, 119% and 125% for mild crush, severe crush, and CN resection, relative to sham controls (p=0.0001, FIG. 24). There was no difference in the apoptotic index between the mild and severe CN crush and CN resection groups, indicating an all or nothing response of the penis to loss of innervation (mild to severe p=0.996, mild to resection p=0.894, severe to resection p=0.979, FIG. 24).

DISCUSSION

This study examines development of a nanoparticle-based vehicle for sonic hedgehog protein delivery to the penis to preserve penile morphology and regenerate erectile function after cavernous nerve (CN) crush injury (radical prostatectomy model). It is shown that optimization of sonic hedgehog delivery conditions by peptide amphiphile (PA) nanofiber hydrogel increases smooth muscle preservation 80%, with implications towards preservation of erectile function. CN crush is the most common injury that occurs during radical prostatectomy, however CN neuropathy also occurs in diabetic and aging patients, with parallel changes observed in penile morphology and sonic hedgehog signaling, suggesting potential SHH PA application in these difficult to treat ED populations. Optimization of sonic hedgehog delivery is indispensable for clinical translation to radical prostatectomy patients to impede erectile dysfunction. This work shows the importance of SHH signaling in preserving the smooth muscle morphology of the penis after CN injury, which is critical for preservation of erectile function. Suppression of smooth muscle apoptosis and accelerated CN regeneration, are key components required for development of ED therapies. SHH delivery by PA, both within the corpora cavernosa as a thin interior lining adjacent to the smooth muscle and endothelial tissue, and adjacent to the injured CN via a PA "noodle", offers a dual approach to addressing two key mechanisms of ED progression. PAs are particularly attractive for eventual clinical application as they provide extended release of protein, are biodegradable, and are readily produced by synthetic means and versatile enough that both modalities (injection as an aqueous hydrogel precursor, or physical deposition along the CN) are feasible clinical steps, post-prostatectomy.

Clinical advances toward nerve-sparing procedures have shifted CN injuries from full resections to partial physical damage ("crush"). In this study it was examined if SHH delivered by PA to the penis at the time of CN crush (mimicking radical prostatectomy induced injury) suppresses the morphological changes that occur in the corpora cavernosa of the penis in response to loss of innervation. These include induction of apoptosis, primarily in penile smooth muscle, followed by increased collagen deposition. The corpora cavernosal remodeling is significant and may result in loss of physiological function/erectile function. It is shown herein that apoptosis is suppressed 27% in response to SHH PA treatment at four days after CN injury, a time when apoptosis induction is most abundant in response to loss of CN innervation. SHH PA treatment has the added benefit of suppressing collagen induction (26%), which leads to penile fibrosis and a less compliant penis. Doubling the concentration of SHH protein did not further suppress the apoptotic index. This can occur because the original concentration is in the target range for optimal SHH suppression of apoptosis, there is a threshold above which further addition of SHH does not further improve penile morphology, or may result due to technical challenges in vivo with the PA such as variation in PA break down due to differences in sheer stress between rats, and limitations of targeted PA injection into the corpora cavernosa of the rat. In patients, the penis tissue is much larger and targeted injection into the corpora cavernosa is not a difficulty. Dampening the intensity of the early apoptotic response is critical to preserving smooth muscle and erectile function.

The time course of apoptosis that occurs in the rat penis in response to CN resection and CN crush, have been documented. For the more severe case of CN resection, apoptosis peaks at 2 days after CN injury, begins decreasing at 7 days after injury, and remains barely detectable above baseline from day 14-60 post injury. For CN crush, apoptosis induction is slower with a peak at 4 days after injury, and decreases significantly by 7 days, and returns to baseline by 14 days post crush injury. In this study a 117% increase in apoptosis at 4 days after bilateral CN crush is shown. The apoptotic index was reduced to 26% by 9 days after CN injury. Indicating that the majority of apoptosis occurs in the first few days after injury and if this could be prevented, than the majority of penile remodeling would be avoided, and thus erectile function preserved. When one SHH PA injection was given at the time of CN injury, apoptosis was suppressed until SHH was depleted from the PA. Addition of a second SHH PA injection, maintains apoptosis suppression longer, however smooth muscle preservation was not statistically different with one and two SHH PA injections. This likely occurs because apoptosis in the rat after CN crush injury is most abundant 2-4 days after injury and then remains only slightly elevated above baseline between 7 and 14 days. One SHH PA injection may thus be sufficient to suppress most of the apoptotic response and preserve smooth muscle. A similar trend was shown with suppression of collagen with one and two SHH PA injections.

The highest smooth muscle preservation was observed with simultaneous SHH PA treatment of the penis and CN at the time of crush injury. With SHH PA injection into the penis alone, smooth muscle was preserved 48%, versus simultaneous delivery to the CN and penis resulted in 127% more smooth muscle retention at 4 days after injury. This 80% improvement in smooth muscle retention likely results due to direct effects of SHH protein in both locations. The amount of smooth muscle preservation may be high relative to the apoptotic index suppression observed. This may result since the apoptotic response is only quantified at small windows of time post injury. More likely is that SHH PA treatment not only affects the apoptotic response, it also effects proliferation of smooth muscle (FIG. 23). This is a concept that has not previous been explored after CN injury. It is assumed that smooth muscle decreases without the tissue attempting to reestablish itself. In this study it is demonstrated that proliferation occurs in the corpora cavernosa after CN injury, and this response is increased in smooth muscle and endothelium in the presence of SHH PA in the penis. The proliferation that is observed appears to be normal patterned penile architecture, suggesting up-regulation of normal developmental mechanisms in response to SHH. Thus SHH protein treatment of the penis by PA both suppresses smooth muscle apoptosis and increases proliferation.

Collagen deposition was 20-30% lower in all SHH treated groups after CN crush in comparison to controls. It is unclear how this suppression of collagen induction occurs. It is possible that morphological remodeling that results in the penis in response to loss of innervation is an orchestrated process, with smooth muscle apoptosis occurring prior to increased collagen induction. For CN crush, the majority of apoptosis occurs 2-4 days after injury and decreases by 7 days. Collagen is not measurably increased until 7-14 days after CN injury. There is minimal study in this area however cells undergoing apoptosis release factors into the microenvironment that may affect proliferation/morphology in target cells. Further study beyond the scope of this work will be required to understand this remodeling process.

These studies show that SHH PA treatment of the penis and CN reduces apoptosis, preserves smooth muscle, and suppresses collagen induction that occurs in response to CN crush injury. Optimizing the method and duration of PA delivery improved smooth muscle preservation 80%, with implications towards preservation of erectile function. An all or nothing apoptotic response of the penis was observed with loss of innervation, irrespective of the severity of CN damage. CN crush is the most common injury that occurs during radical prostatectomy, however CN neuropathy also occurs in diabetic patients and with aging, with parallel changes observed in penile morphology and SHH signaling, suggesting potential SHH PA application in these difficult to treat ED populations. Optimization of SHH delivery is essential for clinical translation to radical prostatectomy patients to prevent ED and the PA nanofiber vehicle may be widely applicable as an in vivo delivery tool.

Example 5

Sonic Hedgehog Regulation of Cavernous Nerve Regeneration and Neurite Formation in Aged Pelvic Plexus In our tissue bank, the average ED patient age ranges from 52 to 71 years with an average of 61.5±9.6 years. This is consistent with average ED patient ages reported in the literature (Feldman et al., 1994) and is equivalent to 1-2 rat years. In the present example, SHH pathway signing was examined in an aged prostatectomy model that more accurately mimics ED patient conditions. It was hypothesized that if the SHH receptors are intact in aged MPG/CN, that reintroduction of SHH protein to MPG/CN in an aged prostatectomy model would be more effective in promoting CN regeneration (neurite outgrowth) than in the adult. This was examined in organ culture of uninjured, CN crushed, and SHH inhibited MPG/CN.

Methods

Animals:

Adult Sprague-Dawley rats postnatal day 115-120 (P115-P120, n=11) and aged Sprague Dawley rats (P200-P329, n=13) were obtained from Charles River (Wilmington, Mass.). The study was carried out in accordance with the recommendations in the Guide for the Care and Use of Laboratory Animals of the National Institutes of Health. The animal care protocol was approved by the Office of Animal Care and Institutional Biosafety at the University of Illinois at Chicago and animals were cared for in accordance with institutional approval.

CN Crush Surgery:

MPG/CN were exposed and microforceps (size 0.02×0.06 mm) were used to bilaterally crush the CN for 30 s. A visible indent and change in color of the nerve were apparent with crush injury. CN crushed rats were sacrificed after 2 days and were grown in organ culture.

Organ Culture:

The MPG and attached CN were dissected from adult and aged Sprague Dawley rats. Only the caudal portion of the MPG, which innervates the penis was included in the culture. The pelvic, hypogastric and ancillary nerves, and the regions of the MPG that innervate the bladder, rectum and prostate, were excluded from culture. MPG/CN were placed in sterile culture plates containing 150 µl of reduced growth factor Matrigel (Corning Life Sciences 356,231). Reduced growth factor Matrigel was used for this study so that the Matrigel did not influence neurite formation. Affi-Gel beads (100-200 mesh, Bio Rad) were incubated overnight at 4° C. with 1×PBS, SHH protein (25 µl of a 1 µg/µl solution, R&D Systems), or 5E1 SHH inhibitor (388 µg/ml, Hybridoma Bank), and were placed on top of the Matrigel near the MPG/CN. Matrigel was gelled at 37° C. for 5 min prior to adding RPMI media (Sigma) and an antibiotic cocktail containing Penicillin-Streptomycin-Glutamine (100×, Thermo Fisher Scientific). Culture plates were placed in an atmosphere-controlled incubator (5% CO2) at 37° C. for three days. Groups were uninjured adult and aged MPG/CN treated with PBS (control, n=6), SHH protein (n=6) and 5E1 SHH inhibitor (n=2), and CN crushed MPG/CN from adult and aged rats treated with PBS (n=9), SHH protein (n=6), and 5E1 SHH inhibitor (n=2). Additional aged rat MPG/CN including the hypogastric and pelvic nerves, underwent CN crush and after 2 days in vivo, were grown in organ culture with PBS (n=2) or SHH protein (n=2) as outlined above.

Quantification of Neurites:

Neurites were quantified by counting the total number of growth cones visible for each tissue grown in organ culture by a blinded observer at 160× magnification, normalized by tissue perimeter length (mm). Photos of the MPG/CN were magnified on the computer screen until growth cones were visible, and growth cones in the entire tissue were counted and the perimeter was measured. Three to five photos for each tissue were counted and averaged. Images were obtained using an Olympus SZ-CTV dissecting microscope and Axiocam R1.2 Carl Zeiss digital camera. Representative photos for each group are presented in the figures.

Immunohistochemical Analysis (IHC):

IHC was performed on frozen MPG/CN which were cut to 12 µm thickness and were post fixed in acetone for 15 min at 4° C. OCT was removed with 1×PBS washes prior to blocking with 3% milk in PBS at 4° C. for one hour. Sections were incubated overnight at 4° C. with 1/100 goat polyclonal antibody against patched (PTCH1) and GLI1 (Santa Cruz), rabbit polyclonal antibody against smoothened (SMO, LSBio), GLI2 and GLI3 (Rockland), and mouse monoclonal antibodies against neuronal nitric oxide synthase (nNOS, Transduction Laboratories), β-III tublin(Abcam), growth associated protein 43 (GAP43, Chemicon), Rhoactivated serine/threonine kinase (ROCK1, Transduction) and ROCK2 (Santa Cruz). Fluorescent secondary antibodies were chicken anti-goat 488, chicken anti-rabbit 594, and donkey anti-mouse 594 (Molecular Probes, 1/150). HRP secondary antibodies were 1/150 donkey anti-goat (Sigma-Aldrich), and mouse anti-rabbit (Santa Cruz). Control slides in which the primary antibody was omitted, were performed for all secondary antibodies, to ensure artifact staining was not present from the secondary antibodies. Sections were mounted using DPX Mounting media (Electron Microscopy Sciences, Hatfield, Pa.). Microscopy was performed using a Leica DM2500 microscope.

Statistical Analysis:

Statistical analysis was performed by ANOVA with a Scheffe's posthoc test using the SPSS program. The results were reported ±the standard error of the mean. Results were significantly different if p<0.05.

Results

Figure 25A:
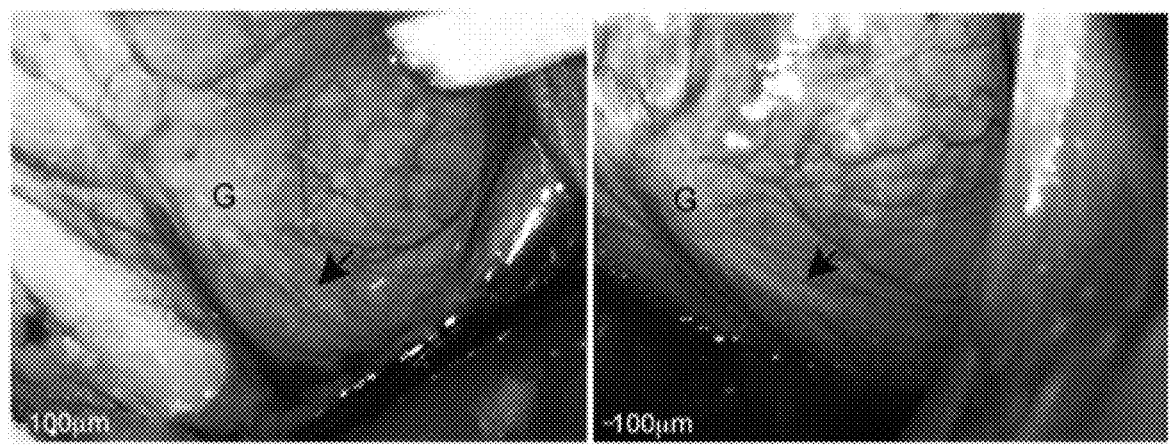
FIGS. 25A-25C.

Anatomy of the Pelvic Plexus:

Photos were taken of the pelvic plexus from adult (P115-120) and aged (P200-329) Sprague Dawley rats (FIG. 25A). The pelvic plexus was identified. The CN appears flat and thin in the adult rat with a small, clearly defined MPG (FIG. 25A). There is extensive vascular supply accompanying the neural tissue. In the aged rat, the CN is thicker and rounder in appearance (FIG. 25A). The MPG is larger and less well defined. The vascular supply does not appear diminished with age.

Figure 25B:
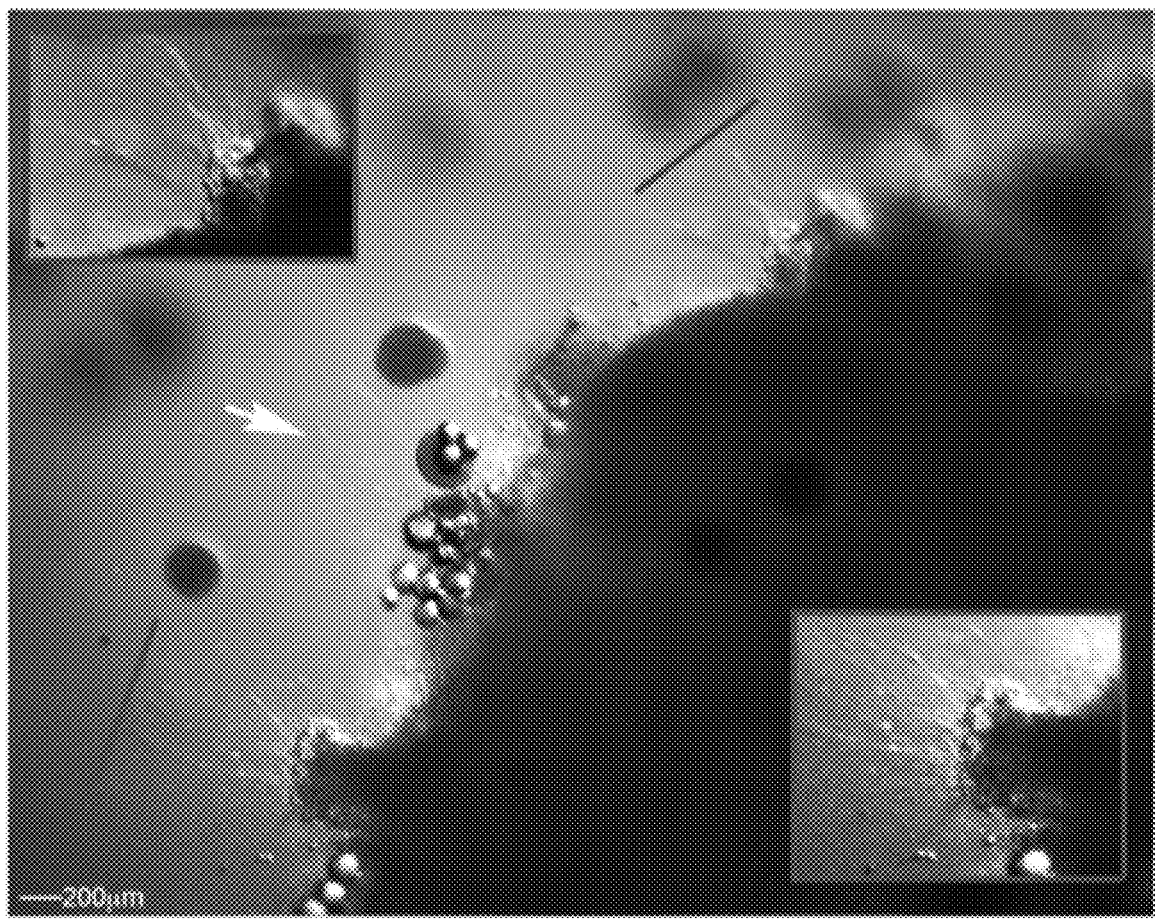
Figure 25C:
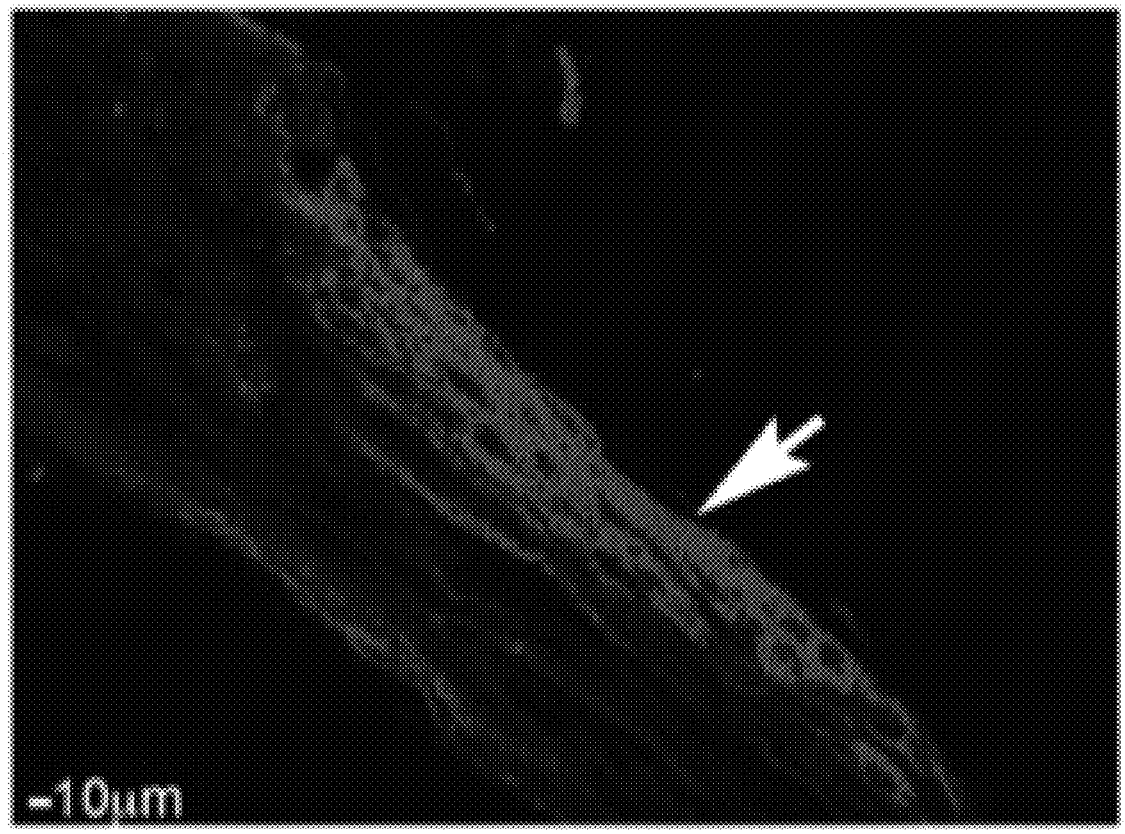

Neurite Formation in Uninjured MPG/CN:

Organ culture was performed on MPG/CN taken from uninjured Sprague Dawley rats and tissues were treated with SHH. A highly magnified view of the MPG shows growing neurites with clearly visible growth cones at the tips and elongating fibers (FIG. 25B, arrows indicate visible growth cones). In order to confirm the presence of neurites, we performed GAP43 (growth cones marker) immunohistochemical analysis. GAP43 was identified in elongating neurites of the CN (FIG. 25C).

Figure 26A:
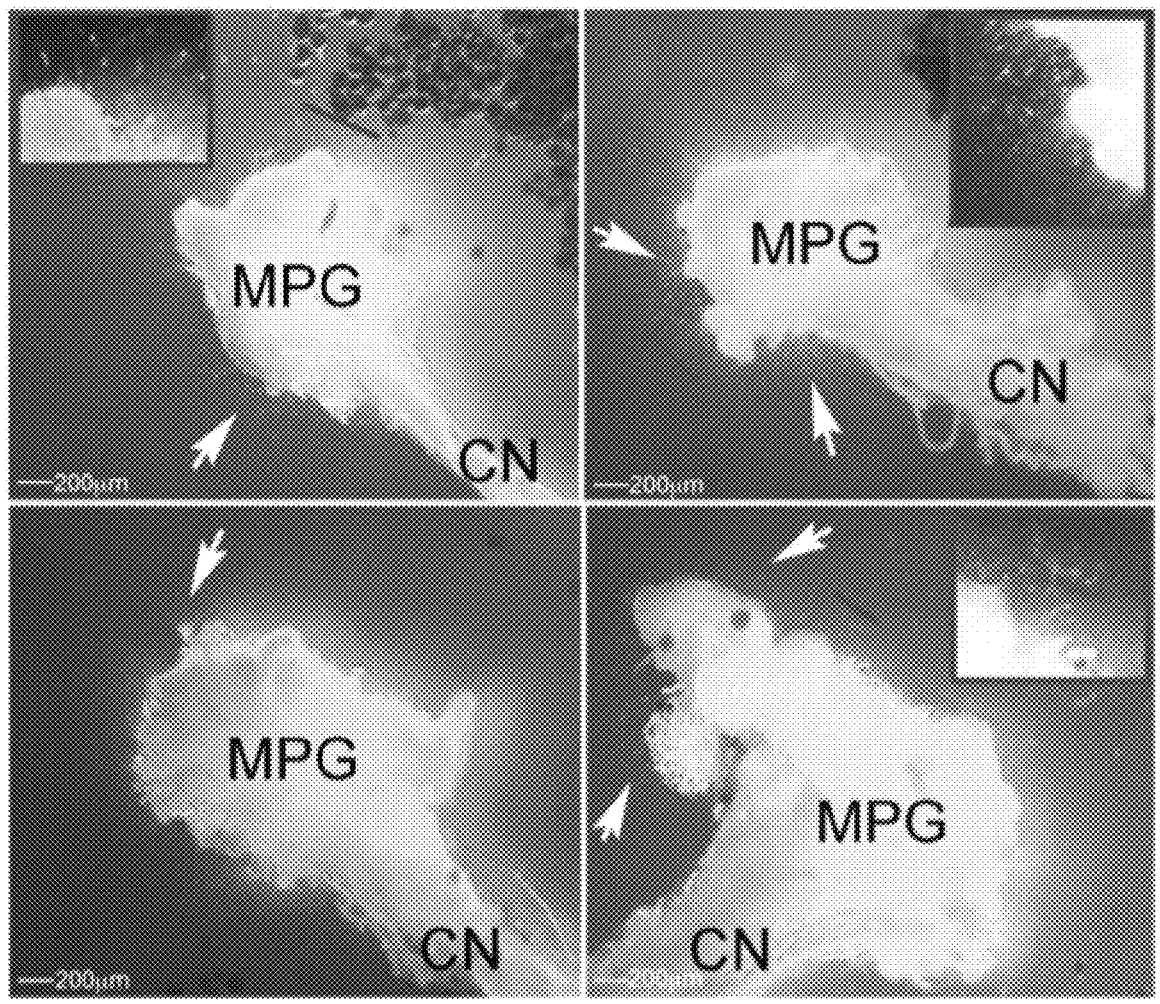
FIGS. 26A-26B. Uninjured adult and aged MPG were grown in organ culture for 3 days with PBS (control) or SHH protein and neurites were quantified (FIGS. 26A and 26B). The number of neurites/mm increased 3.5 fold with SHH treatment in adult rats (249%, p=0.0001). The number of neurites/mm increased 5.7-fold with SHH treatment in aged rats (468%, p=0.013). There was no difference in neurite formation in adult and aged rats treated with PBS (control, p=0.085). SHH treatment was 2.7-fold less in aged rats in comparison to SHH treated adult rats (63%, p=0.001). 800× magnification.
Figure 26B:
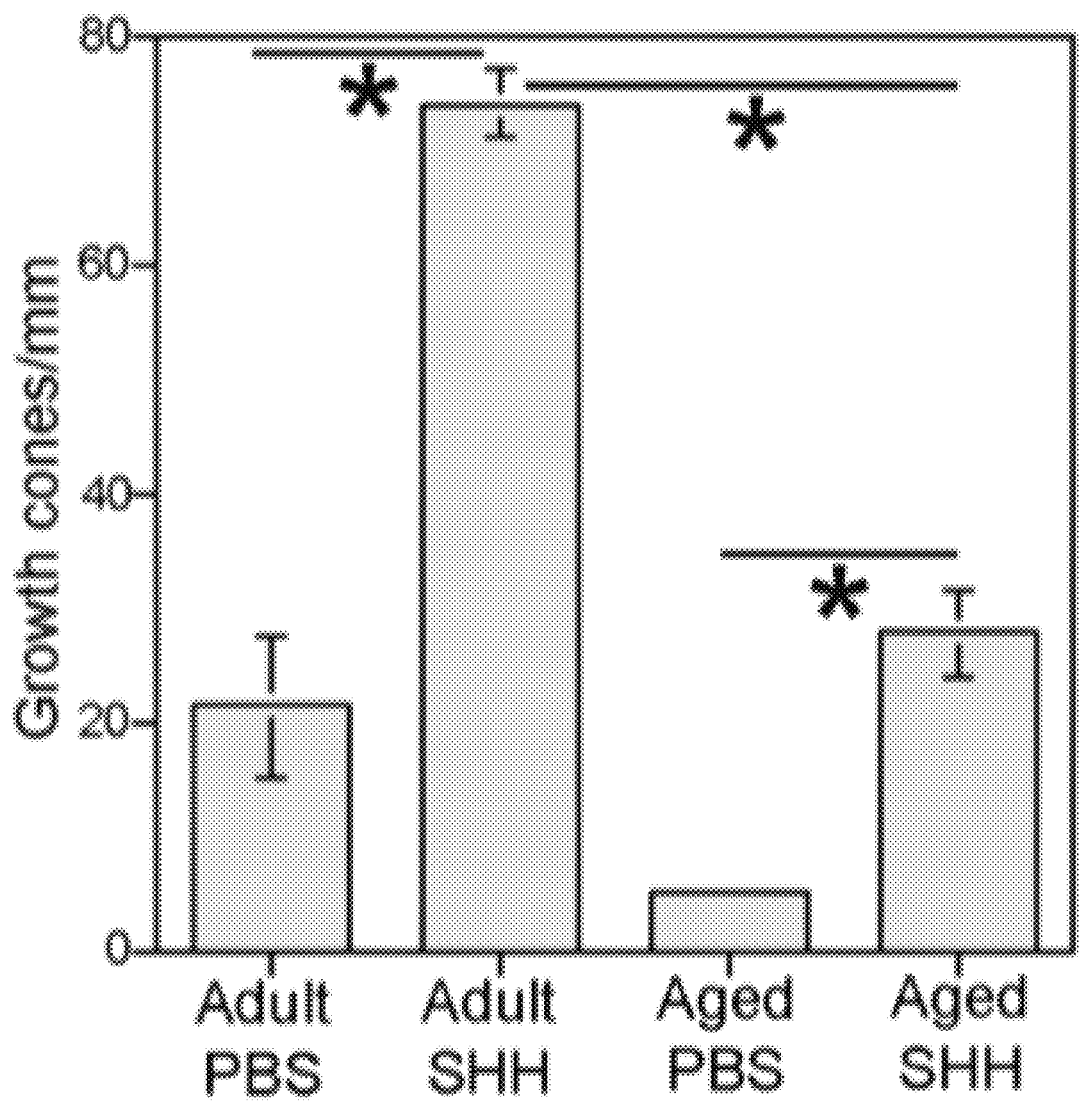

Comparison of Neurite Formation in Uninjured/Normal Adult and Aged Rat MPG:

Uninjured/normal adult and aged MPG were grown in organ culture for 3 days with PBS (control) or SHH protein and neurites were quantified by counting the number of growth cones/mm of tissue. The number of neurites/mm increased 3.5 fold with SHH treatment in adult rats (249%, p=0.0001, FIGS. 26A and B). The number of neurites/mm increased 5.7-fold with SHH treatment in aged rats (468%, p=0.013, FIGS. 26A and B). There was no difference in neurite formation in adult and aged rats treated with PBS (control, p=0.085, FIGS. 26 A and B). SHH treatment was 2.7-fold less in aged rats in comparison to SHH treated adult rats (63%, p=0.001, FIGS. 26A and B).

Figure 27A:
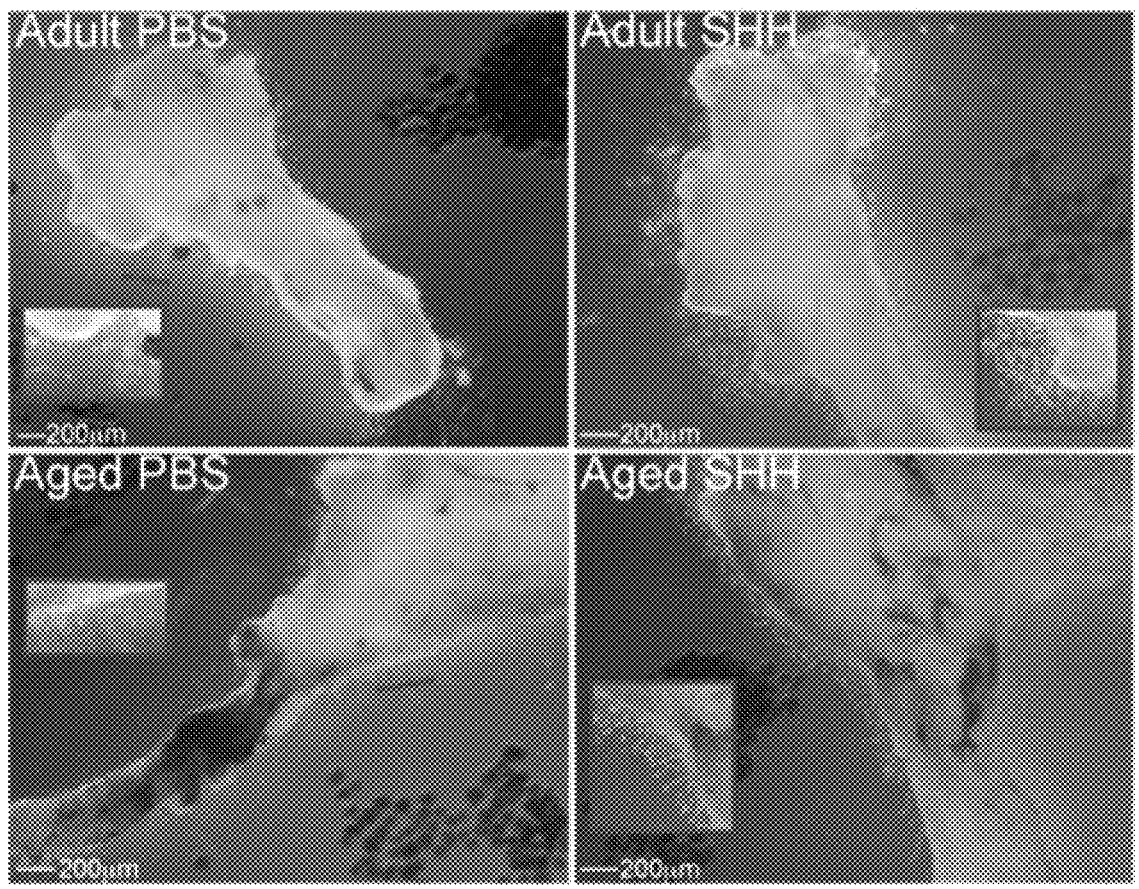
FIGS. 27A-27B. Adult and aged MPG that under went CN crush and were isolated after two days were grown in organ culture for 3 days with PBS (control) or SHH protein, and neurites were quantified (FIGS. 27A and 27B). The number of neurites/mm increased 1.8 fold with SHH treatment in adult rats (82%, p=0.044). The number of neurites/mm increased 2.5-fold with SHH treatment in aged rats (150%, p=0.030). There was no difference in neurite formation in adult and aged rats treated with PBS (control, p=0.298) or with SHH protein (p=0.197). Red line indicates enlarged region. 800× magnification.
Figure 27B:
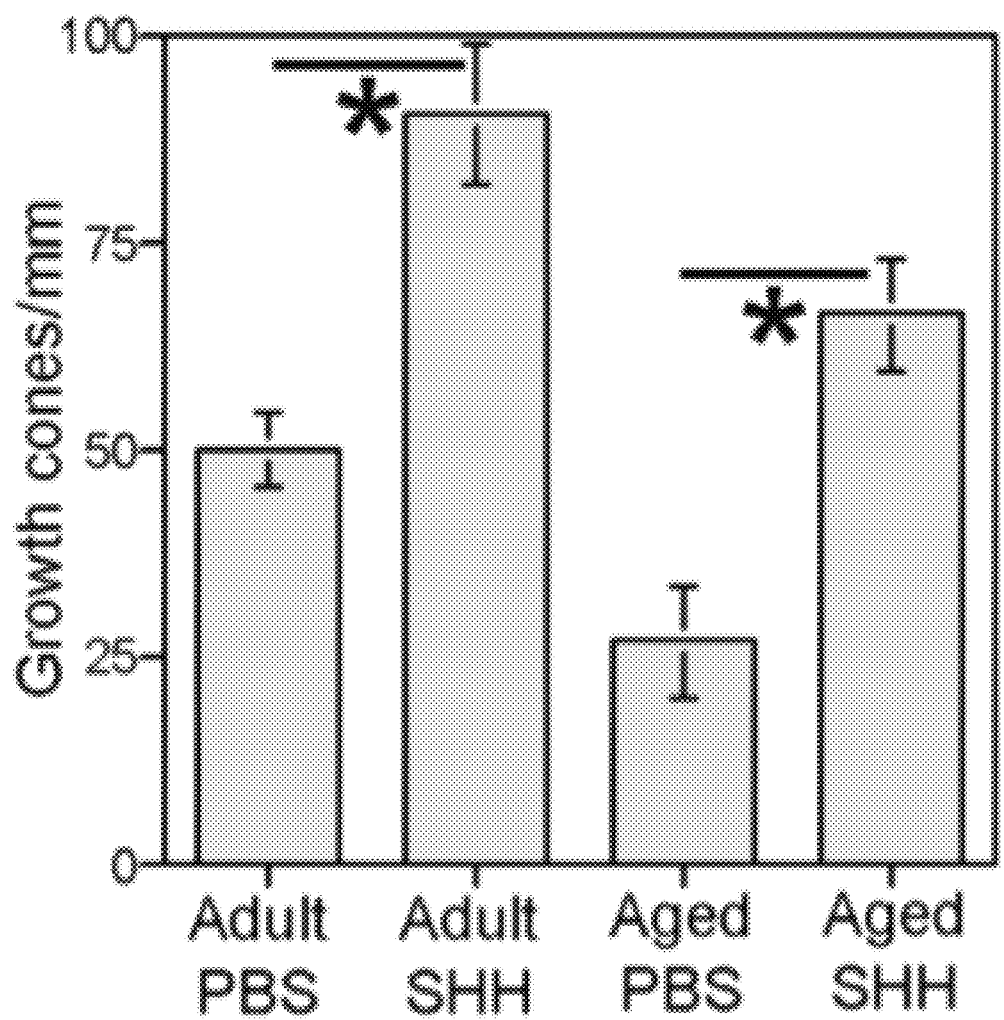

Comparison of Neurite Formation in 2 Day CN Crushed Adult and Aged Rat MPG:

Adult and aged MPG that underwent CN crush were isolated after two days and were grown in organ culture for 3 days with PBS (control) or SHH protein and neurites were quantified. The number of neurites/mm increased 1.8 fold with SHH treatment in adult rats (82%, p=0.044, FIG. 27A and FIG. 27B). The number of neurites/mm increased 2.5 fold with SHH treatment in aged rats (150%, p=0.030, FIG. 27A and FIG. 27B). There was no difference in neurite formation in adult and aged rats treated with PBS (control, p=0.298) or SHH (p=0.0.197, FIG. 27A and FIG. 27B).

CONCLUSIONS

Reintroduction of SHH protein in an aged prostatectomy model is even more effective in promoting neurite formation/CN regeneration than in the adult. The first 48 h after CN injury are a critical window when growth factors are released, that impact later neurite formation. These studies are significant because most prostatectomy patients are not young and healthy, as with adult rats, so the aged prostatectomy model will more accurately simulate erectile dysfunction patient response. Understanding how neurite formation changes with age is critical for clinical translation of SHH to prostatectomy patients.

We claim:

1. A method of treating and/or preventing erectile dysfunction in a subject, comprising administering to the subject a composition including a sonic hedgehog protein and a delivery vehicle, wherein the sonic hedgehog protein comprises an amino acid sequence having at least 95% sequence identity to SEQ ID NO: 1, SEQ ID NO: 2, or SEQ ID NO: 3, and wherein the composition is administered to the subject by applying to the corpora cavernosa and the cavernous nerve of the subject.

2. The method of claim 1, wherein the delivery vehicle comprises one or more peptide amphiphiles, wherein each peptide amphiphile comprises a hydrophobic tail, a structural peptide segment, and a charged peptide segment.

3. The method of claim 2, wherein the hydrophobic tail comprises an 8-24 carbon alkyl chain ($C_{8-24}$), the structural peptide segment has propensity to form β-sheet-like structures with adjacent structural peptide segments, and the charged peptide segment comprises an acidic, basic, or zwitterionic peptide segment.

4. The method of claim 3, wherein the structural peptide segment comprises $V_2A_2$, $V_3A_3$, $V_2A_3$, or $V_3A_2$ and the charged peptide segment comprises $E_2$, $E_3$, or $E_4$.

5. The method of claim 2, wherein each peptide amphiphile further comprises a C-terminal moiety independently selected from —H, —OH, —COOH, —CONH$_2$, and —NH$_2$.

6. The method of claim 2, wherein each peptide amphiphile comprises $C_{16}$—$V_3A_3E_3$-COOH or $C_{16}$—$V_2A_2E_2$-NH$_2$.

7. The method of claim 6, wherein the peptide amphiphile $C_{16}$—$V_3A_3E_3$-COOH is used for delivery of the sonic hedgehog protein to the corpora cavernosa and the peptide amphiphile $C_{16}$—$V_2A_2E_2$-NH$_2$ is used for delivery of the sonic hedgehog protein to the cavernous nerve of the subject.

8. The method of claim 1, wherein the composition is administered to the subject prior to or at the time of prostatectomy in the subject, and/or following one or more of crush injury to the cavernous nerve, tension injury of the pelvic ganglia, and injury to penile smooth muscle tissue of the subject.

9. The method of claim 1, wherein the subject is aged and/or diabetic.

10. The method of claim 1, wherein administration of the composition prevents smooth muscle apoptosis and/or penile remodeling in the subject.

11. The method of claim 1, wherein administration of the composition promotes regeneration of one or more tissues selected from smooth muscle tissue, pelvic ganglia tissue, and cavernous nerve tissue.

* * * * *

SEQUENCE LISTING

```
<160> NUMBER OF SEQ ID NOS: 3

<210> SEQ ID NO 1
<211> LENGTH: 123
<212> TYPE: PRT
<213> ORGANISM: Homo sapiens
```

```
<400> SEQUENCE: 1

Met Leu Ser Leu Phe Pro Ser Pro Gly Pro Gly Ser Ser Arg Cys Lys
1               5                   10                  15

Asp Lys Leu Asn Ala Leu Ala Ile Ser Val Met Asn Gln Trp Pro Gly
            20                  25                  30

Val Lys Leu Arg Val Thr Glu Gly Trp Asp Glu Asp Gly His His Ser
        35                  40                  45

Glu Glu Ser Leu His Tyr Glu Gly Arg Ala Val Asp Ile Thr Thr Ser
    50                  55                  60

Asp Arg Asp Arg Ser Lys Tyr Gly Met Leu Ala Arg Leu Ala Val Glu
65                  70                  75                  80

Ala Gly Phe Asp Trp Val Tyr Tyr Glu Ser Lys Ala His Ile His Cys
                85                  90                  95

Ser Val Lys Ala Val Gln Ser Asp Phe Lys Ser Val Glu Ser Glu Pro
            100                 105                 110

Glu Ala Pro Gly Thr Ala Ala Pro Leu Ala Val
            115                 120

<210> SEQ ID NO 2
<211> LENGTH: 180
<212> TYPE: PRT
<213> ORGANISM: Mus musculus

<400> SEQUENCE: 2

Cys Gly Pro Gly Arg Gly Phe Gly Lys Arg Arg His Pro Lys Lys Leu
1               5                   10                  15

Thr Pro Leu Ala Tyr Lys Gln Phe Ile Pro Asn Val Ala Glu Lys Thr
            20                  25                  30

Leu Gly Ala Ser Gly Arg Tyr Glu Gly Lys Ile Thr Arg Asn Ser Glu
        35                  40                  45

Arg Phe Lys Glu Leu Thr Pro Asn Tyr Asn Pro Asp Ile Ile Phe Lys
    50                  55                  60

Asp Glu Glu Asn Thr Gly Ala Asp Arg Leu Met Thr Gln Arg Cys Lys
65                  70                  75                  80

Asp Lys Leu Asn Ala Leu Ala Ile Ser Val Met Asn Gln Trp Pro Gly
                85                  90                  95

Val Lys Leu Arg Val Thr Glu Gly Trp Asp Glu Asp Gly His His Ser
            100                 105                 110

Glu Glu Ser Leu His Tyr Glu Gly Arg Ala Val Asp Ile Thr Thr Ser
        115                 120                 125

Asp Arg Asp Arg Ser Lys Tyr Gly Met Leu Ala Arg Leu Ala Val Glu
    130                 135                 140

Ala Gly Phe Asp Trp Val Tyr Tyr Glu Ser Lys Ala His Ile His Cys
145                 150                 155                 160

Ser Val Lys Ala Glu Asn Ser Val Ala Ala Lys Ser Gly Gly His His
                165                 170                 175

His His His His
            180

<210> SEQ ID NO 3
<211> LENGTH: 437
<212> TYPE: PRT
<213> ORGANISM: Mus musculus
```

<400> SEQUENCE: 3

```
Met Leu Leu Leu Leu Ala Arg Cys Phe Leu Val Ile Leu Ala Ser Ser
1               5                   10                  15

Leu Leu Val Cys Pro Gly Leu Ala Cys Gly Pro Gly Arg Gly Phe Gly
            20                  25                  30

Lys Arg Arg His Pro Lys Lys Leu Thr Pro Leu Ala Tyr Lys Gln Phe
        35                  40                  45

Ile Pro Asn Val Ala Glu Lys Thr Leu Gly Ala Ser Gly Arg Tyr Glu
    50                  55                  60

Gly Lys Ile Thr Arg Asn Ser Glu Arg Phe Lys Glu Leu Thr Pro Asn
65                  70                  75                  80

Tyr Asn Pro Asp Ile Ile Phe Lys Asp Glu Glu Asn Thr Gly Ala Asp
                    85                  90                  95

Arg Leu Met Thr Gln Arg Cys Lys Asp Lys Leu Asn Ala Leu Ala Ile
                100                 105                 110

Ser Val Met Asn Gln Trp Pro Gly Val Lys Leu Arg Val Thr Glu Gly
            115                 120                 125

Trp Asp Glu Asp Gly His His Ser Glu Glu Ser Leu His Tyr Glu Gly
        130                 135                 140

Arg Ala Val Asp Ile Thr Thr Ser Asp Arg Asp Arg Ser Lys Tyr Gly
145                 150                 155                 160

Met Leu Ala Arg Leu Ala Val Glu Ala Gly Phe Asp Trp Val Tyr Tyr
                165                 170                 175

Glu Ser Lys Ala His Ile His Cys Ser Val Lys Ala Glu Asn Ser Val
                180                 185                 190

Ala Ala Lys Ser Gly Gly Cys Phe Pro Gly Ser Ala Thr Val His Leu
            195                 200                 205

Glu Gln Gly Gly Thr Lys Leu Val Lys Asp Leu Arg Pro Gly Asp Arg
        210                 215                 220

Val Leu Ala Ala Asp Asp Gln Gly Arg Leu Leu Tyr Ser Asp Phe Leu
225                 230                 235                 240

Thr Phe Leu Asp Arg Asp Glu Gly Ala Lys Lys Val Phe Tyr Val Ile
                245                 250                 255

Glu Thr Leu Glu Pro Arg Glu Arg Leu Leu Leu Thr Ala Ala His Leu
                260                 265                 270

Leu Phe Val Ala Pro His Asn Asp Ser Gly Pro Thr Pro Gly Pro Ser
            275                 280                 285

Ala Leu Phe Ala Ser Arg Val Arg Pro Gly Gln Arg Val Tyr Val Val
        290                 295                 300

Ala Glu Arg Gly Gly Asp Arg Arg Leu Leu Pro Ala Ala Val His Ser
305                 310                 315                 320

Val Thr Leu Arg Glu Glu Glu Ala Gly Ala Tyr Ala Pro Leu Thr Ala
                325                 330                 335

His Gly Thr Ile Leu Ile Asn Arg Val Leu Ala Ser Cys Tyr Ala Val
                340                 345                 350

Ile Glu Glu His Ser Trp Ala His Arg Ala Phe Ala Pro Phe Arg Leu
            355                 360                 365

Ala His Ala Leu Leu Ala Ala Leu Ala Pro Ala Arg Thr Asp Gly Gly
        370                 375                 380

Gly Gly Gly Ser Ile Pro Ala Ala Gln Ser Ala Thr Glu Ala Arg Gly
385                 390                 395                 400

Ala Glu Pro Thr Ala Gly Ile His Trp Tyr Ser Gln Leu Leu Tyr His
                405                 410                 415
```

```
Ile Gly Thr Trp Leu Leu Asp Ser Glu Thr Met His Pro Leu Gly Met
            420                 425                 430

Ala Val Lys Ser Ser
        435
```